(12) United States Patent
Hwang et al.

(10) Patent No.: US 9,806,267 B2
(45) Date of Patent: Oct. 31, 2017

(54) COMPOUND AND ORGANIC LIGHT-EMITTING DEVICE COMPRISING THE COMPOUND

(71) Applicant: SAMSUNG DISPLAY CO., LTD., Yongin, Gyeonggi-Do (KR)

(72) Inventors: Seok-Hwan Hwang, Yongin (KR); Soo-Yon Kim, Yongin (KR); Jong-Woo Kim, Yongin (KR)

(73) Assignee: Samsung Display Co., Ltd., Yongin-si (KR)

( * ) Notice: Subject to any disclaimer, the term of this patent is extended or adjusted under 35 U.S.C. 154(b) by 304 days.

(21) Appl. No.: 14/516,498

(22) Filed: Oct. 16, 2014

(65) Prior Publication Data
US 2015/0162544 A1    Jun. 11, 2015

(30) Foreign Application Priority Data
Dec. 9, 2013 (KR) .................. 10-2013-0152638

(51) Int. Cl.
*H01L 51/00* (2006.01)
*C07D 403/14* (2006.01)
*H01L 51/50* (2006.01)

(52) U.S. Cl.
CPC ........ *H01L 51/0067* (2013.01); *C07D 403/14* (2013.01); *H01L 51/0072* (2013.01);
(Continued)

(58) Field of Classification Search
None
See application file for complete search history.

(56) References Cited

U.S. PATENT DOCUMENTS 9,246,109 B2 *   1/2016   Kim ................ C07D 403/04
2005/0002857 A1  1/2005   Pez et al.
(Continued)

FOREIGN PATENT DOCUMENTS

EP         2 433 928 A1    3/2012
KR    10-2011-0088427      8/2011
(Continued)

OTHER PUBLICATIONS

Machine English translation of KR 10-2014-0091487. Sep. 22, 2016.*
KIPO Office action dated Nov. 5, 2015, for Korean priority Patent application 10-2013-0152638, (6 pages).
English machine translation of Claims 1 and 2, for Korean Publication 10-2014-0091487 dated Jul. 21, 2014, (3 pages).
Adachi, Chihaya et al., "High-efficiency organic electrophosphorescent devices with tris(2-phenylpyridine)iridium doped into electron-transporting materials", Applied Physics Letters, Aug. 7, 2000, pp. 904-906, vol. 77, No. 6.
(Continued)

*Primary Examiner* — J. L. Yang
(74) *Attorney, Agent, or Firm* — Lewis Roca Rothgerber Christie LLP

(57) ABSTRACT

A compound is represented by Formula 1, and an organic light-emitting device includes the compound. Embodiments of the compound have excellent electrical properties, high charge-transporting and emission capabilities, high glass transition temperature, and are capable of reducing crystallization. Embodiments of organic light-emitting devices including the compound have high efficiency, low driving voltage, high brightness, and long lifespan.

(Continued)

Formula 1

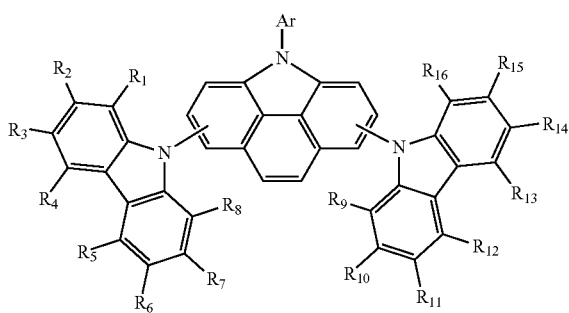

23 Claims, 1 Drawing Sheet

(52) U.S. Cl.
CPC ...... *H01L 51/0073* (2013.01); *H01L 51/0081* (2013.01); *H01L 51/0085* (2013.01); *H01L 51/5016* (2013.01)

(56) References Cited

U.S. PATENT DOCUMENTS

| | | |
|---|---|---|
| 2009/0019768 A1 | 1/2009 | Toseland et al. |
| 2014/0001449 A1 | 1/2014 | Maunoury et al. |

FOREIGN PATENT DOCUMENTS

| | | |
|---|---|---|
| KR | 10-2012-0062424 | 6/2012 |
| KR | 10-2014-0091487 | 7/2014 |

OTHER PUBLICATIONS

Baldo, M.A. et al., "Highly efficient phosphorescent emission from organic electroluminescent devices", Letters to Nature, Sep. 10, 1998, pp. 151-154, vol. 395.

Baldo, M.A. et al., "Very high-efficiency green organic light-emitting devices based on electrophosphorescence", Applied Physics Letters, Jul. 5, 1999, pp. 4-6, vol. 75, No. 1.

Kwong, Raymond C. et al., "High operational stability of electrophosphorescent devices", Applied Physics Letters, Jul. 1, 2002, pp. 162-164, vol. 81, No. 1.

\* cited by examiner

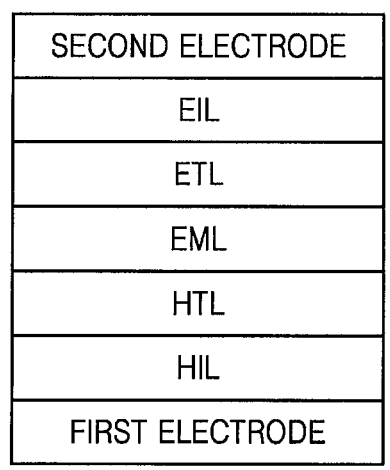

COMPOUND AND ORGANIC LIGHT-EMITTING DEVICE COMPRISING THE COMPOUND

CROSS-REFERENCE TO RELATED APPLICATION

This application claims priority to and the benefit of Korean Patent Application No. 10-2013-0152638, filed on Dec. 9, 2013, in the Korean Intellectual Property Office, the entire content of which is incorporated herein in its entirety by reference.

BACKGROUND

1. Field

One or more aspects of embodiments of the present invention relate to a compound and an organic light-emitting device including the compound.

2. Description of the Related Art

Organic light-emitting devices (OLEDs) are self-emitting devices that have advantages such as wide viewing angles, excellent contrast, quick response times, and excellent brightness, driving voltage, and response speed characteristics, and can provide multicolored images.

An OLED may have a structure including an anode, a hole-transporting layer (HTL), an emission layer (EML), an electron-transporting layer (ETL), and a cathode, which are sequentially stacked in the stated order on a substrate. In this regard, the HTL, the EML, and the ETL are organic thin films including (e.g., formed of) organic compounds.

An operating principle of an OLED having the above-described structure is as follows.

When a voltage is applied between the anode and the cathode, holes injected from the anode move to the EML via the HTL, and electrons injected from the cathode move to the EML via the ETL. Carriers, such as the holes and electrons, recombine in the EML to generate excitons. When the excitons drop (e.g., relax) from an excited state to a ground state, light is emitted.

Thus, materials that have excellent electrical stability, high charge transporting capability or light-emitting capability, high glass transition temperature, and that are capable of preventing (or reducing) crystallization compared with other organic monomolecular materials are desirable (or continuously required).

SUMMARY

One or more aspects of embodiments of the present invention are directed toward host compounds suitable for fluorescent and phosphorescent devices of all colors, such as red, green, blue, white, and the like. Embodiments of the host compounds are materials having excellent electrical properties, high charge-transporting and emission capabilities, high glass transition temperature, and are capable of preventing (or reducing) crystallization. Embodiments of organic light-emitting devices including the host compounds have high efficiency, low driving voltage, high brightness, and long lifespan.

Additional aspects will be set forth in part in the description which follows and, in part, will be apparent from the description, or may be learned by practice of the described embodiments.

According to one or more embodiments of the present invention, a compound is represented by Formula 1:

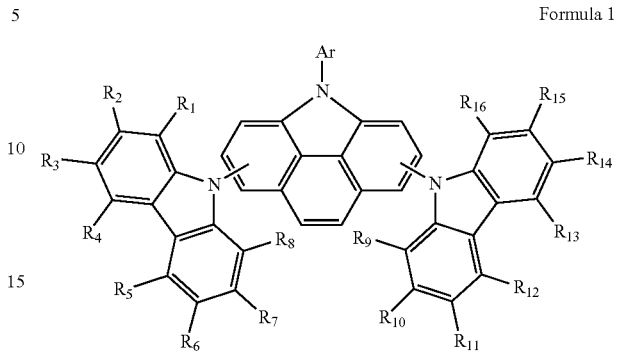

Formula 1 in Formula 1, $R_1$ to $R_{16}$ may be each independently a hydrogen atom; a deuterium atom; a halogen atom; a cyano group; a substituted or unsubstituted $C_1$-$C_{60}$ alkyl group; a substituted or unsubstituted $C_2$-$C_{60}$ alkenyl group; a substituted or unsubstituted $C_2$-$C_{60}$ alkynyl group; a substituted or unsubstituted $C_3$-$C_{60}$ cycloalkyl group; a substituted or unsubstituted $C_3$-$C_{60}$ cycloalkenyl group; a substituted or unsubstituted $C_6$-$C_{60}$ aryl group; a substituted or unsubstituted $C_1$-$C_{60}$ heteroaryl group; an amino group substituted with a $C_6$-$C_{60}$ aryl group or a $C_1$-$C_{60}$ heteroaryl group; or a substituted or unsubstituted $C_6$-$C_{60}$ condensed polycyclic group, and Ar is a substituted or unsubstituted $C_1$-$C_{60}$ alkyl group, a substituted or unsubstituted $C_6$-$C_{60}$ aryl group, a substituted or unsubstituted $C_1$-$C_{60}$ heteroaryl group, or a substituted or unsubstituted $C_6$-$C_{60}$ condensed polycyclic group.

According to another embodiment of the present invention, an organic light-emitting device includes: a first electrode; a second electrode; and an organic layer between the first electrode and the second electrode, where the organic layer includes the compound represented by Formula 1.

According to another aspect of an embodiment of the present invention, a flat display device includes the organic light-emitting device, where the first electrode of the organic light-emitting device is electrically connected to a source electrode or a drain electrode of a thin film transistor.

BRIEF DESCRIPTION OF THE DRAWING

These and/or other aspects will become apparent and more readily appreciated from the following description of the embodiments when considered together with the accompanying drawing, which is a schematic view of an organic light-emitting device according to an embodiment of the present invention.

DETAILED DESCRIPTION

Reference will now be made to certain embodiments, examples of which are illustrated in the accompanying drawing, where like reference numerals refer to like elements throughout. As those skilled in the art would recognize, the described embodiments may be modified in many ways and should, therefore, not be construed as limiting. Accordingly, the embodiments are described below, by referring to the figures, merely to explain aspects of the present disclosure. As used herein, the term "and/or" includes any and all combinations of one or more of the associated listed items. Expressions such as "at least one of," when preceding a list of elements, modify the entire list of elements and do not modify the individual elements of the list. Also, in the context of the present application, when a first element is referred to as being "on" a second element, it can be directly on the second element or be indirectly on the second element with one or more intervening elements therebetween.

A compound according to an embodiment of the present invention is represented by Formula 1 below:

Formula 1

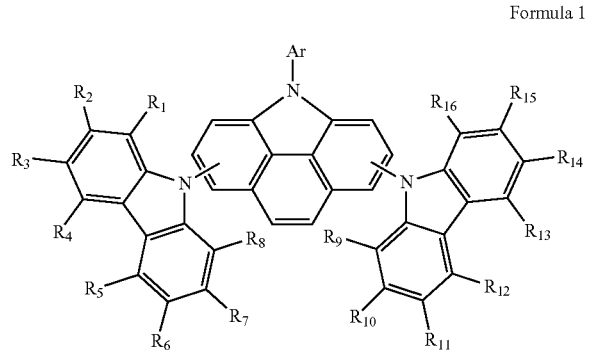

in Formula 1, $R_1$ to $R_{16}$ are each independently a hydrogen atom; a deuterium atom; a halogen atom; a cyano group; a substituted or unsubstituted $C_1$-$C_{60}$ alkyl group; a substituted or unsubstituted $C_2$-$C_{60}$ alkenyl group; a substituted or unsubstituted $C_2$-$C_{60}$ alkynyl group; a substituted or unsubstituted $C_3$-$C_{60}$ cycloalkyl group; a substituted or unsubstituted $C_3$-$C_{60}$ cycloalkenyl group; a substituted or unsubstituted $C_6$-$C_{60}$ aryl group; a substituted or unsubstituted $C_1$-$C_{60}$ heteroaryl group; an amino group substituted with a $C_6$-$C_{60}$ aryl group or a $C_1$-$C_{60}$ heteroaryl group; or a substituted or unsubstituted $C_6$-$C_{60}$ condensed polycyclic group, Ar represents a substituted or unsubstituted $C_1$-$C_{60}$ alkyl group, a substituted or unsubstituted $C_6$-$C_{60}$ aryl group, a substituted or unsubstituted $C_1$-$C_{60}$ heteroaryl group, or a substituted or unsubstituted $C_6$-$C_{60}$ condensed polycyclic group.

The compound of Formula 1 according to an embodiment of the present invention functions as an emission material for an organic light-emitting device. When the compound of Formula 1 includes a condensed ring, the compound of Formula 1 has a high glass transition temperature (Tg) or melting point due to the presence of the condensed ring. Accordingly, an organic layer including the compound of Formula 1 for electroluminescence has heat resistance to Joule heat (e.g., ohmic or resistive heating) that is generated in the organic layers, between the organic layers, or between the organic layer and a metal electrode, and has increased resistance in a high temperature environment. An organic light-emitting device manufactured by using (utilizing) a condensed cyclic compound according to an embodiment of the present invention has high durability during maintenance and driving. Also, including a substituent including a heteroatom in a molecule of the compound enhances properties of the organic-light emitting device.

In Formula 1, a substitution location of a carbazole group is not limited and Formula 1 may be represented by, for example, Formula 2 or Formula 3, but the present disclosure is not limited thereto.

Formula 2

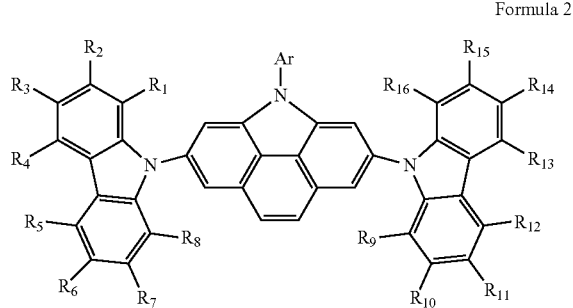

Formula 3

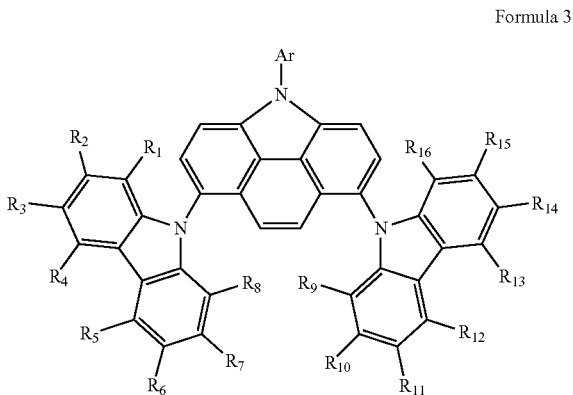

Descriptions of the substituents of Formula 2 and 3 are the same as described above and below with respect to the substituents of Formula 1.

According to an embodiment of the present invention, in Formula 1, $R_1$, $R_4$, $R_5$, $R_8$, $R_9$, $R_{12}$, $R_{13}$, and $R_{16}$ may be each independently a hydrogen atom or a deuterium atom.

According to another embodiment of the present invention, in Formula 1, Ar may be any one of Formulae 2a to 2g.

2a

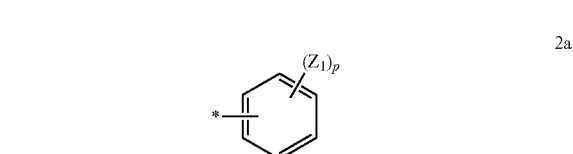

2b

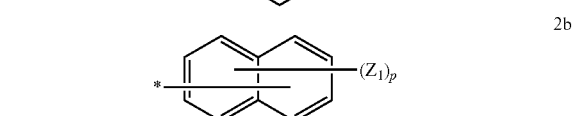

2c

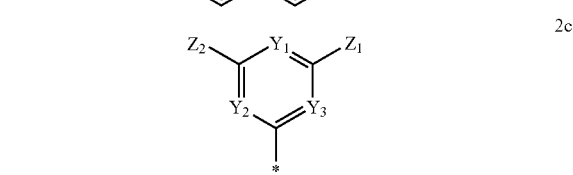

2d

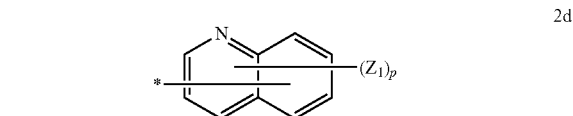

2e

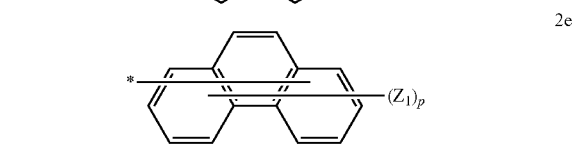

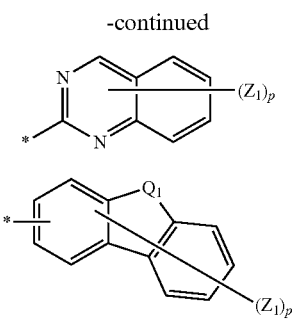

In Formulae 2a to 2g, $Q_1$ is —$C(R_{31})(R_{32})$—, —$N(R_{33})$—, —S—, or —O—;

$Z_1$, $Z_2$, $R_{31}$, $R_{32}$, and $R_{33}$ may be each independently, a hydrogen atom, a deuterium atom, a substituted or unsubstituted $C_1$-$C_{20}$ alkyl group, a substituted or unsubstituted $C_6$-$C_{20}$ aryl group, a substituted or unsubstituted $C_1$-$C_{20}$ heteroaryl group, a substituted or unsubstituted $C_6$-$C_{20}$ condensed polycyclic group, —$SiR_{41}R_{42}R_{43}$, a halogen atom, a cyano group, a nitro group, a hydroxy group, or a carboxy group;

$R_{41}$, $R_{42}$, and $R_{43}$ may be each independently a substituted or unsubstituted $C_1$-$C_{20}$ alkyl group or a substituted or unsubstituted $C_6$-$C_{20}$ aryl group;

$Y_1$ to $Y_3$ are each independently CH or N; p is an integer of 1 to 9 and * represents a bonding location (e.g., a binding site to N of any one of Formulae 1-3).

According to another embodiment of the present invention, in Formula 1, $R_2$, $R_3$, $R_6$, $R_7$, $R_{10}$, $R_{11}$, $R_{14}$, and $R_{15}$ may be each independently any one of Formulae 3a to 3b:

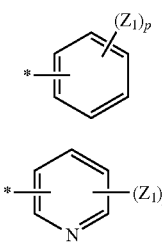

in Formulae 3a to 3b, $Z_1$ is a hydrogen atom, a deuterium atom, a substituted or unsubstituted $C_1$-$C_{20}$ alkyl group, a substituted or unsubstituted $C_6$-$C_{20}$ aryl group, a substituted or unsubstituted $C_1$-$C_{20}$ heteroaryl group, a substituted or unsubstituted $C_6$-$C_{20}$ polycyclic group, a halogen atom, a cyano group, a nitro group, a hydroxy group or a carboxy group;

p is an integer of 1 to 5; and * represents a bonding location (e.g., a binding site to a carbon of any one of Formulae 1-3).

Hereinafter, representative substituents are described as follows (in the description below, carbon numbers of the substituents are non-limiting and do not limit the properties of the substituents, and definitions of substituents that are not described herein are the same as general definitions, for example, as generally understood by those of ordinary skill in the art):

The unsubstituted $C_1$-$C_{60}$ alkyl group may have a linear or a branched form, and non-limiting examples of the unsubstituted $C_1$-$C_{60}$ alkyl group include methyl, ethyl, propyl, isobutyl, sec-butyl, pentyl, iso-amyl, hexyl, heptyl, octyl, nonacyl, dodecyl, and the like. The substituted $C_1$-$C_{60}$ alkyl group refers to the substitution of at least one hydrogen atom of the unsubstituted $C_1$-$C_{60}$ alkyl group with a deuterium atom, a halogen atom, a hydroxy group, a nitro group, a cyano group, an amino group, an amidino group, a hydrazine group, a hydrazone group, a carboxyl group or a salt thereof, a sulfonic acid group or a salt thereof, a phosphoric acid group or a salt thereof, a $C_1$-$C_{10}$ alkyl group, a $C_1$-$C_{10}$ alkoxy group, a $C_2$-$C_{10}$ alkenyl group, a $C_2$-$C_{10}$ alkynyl group, a $C_6$-$C_{16}$ aryl group, a $C_4$-$C_{16}$ heteroaryl group, or an organosilyl group.

The unsubstituted $C_2$-$C_{60}$ alkenyl group refers to a hydrocarbon chain having at least one carbon-carbon double bond inserted at the body (e.g., the center) or at a terminal end of the unsubstituted $C_2$-$C_{60}$ alkyl group. Non-limiting examples of the unsubstituted $C_2$-$C_{60}$ alkenyl group include ethenyl, propenyl, and butenyl. The substituted $C_2$-$C_{60}$ alkenyl group refers to the substitution of at least one hydrogen atom of the unsubstituted $C_2$-$C_{60}$ alkenyl group with a substituent as described above in connection with the substituted $C_1$-$C_{60}$ alkyl group.

The unsubstituted $C_2$-$C_{60}$ alkynyl group refers to an unsubstituted $C_2$-$C_{60}$ alkyl group having at least one carbon-carbon triple bond inserted at the body (e.g., the center) or at a terminal end of the $C_2$-$C_{60}$ alkyl group. Non-limiting examples of the unsubstituted $C_2$-$C_{60}$ alkynyl group include acetylene, propylene, phenyl acetylene, isopropyl acetylene, t-butyl acetylene, and diphenyl acetylene. The substituted $C_2$-$C_{60}$ alkynyl group refers to the substitution of at least one hydrogen atom of the $C_2$-$C_{60}$ alkynyl group with a substituent as described above in connection with the substituted $C_1$-$C_{60}$ alkyl group.

The unsubstituted $C_3$-$C_{60}$ cycloalkyl group refers to a $C_3$-$C_{60}$ alkyl group in a ring form (e.g., having a cyclic ring). The substituted $C_3$-$C_{60}$ cycloalkyl group refers to the substitution of at least one hydrogen atom of the unsubstituted $C_3$-$C_{60}$ cycloalkyl group with a substituent as described above in connection with the substituted $C_1$-$C_{60}$ alkyl group.

The unsubstituted $C_1$-$C_{60}$ alkoxy group may be a group having a formula (or a structure) of —OA (where, A is the unsubstituted $C_1$-$C_{60}$ alkyl group as described above). Non-limiting examples of the alkoxy group include methoxy, ethoxy, propoxy, isopropyloxy, butoxy, and pentoxy. The substituted $C_1$-$C_{60}$ alkoxy group refers to the substitution of at least one hydrogen atom of the unsubstituted $C_1$-$C_{60}$ alkoxy group with a substituent as described above in connection with the substituted $C_1$-$C_{60}$ alkyl group.

The unsubstituted $C_6$-$C_{60}$ aryl group refers to a carbocyclic aromatic system having at least one ring, and when there are two or more rings, the two or more rings may be fused, or connected to each other via a single bond. The term "aryl" as used herein includes aromatic systems such as phenyl, naphthyl, and anthracenyl. The substituted $C_6$-$C_{60}$ aryl group refers to the substitution of at least one hydrogen atom of the unsubstituted $C_6$-$C_{60}$ aryl group with a substituent as described above in connection with the substituted $C_1$-$C_{60}$ alkyl group.

Non-limiting examples of a substituted or unsubstituted $C_6$-$C_{60}$ aryl group include a phenyl group, a $C_1$-$C_{10}$ alkyl-phenyl group (for example, an ethylphenyl group), a halophenyl group (for example, an o-, m-, or p-fluorophenyl group or dichlorophenyl group), a cyanophenyl group, a dicyanophenyl group, a trifluoromethoxy phenyl group, a biphenyl group, a halobiphenyl group, a cyanobiphenyl group, a $C_1$-$C_{10}$ alkyl biphenyl group, a $C_1$-$C_{10}$ alkoxy biphenyl group, an o-, m-, or p-tolyl group, an o-, m-, or p-cumenyl group, a mesityl group, a phenoxy phenyl group, an (α,α-dimethyl benzene) phenyl group, an (N,N'-dimethyl)aminophenyl group, an (N,N'-diphenyl)aminophenyl group, a pentalenyl group, an indenyl group, a naphthyl group, a halonaphthyl group (for example, a fluoronaphthyl group), a $C_1$-$C_{10}$ alkyl naphthyl group (for example, a methyl naphthyl group), a $C_1$-$C_{10}$ alkoxy naphthyl group (for example, a methoxy naphthyl group), a cyanonaphthyl group, an anthracenyl group, an azulenyl group, a heptalenyl group, an acenaphthylenyl group, a phenalenyl group, a fluorenyl group, an anthraquinolyl group, a methyl anthryl group, a phenanthryl group, a triphenylene group, a pyrenyl group, a chrysenyl group, an ethyl-chrysenyl group, a picenyl group, a perylenyl group, a chloroperylenyl group, a pentaphenyl group, a pentacenyl group, a tetraphenylenyl group, a hexaphenyl group, a hexacenyl group, a rubicenyl group, a coronenyl group, a trinaphthylenyl group, a heptaphenyl group, a heptacenyl group, a pyranthrenyl group, and an ovalenyl group.

The unsubstituted $C_1$-$C_{60}$ heteroaryl group may include 1, 2, 3, or 4 heteroatoms selected from among N, O, P, and S, and when there are two or more rings, the two or more rings may be fused, or connected to each other via a single bond. Non-limiting examples of the unsubstituted $C_1$-$C_{60}$ heteroaryl group include a pyrazolyl group, an imidazolyl group, an oxazolyl group, a thiazolyl group, a triazolyl group, a tetrazolyl group, an oxadiazolyl group, a pyridinyl group, a pyridazinyl group, a pyrimidinyl group, a triazinyl group, a carbazolyl group, an indolyl group, a quinolinyl group, an isoquinolinyl group, and a dibenzothiophene group. The substituted $C_1$-$C_{60}$ heteroaryl group refers to the substitution of at least one hydrogen atom of the $C_1$-$C_{60}$ heteroaryl group with a substituent as described above in connection with the substituted $C_1$-$C_{60}$ alkyl group.

The unsubstituted $C_6$-$C_{60}$ aryloxy group refers to a group represented by —$OA_1$, where $A_1$ is the unsubstituted $C_6$-$C_{60}$ aryl group. Non-limiting examples of the unsubstituted $C_6$-$C_{60}$ aryloxy group include a phenoxy group. The substituted $C_6$-$C_{60}$ aryloxy group refers to the substitution of at least one hydrogen atom of the unsubstituted $C_6$-$C_{60}$ aryloxy group with a substituent as described above in connection with the substituted $C_1$-$C_{60}$ alkyl group.

The unsubstituted $C_6$-$C_{60}$ arylthio group refers to a group represented by —$SA_1$, where $A_1$ is the unsubstituted $C_6$-$C_{60}$ aryl group. Non-limiting examples of the arylthio group include a benzenethio group and a naphthylthio group. The substituted $C_6$-$C_{60}$ arylthio group refers to the substitution of at least one hydrogen atom of the unsubstituted $C_6$-$C_{60}$ arylthio group with a substituent as described above in connection with the substituted $C_1$-$C_{60}$ alkyl group.

The substituted or unsubstituted $C_6$-$C_{60}$ condensed polycyclic group refers to substituents including two or more rings in which at least one aromatic ring and at least one non-aromatic ring are fused together or substituents including unsaturated groups in a ring having a non-conjugated structure (or substituents including unsaturated groups in the ring but are incapable of having a conjugated structure). Thus, the substituted or unsubstituted $C_6$-$C_{60}$ condensed polycyclic group is distinguished from the above-described aryl groups and heteroaryl groups in that the substituted or unsubstituted $C_6$-$C_{60}$ condensed polycyclic group does not have an overall aromaticity (e.g., it is not aromatic).

Compounds 1-57 are examples of compounds represented by Formula 1 according to embodiments of the present invention, but the compound represented by Formula 1 is not limited thereto:

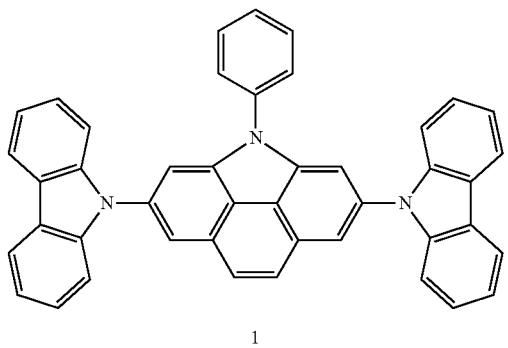

1

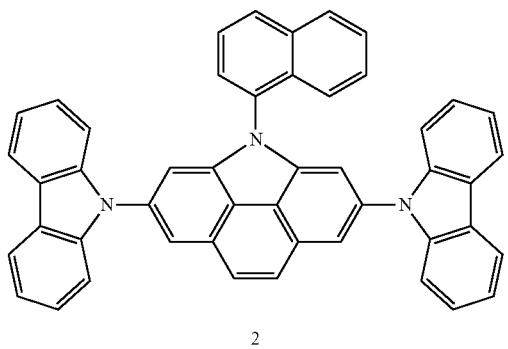

2

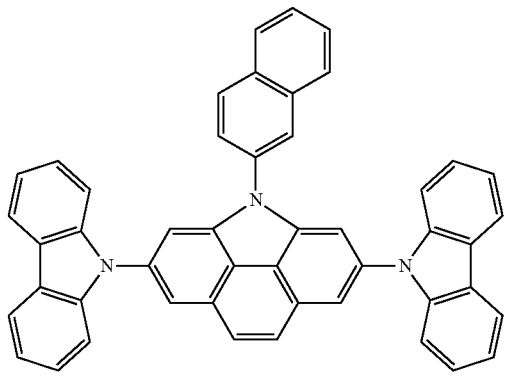

3

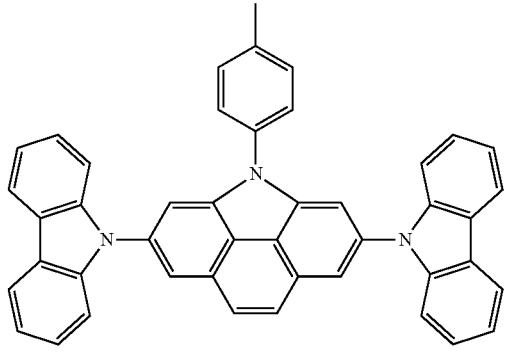

4

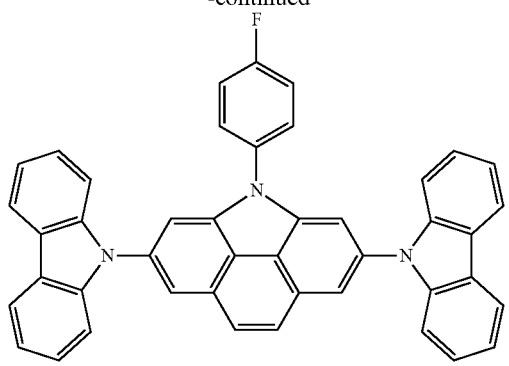
5
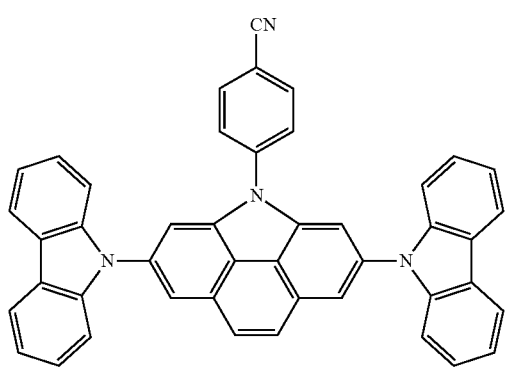
6
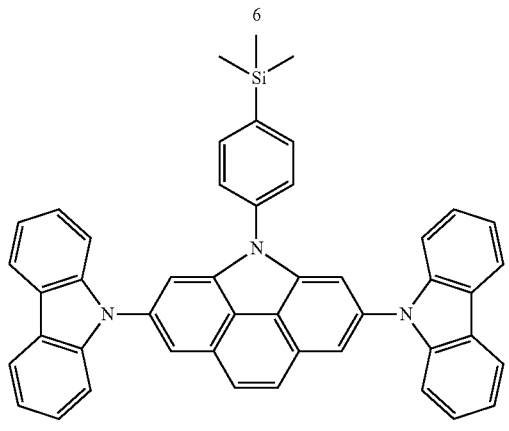
7
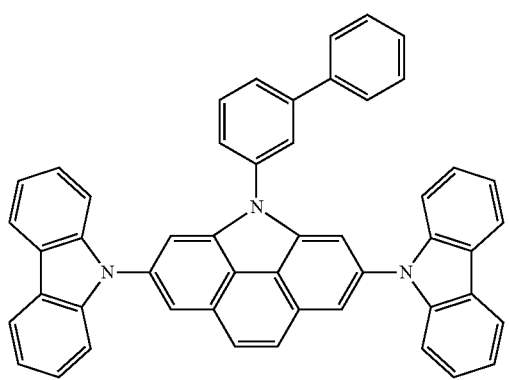
8
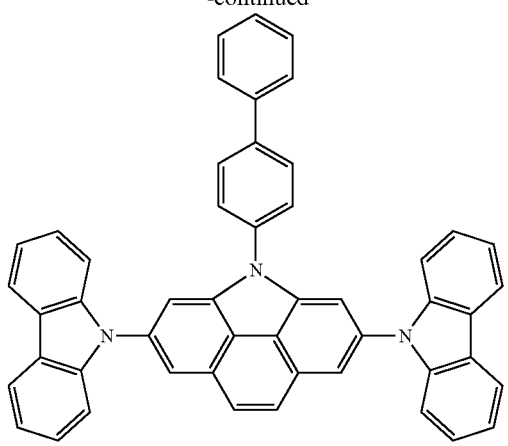

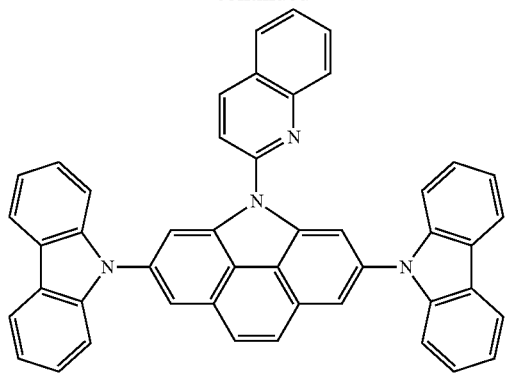
13
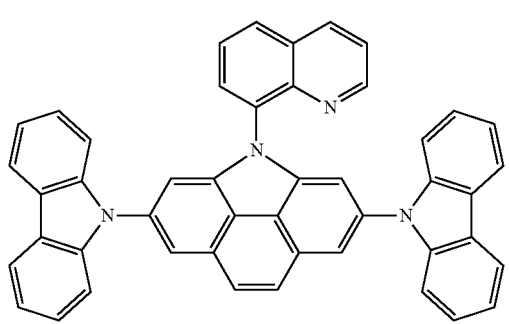
14
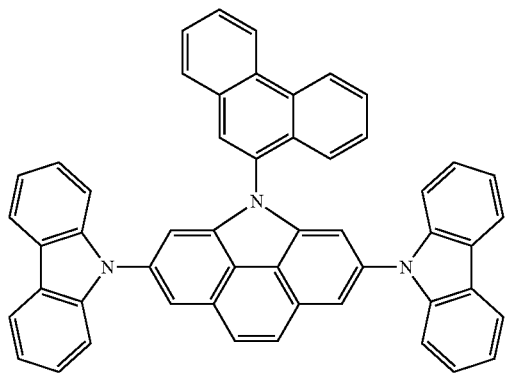
15
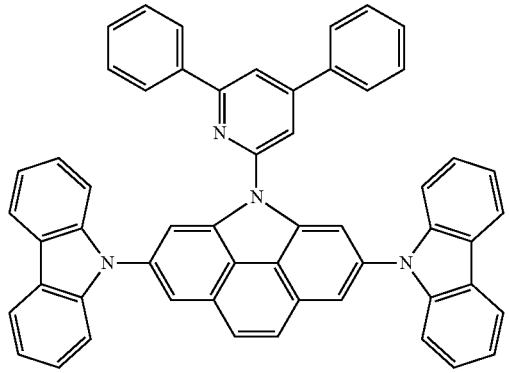
16
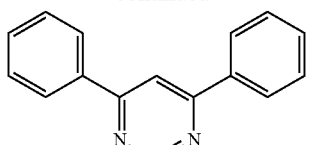
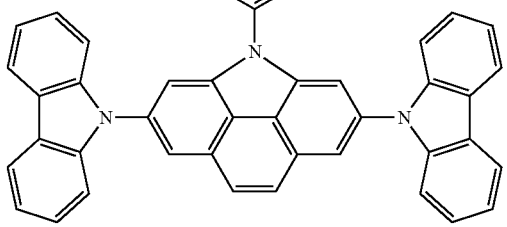
17
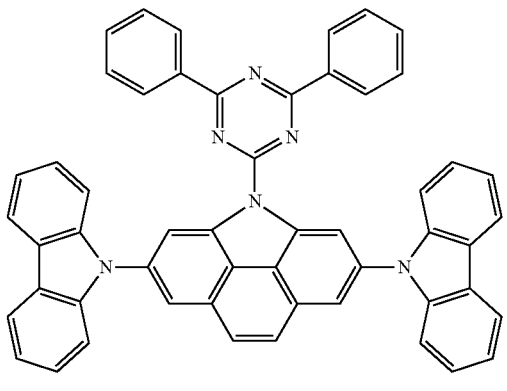
18
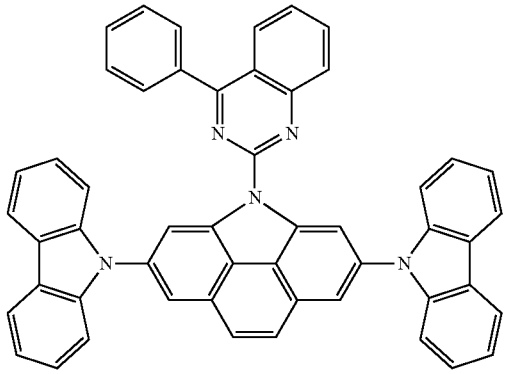
19
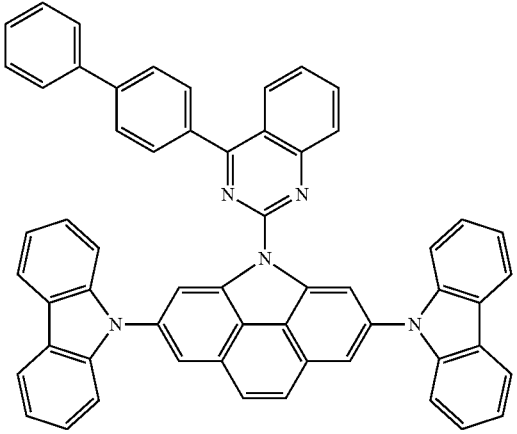
20

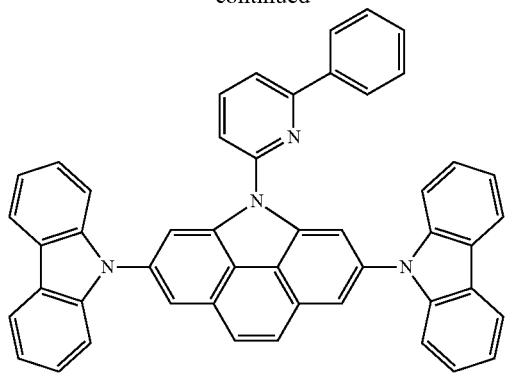
21
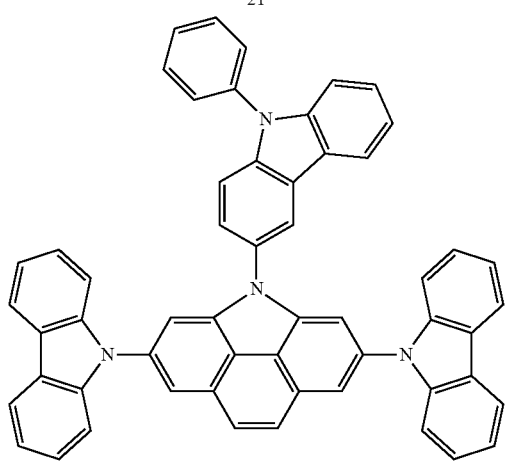
22
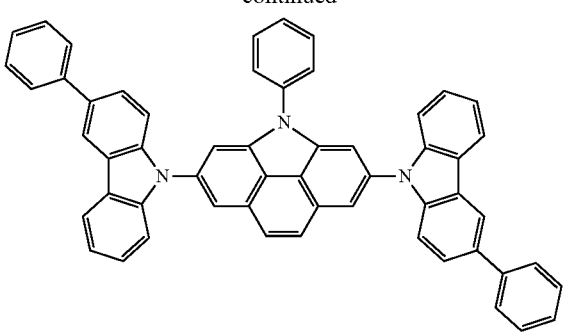
25
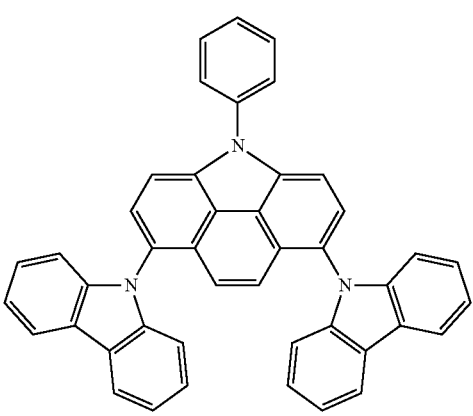
26
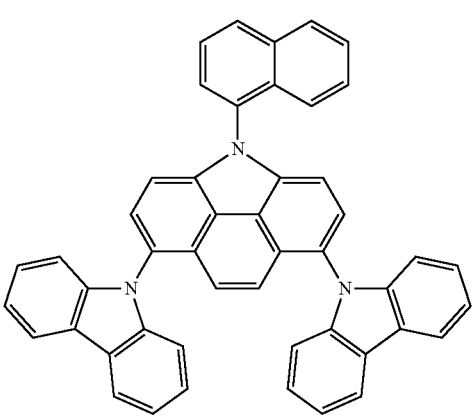
27

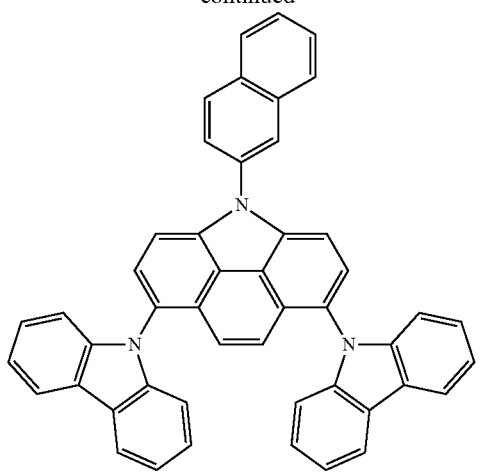
29
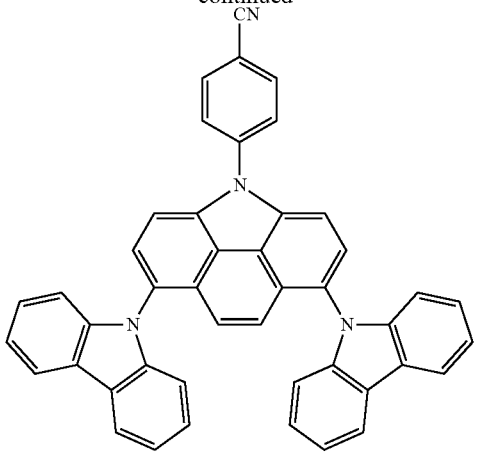
32
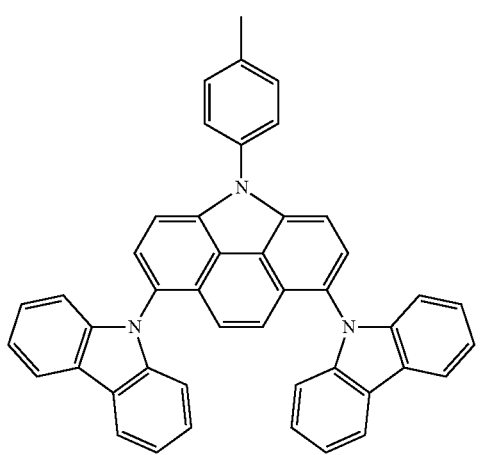
30
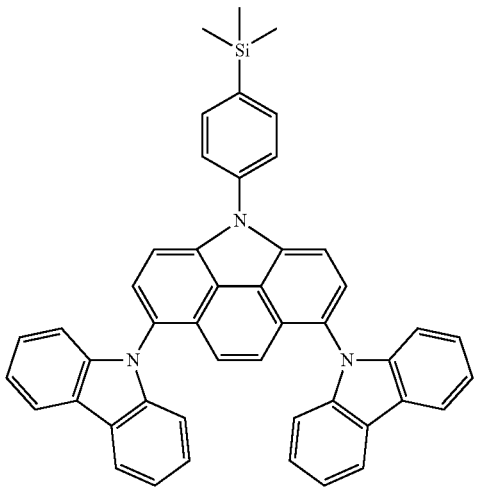
33
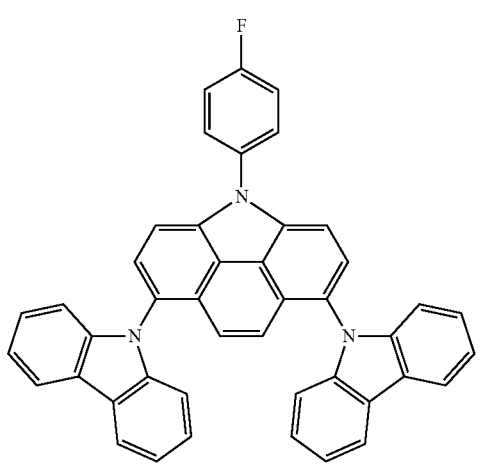
31
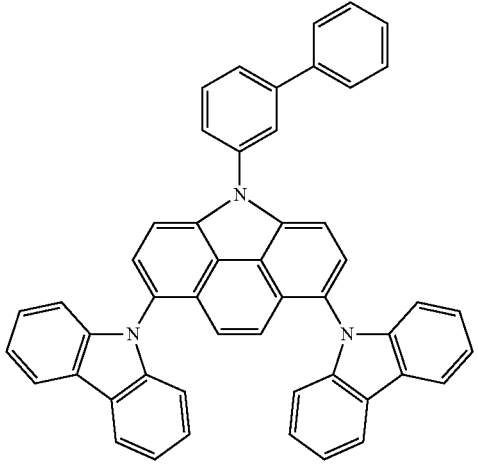
34

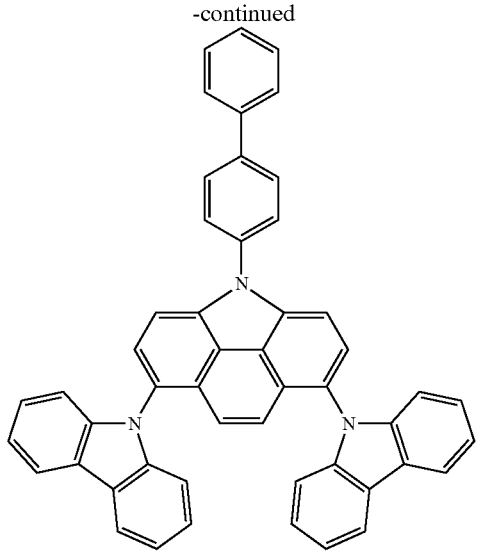
35
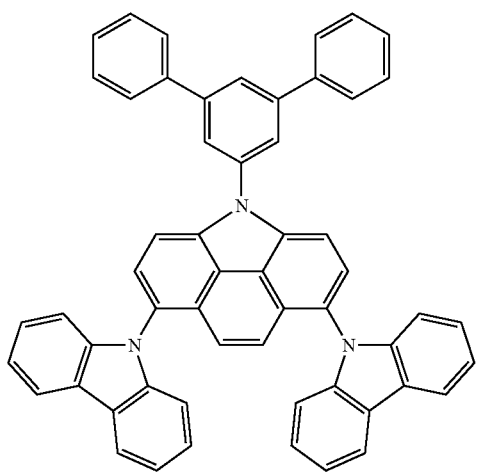
36
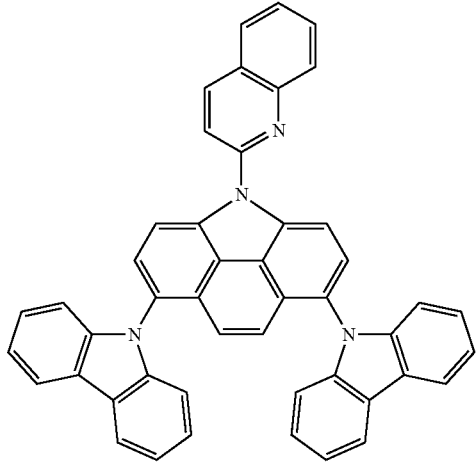
37
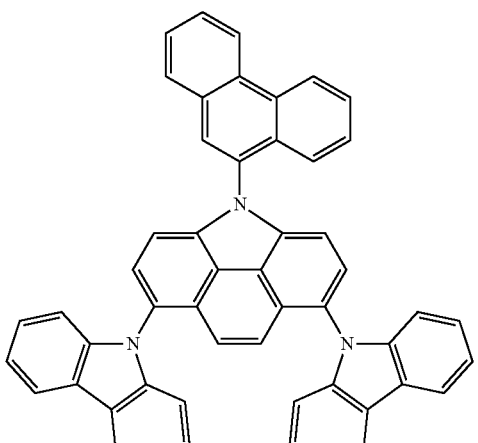
38
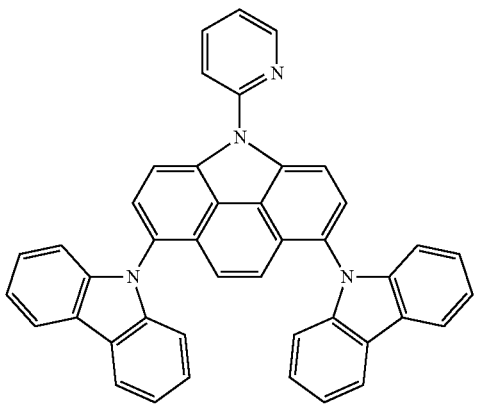
39
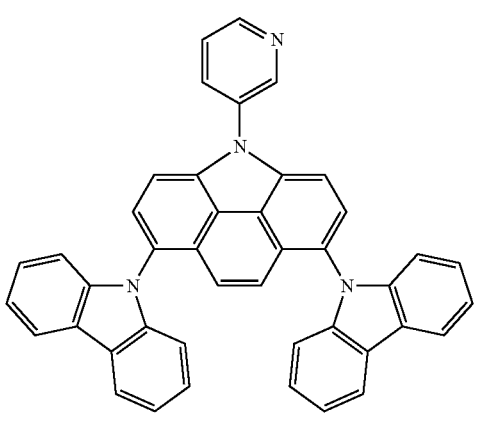
40

-continued
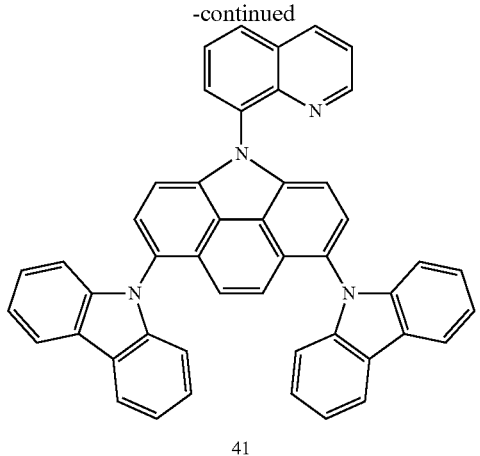
41
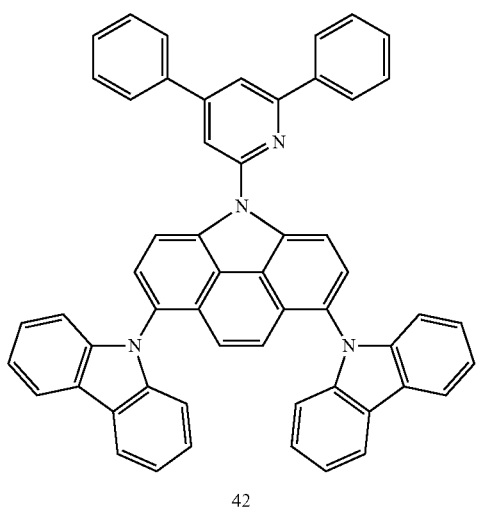
42
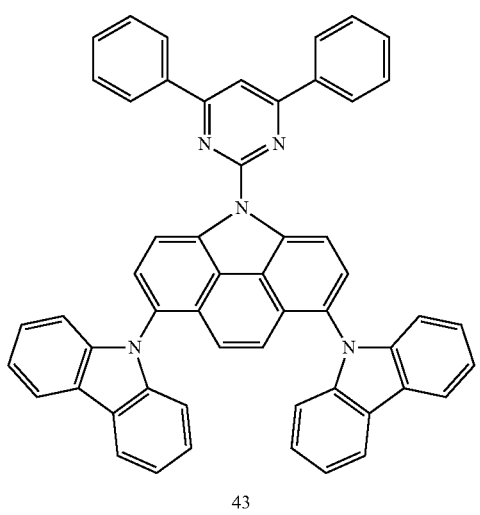
43
-continued
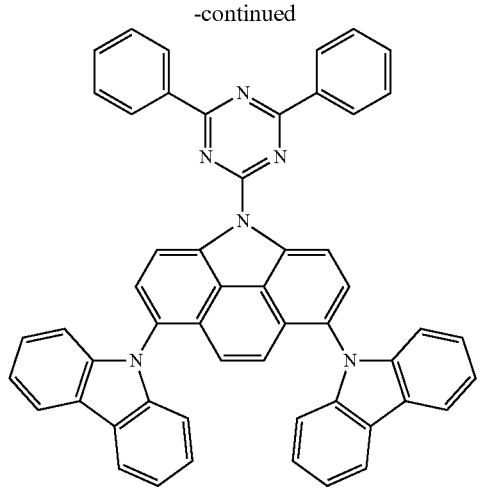
44
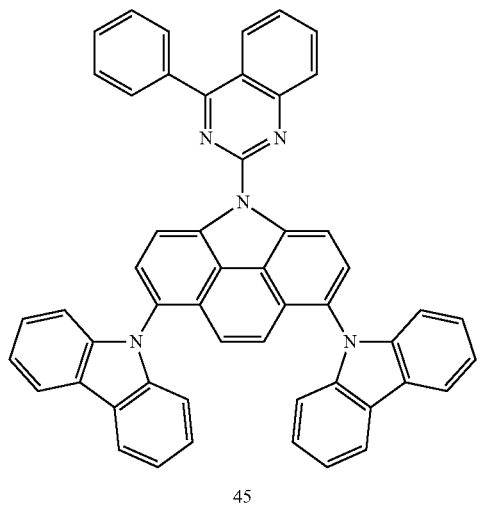
45
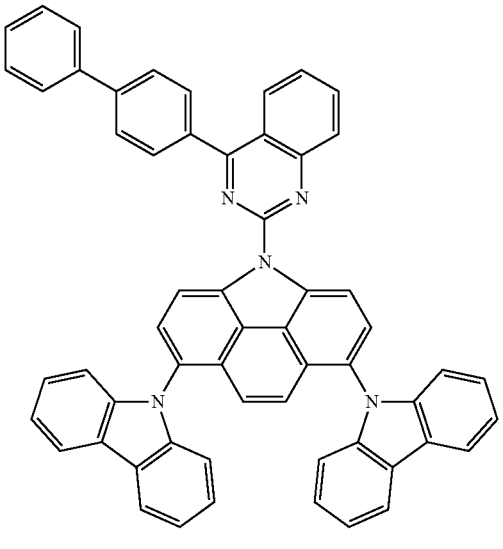
46

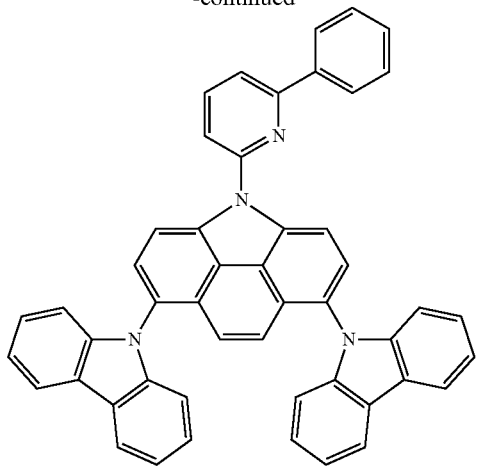
47
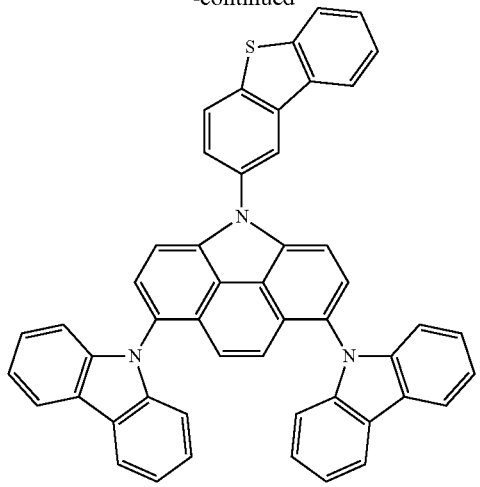
50
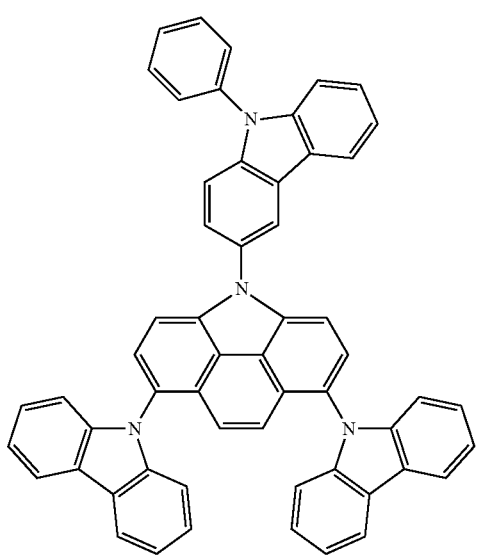
48
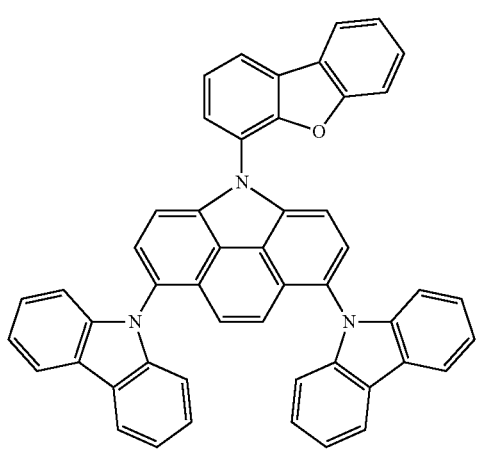
51
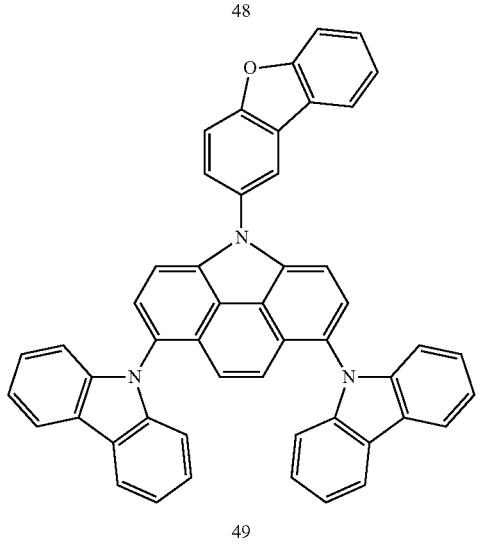
49
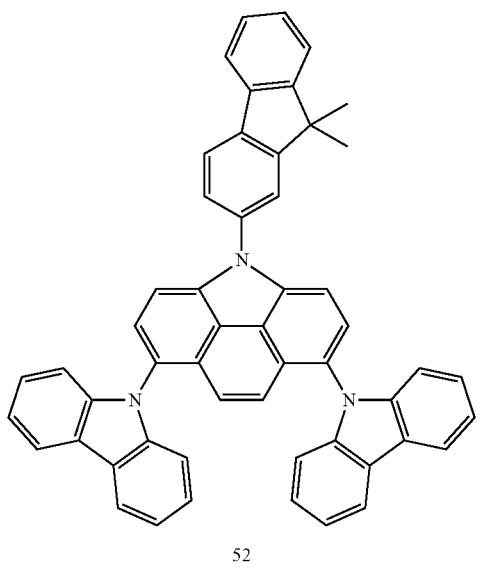
52

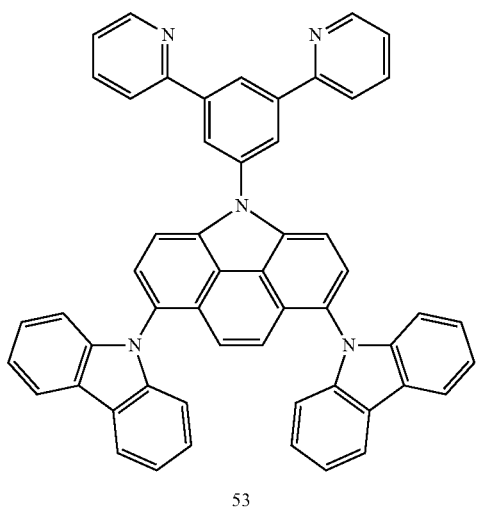

53

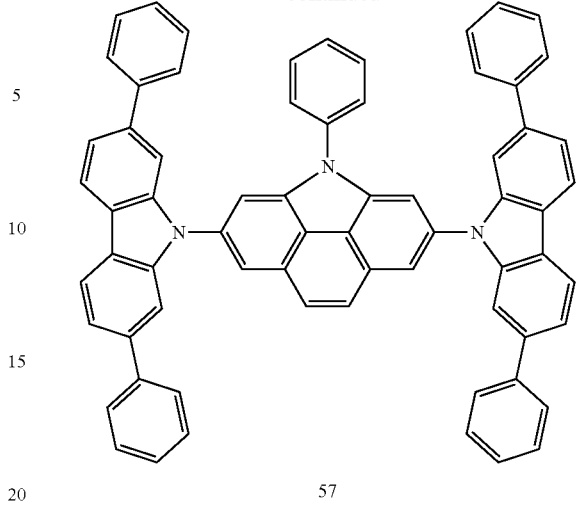

57

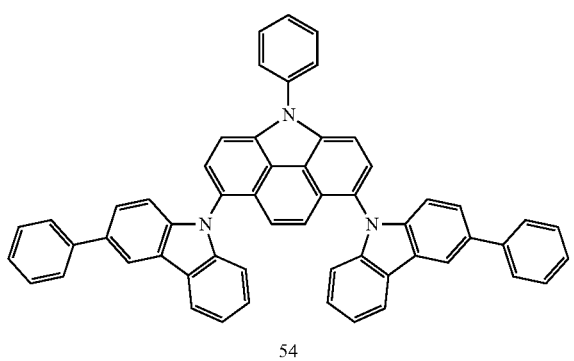

54

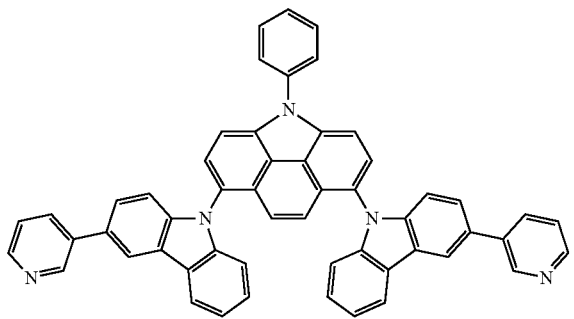

55

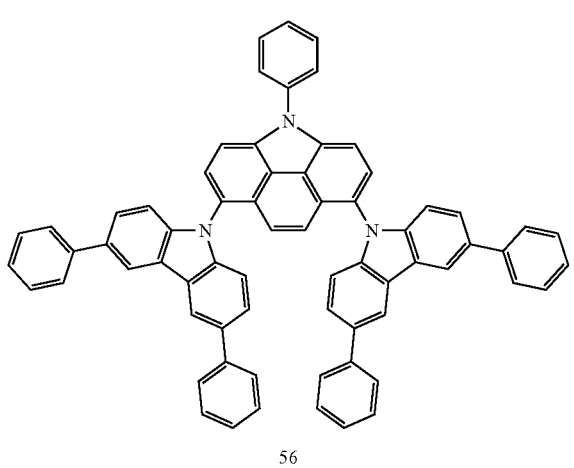

56

An organic light-emitting device according to another embodiment of the present invention includes a first electrode; a second electrode; and an organic layer between the first electrode and the second electrode, where the organic layer includes the compound represented by Formula 1.

The organic layer may include at least one layer of a hole-injecting layer, a hole-transporting layer, a functional layer having both hole injecting and hole transporting capabilities (hereinafter, referred to as an "H-functional layer"), a buffer layer, an electron-blocking layer, an emission layer, a hole-blocking layer, an electron-transporting layer, an electron-injecting layer, or a functional layer having both electron injecting and electron transporting capabilities (hereinafter, referred to as an "E-functional layer").

In greater detail, the organic layer may include the emission layer and the compound may be used (utilized) as a fluorescent host or a phosphorescent host in the emission layer.

According to an embodiment of the present invention, the organic layer includes an electron-injecting layer, an electron-transporting layer, an emission layer, a hole-injecting layer, a hole-transporting layer, or an H-functional layer, where the emission layer may include an anthracene-based compound, an arylamine-based compound, or a styryl-based compound.

According to another embodiment of the present invention, the organic layer includes an electron-injecting layer, an electron-transporting layer, an emission layer, a hole-injecting layer, a hole-transporting layer, and/or an H-functional layer, where the emission layer includes a red layer (e.g., for emitting red light), a green layer (e.g., for emitting green light), a blue layer (e.g., for emitting blue light) and/or a white layer (e.g., for emitting white light), and any one layer of the red layer, the green layer, the blue layer, and the white layer of the emission layer may include a phosphorescent compound, and the hole-injecting layer, the hole-transporting layer, and/or the H-functional layer may include a charge-generating material. The charge-generating material may be a p-dopant, and the p-dopant may be a quinone derivative, a metal oxide, or a cyano group containing compound.

According to another embodiment of the present invention, the organic layer includes an electron-transporting layer, where the electron-transporting layer may include a metal complex. The metal complex may be a lithium (Li) complex.

As used herein, the term "organic layer" refers to a single layer (or sole layer) or a plurality of layers between the first electrode and the second electrode.

In an embodiment, the organic layer includes an emission layer, and the emission layer may include the compound represented by Formula 1. In another embodiment, the organic layer includes at least one of a hole-injecting layer, a hole-transporting layer, or an H-functional layer. At least one of the hole-injecting layer, the hole-transporting layer, or the H-functional layer may include the compound represented by Formula 1.

The compound represented by Formula 1 included in the emission layer may act as a host. For example, the compound may act as a green phosphorescent host emitting green light. Alternatively, the compound may act as a red phosphorescent host emitting red light.

The accompanying drawing is a schematic view of a structure of an organic light-emitting device according to an embodiment of the present invention. Hereinafter, a structure and a method of manufacturing an organic light-emitting device, according to an embodiment of the present invention, will be described with reference to the accompanying drawing.

A substrate may be any suitable substrate that is generally used in organic light-emitting devices. In some embodiments, the substrate may be a glass substrate or a transparent plastic substrate having strong mechanical strength, thermal stability, transparency, surface smoothness, ease of handling, and/or water resistance.

The first electrode may be formed by depositing or sputtering a first electrode-forming material onto a surface of the substrate. When the first electrode is an anode, a material having a high work function may be used as the first electrode-forming material to facilitate hole injection. The first electrode may be a reflective electrode or a transmission electrode (e.g., a transmissive electrode). Transparent and conductive materials, such as indium tin oxide (ITO), indium zinc oxide (IZO), tin oxide ($SnO_2$), and/or zinc oxide (ZnO), may be included in (or used as a material for forming) the first electrode. The first electrode may be formed as a reflective electrode by using magnesium (Mg), aluminum (Al), aluminum-lithium (Al—Li), calcium (Ca), magnesium-indium (Mg—In), magnesium-silver (Mg—Ag), or the like.

The first electrode may have a single layer structure or a multi-layer structure including at least two layers (e.g., a plurality of layers). For example, the first electrode may have a three-layered structure of ITO/Ag/ITO, but the first electrode is not limited thereto.

An organic layer is on the first electrode.

The organic layer may include a hole-injecting layer (HIL), a hole-transporting layer (HTL), a buffer layer, an emission layer (EML), an electron-transporting layer (ETL), and/or an electron-injecting layer (EIL).

The HIL may be formed on the first electrode by various suitable methods, such as vacuum deposition, spin coating, casting, or Langmuir-Blodgett (LB) deposition.

When the HIL is formed using vacuum deposition, vacuum deposition conditions may vary according to a material that is used as the material for forming the HIL, and the desired structure and thermal properties of the HIL to be formed. For example, vacuum deposition may be performed at a temperature of about 100° C. to about 500° C., a pressure of about $10^{-8}$ torr to about $10^{-3}$ torr, and a deposition rate of about 0.01 Å/sec to about 100 Å/sec. However, the deposition conditions are not limited thereto.

When the HIL is formed using spin coating, the coating conditions may vary according to a material that is used as the material for forming the HIL, and the desired structure and thermal properties of the HIL to be formed. For example, the coating rate may be in a range of about 2000 rpm to about 5000 rpm, and a temperature at which heat treatment is performed to remove a solvent after coating may be in a range of about 80° C. to about 200° C. However, the coating conditions are not limited thereto.

A hole-injecting material may be any suitable hole-injecting material generally used in the art. Non-limiting examples of the hole-injecting material include N,N'-diphenyl-N,N'-bis-[4-(phenyl-m-tolyl-amino)-phenyl]-biphenyl-4,4'-diamine (DNTPD), a phthalocyanine compound such as copper phthalocyanine, 4,4',4''-tris(3-methylphenyiphenylamino)triphenylamine (m-MTDATA), N,N'-di(1-naphthyl-N,N'-diphenylbenzidine) (NPB), TDATA, 2-TNATA, polyaniline/dodecylbenzenesulfonic acid (Pani/DBSA), poly(3,4-ethylenedioxythiophene)/poly(4-styrenesulfonate) (PEDOT/PSS), polyaniline/camphor sulfonic acid (Pani/CSA), and (polyaniline)/poly(4-styrenesulfonate (PANI/PSS):

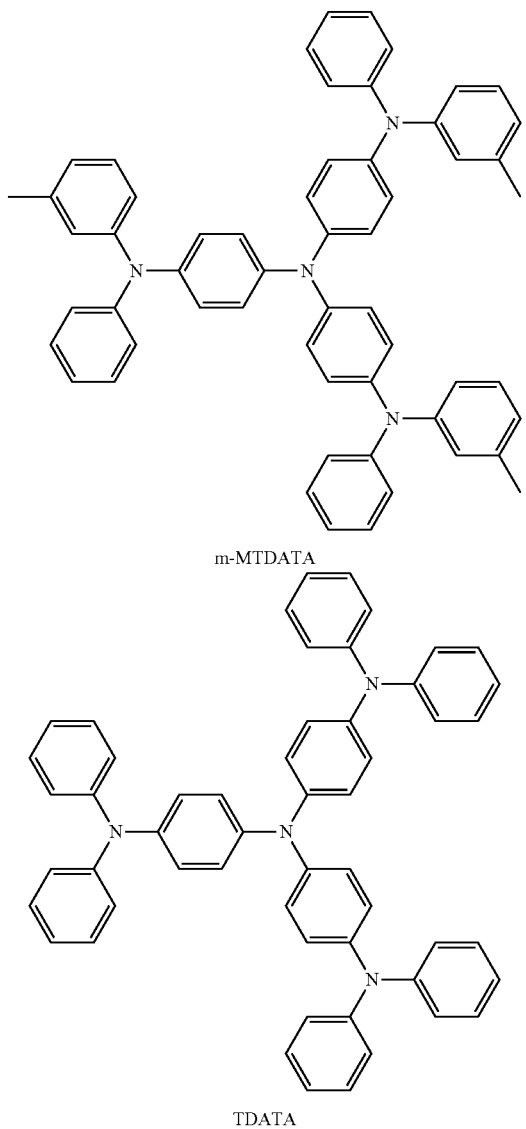

m-MTDATA

TDATA

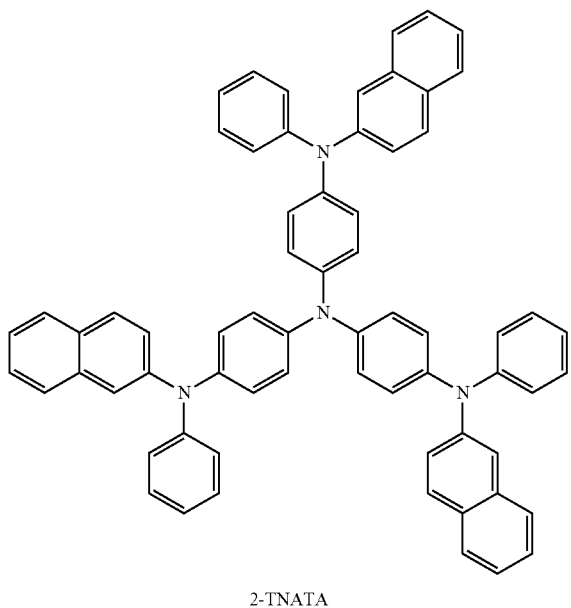

2-TNATA

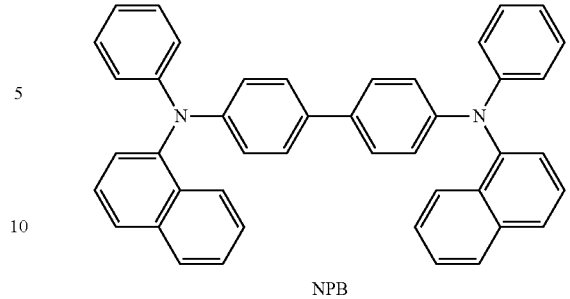

NPB

The thickness of the HIL may be about 100 Å to about 10000 Å, and in some embodiments, may be from about 100 Å to about 1000 Å. When the thickness of the HIL is within any of the foregoing ranges, the HIL may have suitable (or satisfactory) hole-injecting ability without a substantial increase in driving voltage.

Then, the HTL may be formed on the HIL by using vacuum deposition, spin coating, casting, LB deposition, or the like. When the HTL is formed using vacuum deposition or spin coating, the conditions for deposition and coating may be similar to those described above with respect to the formation of the HIL, though the conditions for the deposition and coating may vary according to a compound that is used to form the HTL.

Any suitable material generally used as a hole-transporting material may be used as the hole-transporting material. Non-limiting examples of the hole-transporting material include carbazole derivatives, such as N-phenylcarbazole and polyvinylcarbazole, N,N'-bis(3-methylphenyl)-N,N'-diphenyl-[1,1-biphenyl]-4,4'-diamine (TPD), 4,4',4"-tris(N-carbazolyl)triphenylamine (TCTA), and N,N'-di(1-naphthyl-N,N'-diphenylbenzidine) (NPB).

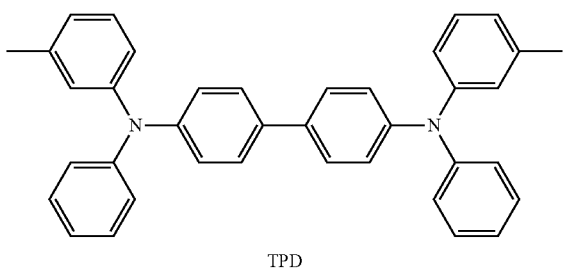

TPD

The thickness of the HTL may be from about 50 Å to about 2000 Å, and in some embodiments, may be from about 100 Å to about 1500 Å. When the thickness of the HTL is within any of the foregoing ranges, the HTL may have suitable (or satisfactory) hole-transporting ability without a substantial increase in driving voltage.

The H-functional layer (having both hole injecting and hole transporting capabilities) may contain one or more materials from each group of the HIL materials and HTL materials described herein. The thickness of the H-functional layer may be from about 100 Å to about 10000 Å, and in some embodiments, may be from about 100 Å to about 1000 Å. When the thickness of the H-functional layer is within any of the foregoing ranges, the H-functional layer may have suitable (or satisfactory) hole injecting and transporting capabilities without a substantial increase in driving voltage.

At least one of the HIL, HTL, or H-functional layer may include at least one of compounds represented by Formula 300 below or compounds represented by Formula 350 below:

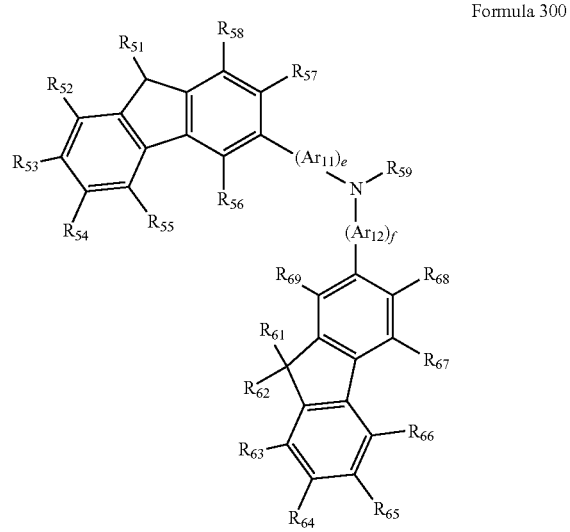

Formula 300

Formula 350 in Formulae 300 and 350, $Ar_{11}$, $Ar_{12}$, $Ar_{21}$, and $Ar_{22}$ are each independently a substituted or unsubstituted $C_6$-$C_{60}$ aryl or arylene group. Descriptions of $Ar_{11}$, $Ar_{12}$, $Ar_{21}$ and $Ar_{22}$ correspond to the description of the $C_6$-$C_{60}$ aryl group above.

In Formula 300, e and f are each independently an integer of 0 to 5, or 0, 1, or 2. For example, e may be 1 and f may be 0, but e and f are not limited thereto.

In Formulae 300 and 350 above, $R_{51}$ to $R_{58}$, $R_{61}$ to $R_{69}$, and $R_{71}$ and $R_{72}$ are each independently a hydrogen atom, a deuterium atom, a halogen atom, a hydroxyl group, a cyano group, a nitro group, an amino group, an amidino group, a hydrazine group, a hydrazone group, a carboxyl group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{60}$ cycloalkyl group, a substituted or unsubstituted $C_5$-$C_{60}$ aryl group, a substituted or unsubstituted $C_5$-$C_{60}$ aryloxy group, or a substituted or unsubstituted $C_5$-$C_{60}$ arylthio group. For example, $R_{51}$ to $R_{58}$, $R_{61}$ to $R_{69}$, and $R_{71}$ and $R_{72}$ may be each independently one of a hydrogen atom; a deuterium atom; a halogen atom; a hydroxyl group; a cyano group; a nitro group; an amino group; an amidino group a; hydrazine group; a hydrazone group; a carboxyl group or a salt thereof; a sulfonic acid group or a salt thereof; a phosphoric acid group or a salt thereof; or a $C_1$-$C_{10}$ alkyl group (for example, a methyl group, an ethyl group, a propyl group, a butyl group, a pentyl group, or a hexyl group);

a $C_1$-$C_{10}$ alkoxy group (for example, a methoxy group, an ethoxy group, a propoxy group, a butoxy group, or a pentoxy group);

a $C_1$-$C_{10}$ alkyl group or a $C_1$-$C_{10}$ alkoxy group each substituted with one or more of a deuterium atom, a halogen atom, a hydroxyl group, a cyano group, a nitro group, an amino group, an amidino group, a hydrazine group, a hydrazone group, a carboxyl group or a salt thereof, a sulfonic acid group or a salt thereof, or a phosphoric acid group or a salt thereof;

a phenyl group; a naphthyl group; an anthryl group; a fluorenyl group; or a pyrenyl group; or a phenyl group, a naphthyl group, an anthryl group, a fluorenyl group, or a pyrenyl group, each substituted with one or more of a deuterium atom, a halogen atom, a hydroxyl group, a cyano group, a nitro group, an amino group, an amidino group, a hydrazine group, a hydrazone group, a carboxyl group or a salt thereof, a sulfonic acid group or a salt thereof, a phosphoric acid group or a salt thereof, a $C_1$-$C_{10}$ alkyl group, or a $C_1$-$C_{10}$ alkoxy group, but $R_{51}$ to $R_{58}$, $R_{61}$ to $R_{69}$, and $R_{71}$ and $R_{72}$ are not limited thereto.

In Formula 300, $R_{59}$ may be one of a phenyl group; a naphthyl group; an anthryl group; a biphenyl group; or a pyridyl group; or a phenyl group, a naphthyl group, an anthryl group, a biphenyl group, or a pyridyl group, each substituted with one or more of a deuterium atom, a halogen atom, a hydroxyl group, a cyano group, a nitro group, an amino group, an amidino group, a hydrazine group, a hydrazone group, a carboxyl group or a salt thereof, a sulfonic acid group or a salt thereof, a phosphoric acid group or a salt thereof, a substituted or unsubstituted $C_1$-$C_{20}$ alkyl group, or a substituted or unsubstituted $C_1$-$C_{20}$ alkoxy group.

According to an embodiment, a compound represented by Formula 300 above may be represented by Formula 300A below, but it is not limited thereto:

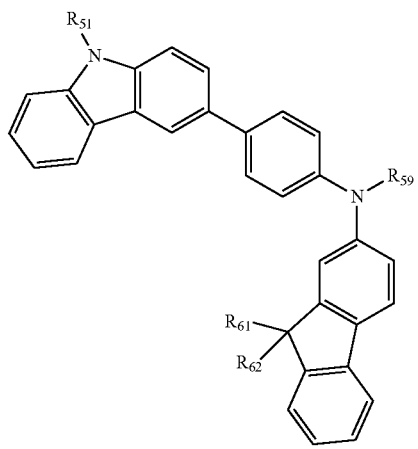

Formula 300A

In Formula 300A, detailed descriptions of $R_{51}$, $R_{61}$, $R_{62}$, and $R_{59}$ are the same as described above with respect to Formula 300.

For example, at least one of the HIL, HTL, or H-functional layer may include one or more of the compounds 301 to 320 below, but the present disclosure is not limited thereto:

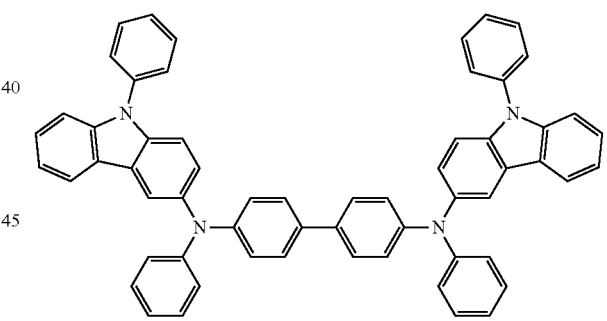

301

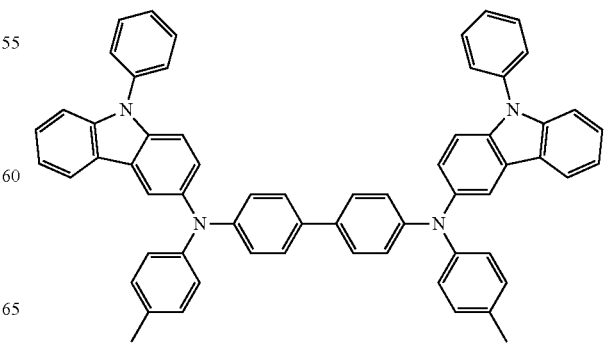

302

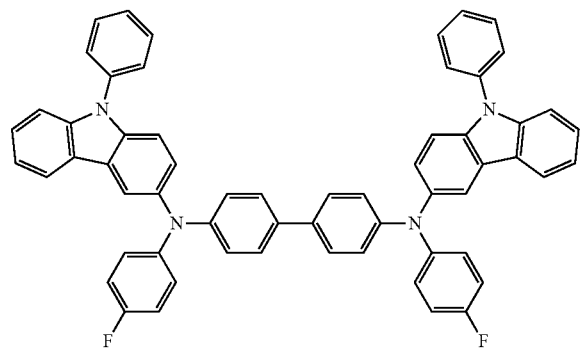
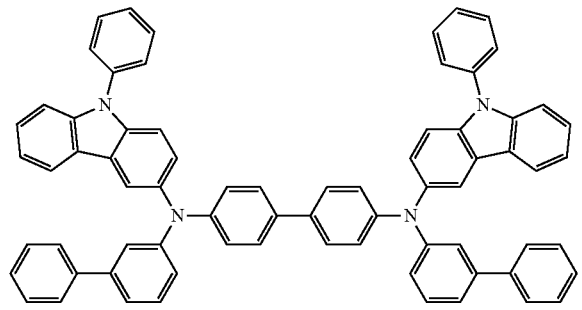
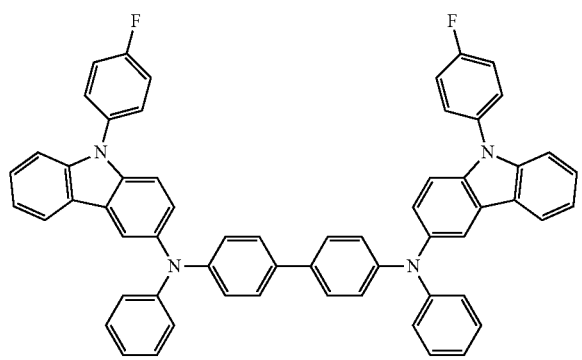
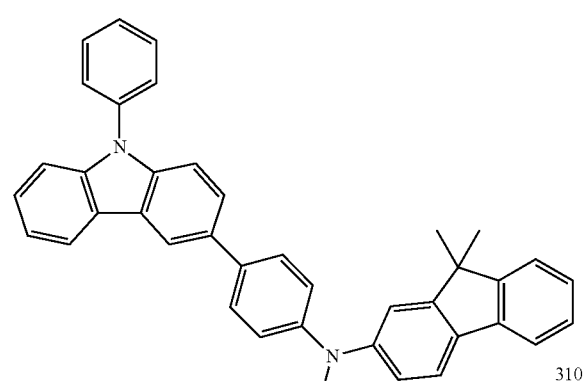
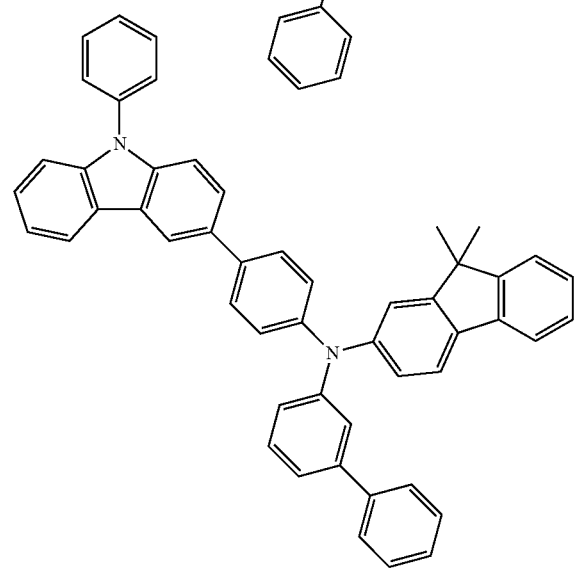

311
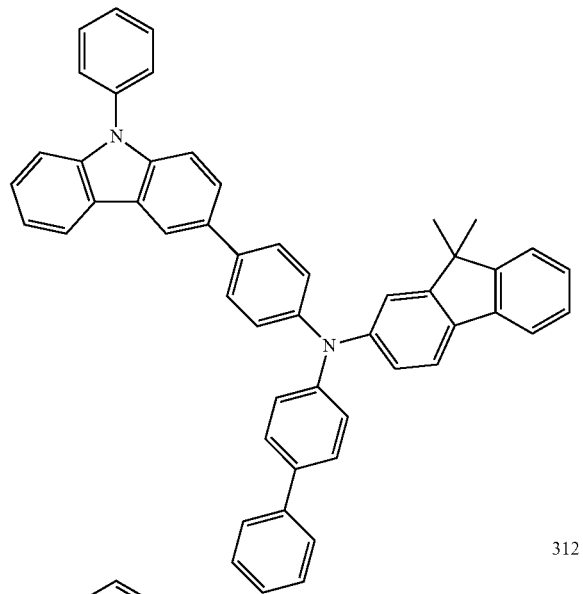
312
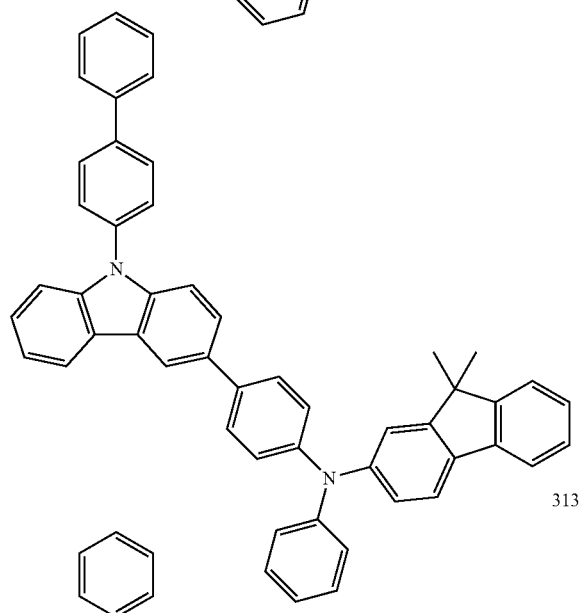
313
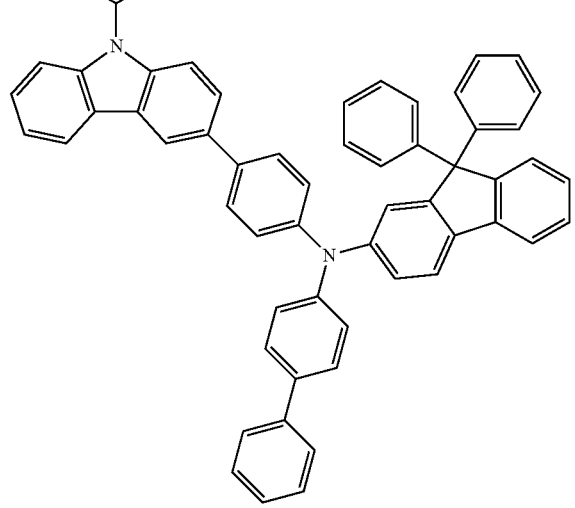
314
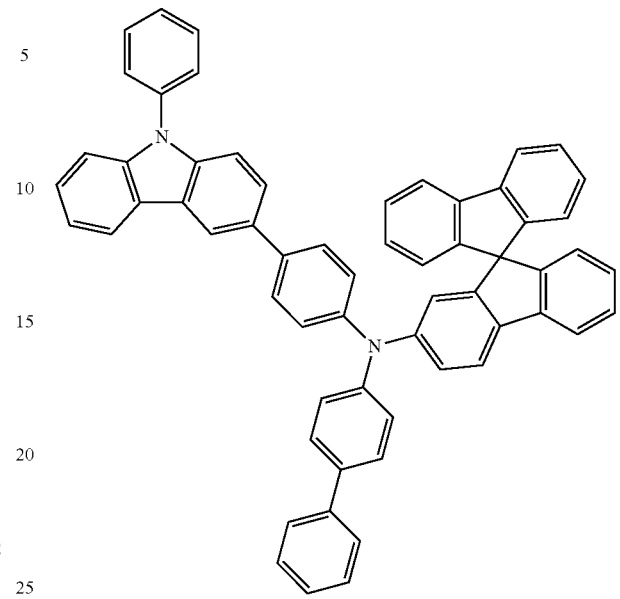
315
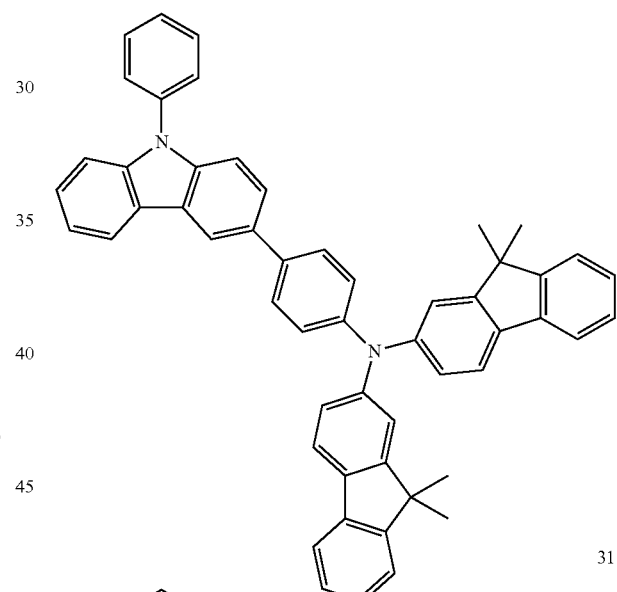
316
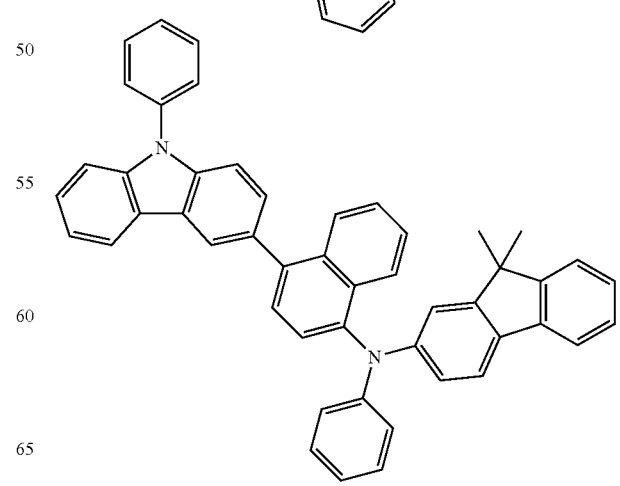

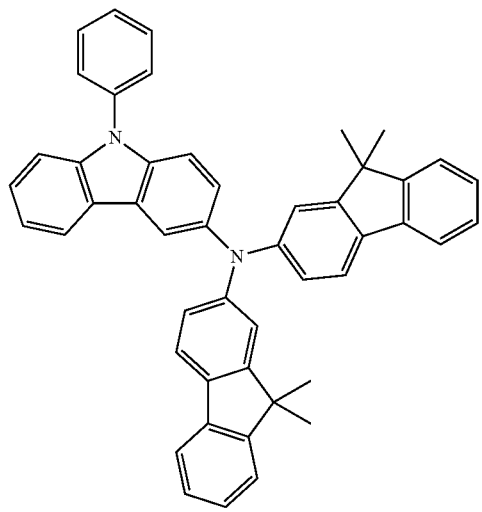

317

318

319

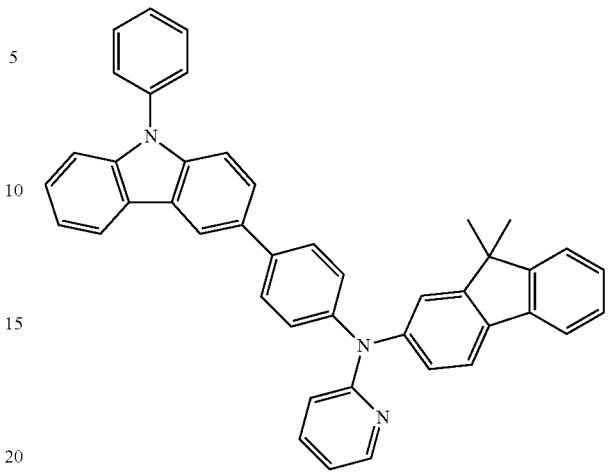

320

To improve conductivity of a film and the like including the HIL, HTL and/or H-functional layer, at least one of the HIL, HTL, or H-functional layer may further include a charge-generating material in addition to the hole-injecting material, hole-transporting material and/or material having both hole injecting and hole transporting capabilities.

The charge-generating material may be, for example, a p-dopant. The p-dopant may be one of a quinone derivative, a metal oxide, and/or a cyano group containing compound, but the p-dopant is not limited thereto. Non-limiting examples of the p-dopant include quinone derivatives, such as tetracyanoquinonedimethane (TCNQ) and 2,3,5,6-tetrafluoro-tetracyano-1,4-benzoquinonedimethane (F4-TCNQ); metal oxides, such as tungsten oxide and molybdenum oxide; and cyano-containing compounds, such as Compound 200 below.

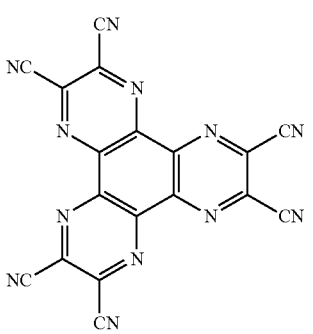

Compound 200

F4-TCNQ

When the HIL, the HTL, or the H-functional layer further include the charge-generating material, the charge-generating material may be included in many different ways. For example, the charge-generating material may be homogeneously dispersed or inhomogeneously distributed in the hole-injecting layer, hole-transporting layer, or H-functional layer.

The buffer layer may be between the EML and at least one of the HIL, HTL, or H-functional layer. The buffer layer may compensate for an optical resonance distance of light according to a wavelength of the light emitted from the EML, and thus may increase efficiency of a device including the buffer layer. The buffer layer may include any hole-injecting material or hole-transporting material that is generally used in the art. In some other embodiments, the buffer layer may include the same material as one of the materials included in the HIL, HTL, and H-functional layer that underlie the buffer layer.

The EML may be formed on the HTL, H-functional layer, or buffer layer by vacuum deposition, spin coating, casting, LB deposition, or the like. When the EML is formed by using vacuum deposition or spin coating, the deposition and coating conditions may be similar to those described above with respect to the formation of the HIL, though the conditions for deposition and coating may vary according to a compound that is used to form the EML.

The EML may include the compound according to an embodiment of the present invention. For example, the compound represented by Formula 1 may be included in the EML as a host. For example, in addition to the compound represented by Formula 1, the EML may include (or be formed by using) various suitable emission materials or hosts and dopants generally used in the art. The dopant may be a fluorescent or phosphorescent dopant generally used in the art.

For example, non-limiting examples of the host include $Alq_3$, 4,4'-N,N'-dicarbazole-biphenyl (CBP), poly(n-vinyl carbazole) (PVK), 9,10-di(naphthalene-2-yl)anthracene (ADN), TCTA, 1,3,5-tris(N-phenylbenzimidazole-2-yl)benzene (TPBI), 3-tert-butyl-9,10-di(naphth-2-yl) anthracene (TBADN), E3, distyryl arylene (DSA), dmCBP, and Compounds 501 to 509, but the host is not limited thereto.

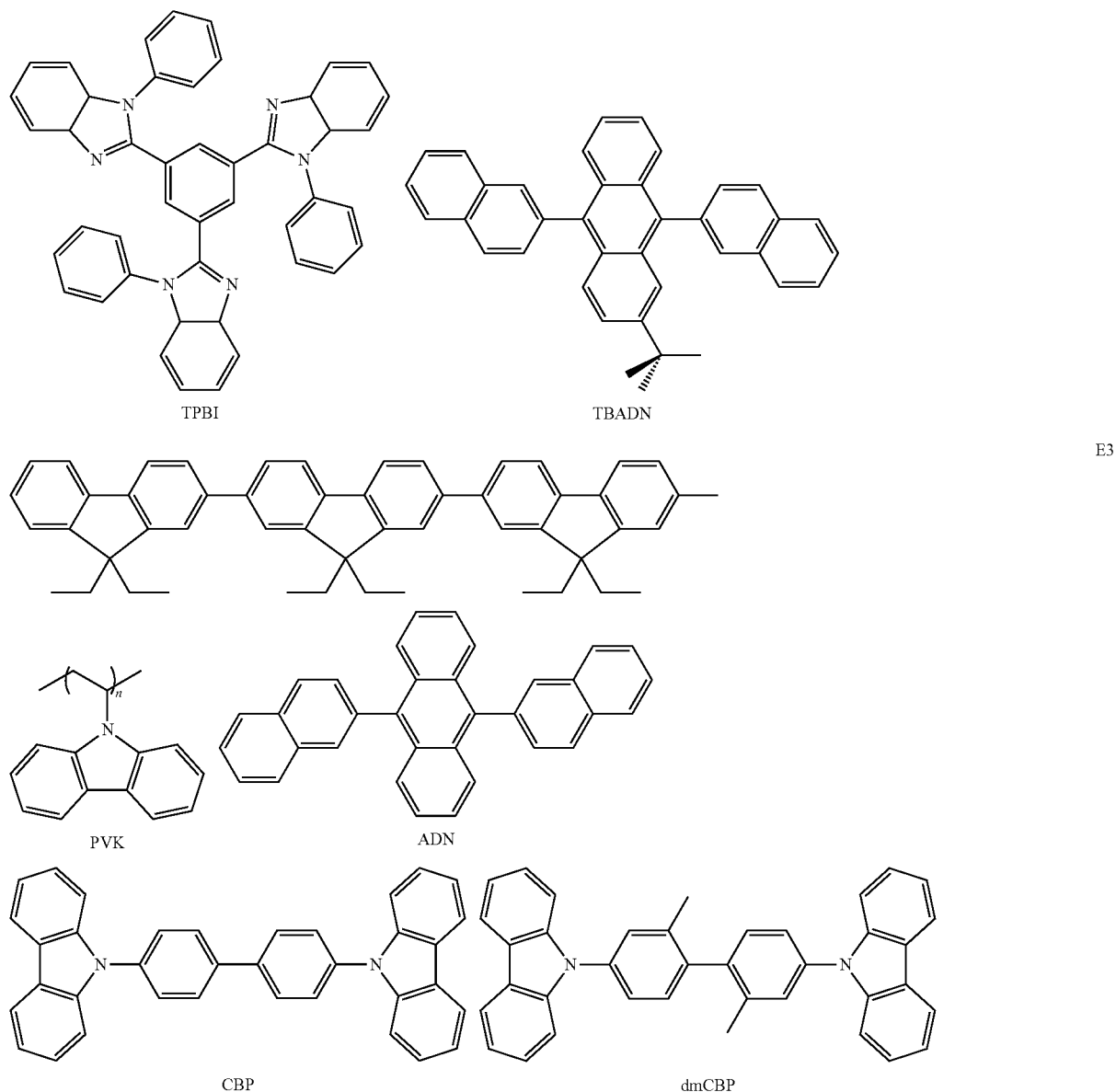

-continued
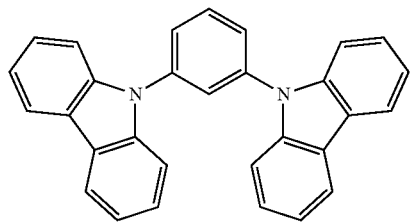
501
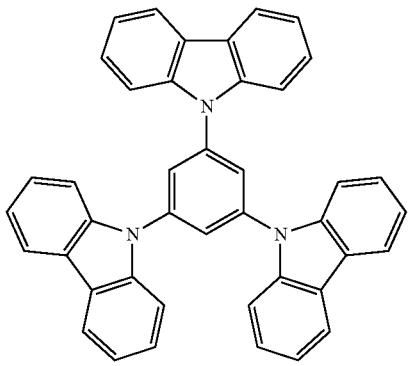
502
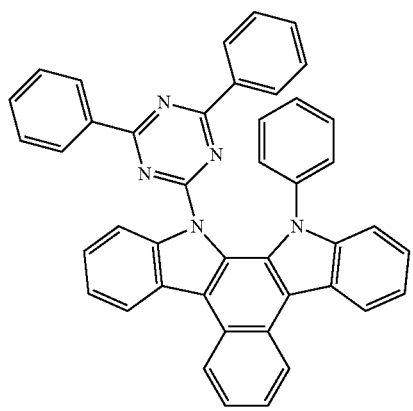
503
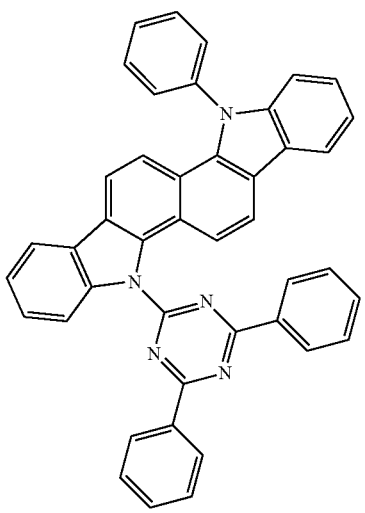
504
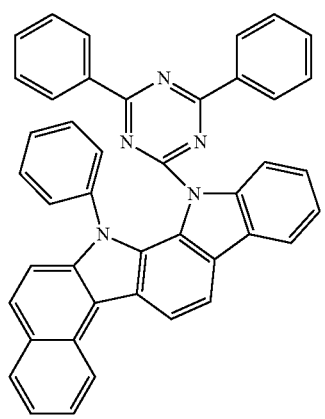
505
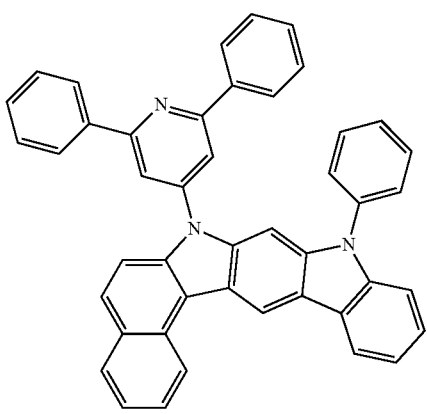
506

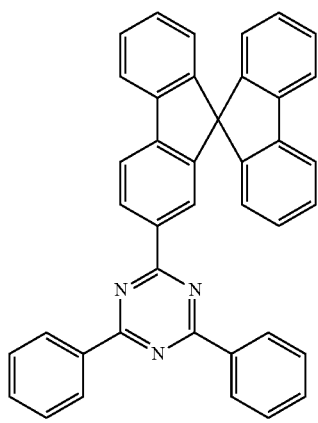
507

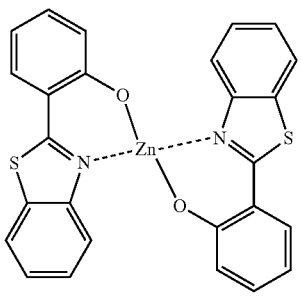
508

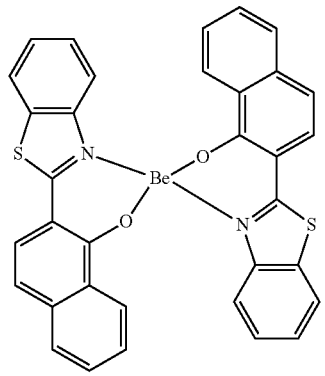
509

Alternatively, or in addition to, as the host, an anthracene-based compound represented by Formula 400 below may be used:

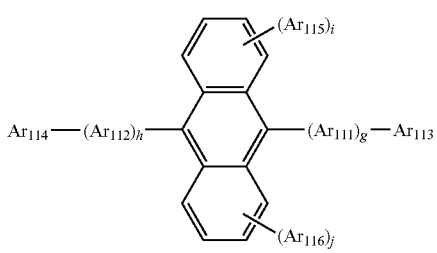
Formula 400

In Formula 400, $Ar_{111}$ and $Ar_{112}$ may be each independently a substituted or unsubstituted $C_5$-$C_{60}$ arylene group; $Ar_{113}$ to $Ar_{116}$ may be each independently a substituted or unsubstituted $C_1$-$C_{10}$ alkyl group or a substituted or unsubstituted $C_5$-$C_{60}$ aryl group; and g, h, i, and j may be each independently an integer of 0 to 4.

For example, in Formula 400 above, $Ar_{111}$ and $Ar_{112}$ may be a phenylene group, a naphthylene group, a phenanthrenylene group, or a pyrenylene group; or a phenylene group, a naphthylene group, a phenanthrenylene group, a fluorenyl group, or a pyrenylene group, each substituted with one or more of a phenyl group, a naphthyl group, and an anthryl group, but $Ar_{111}$ and $Ar_{112}$ are not limited thereto.

In Formula 400 above, g, h, i, and j may be each independently, 0, 1, or 2.

In Formula 400 above, $Ar_{113}$ to $Ar_{116}$ may be each independently a $C_1$-$C_{10}$ alkyl group substituted with one or more of a phenyl group, a naphthyl group, or an anthryl group;

a phenyl group; a naphthyl group; an anthryl group; a pyrenyl group; a phenanthrenyl group; or a fluorenyl group; or a phenyl group, a naphthyl group, an anthryl group, a pyrenyl group, a phenanthrenyl group, or a fluorenyl group, each substituted with one or more of a deuterium atom, a halogen atom, a hydroxyl group, a cyano group, a nitro group, an amino group, an amidino group, a hydrazine group, a hydrazone group, a carboxyl group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a phenyl group, a naphthyl group, an anthryl group, a pyrenyl group, a phenanthrenyl group, or a fluorenyl group; or

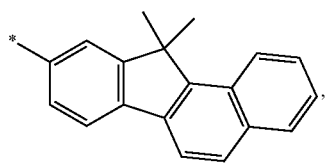 [SMILES: *c1ccc2c(c1)C(C)(C)c1c-2ccc2ccccc12]

but $Ar_{113}$ to $Ar_{116}$ are not limited thereto.

For example, an anthracene-based compound represented by Formula 400 above may be any one of the following compounds, but the anthracene-based compound represented by Formula 400 is not limited thereto:

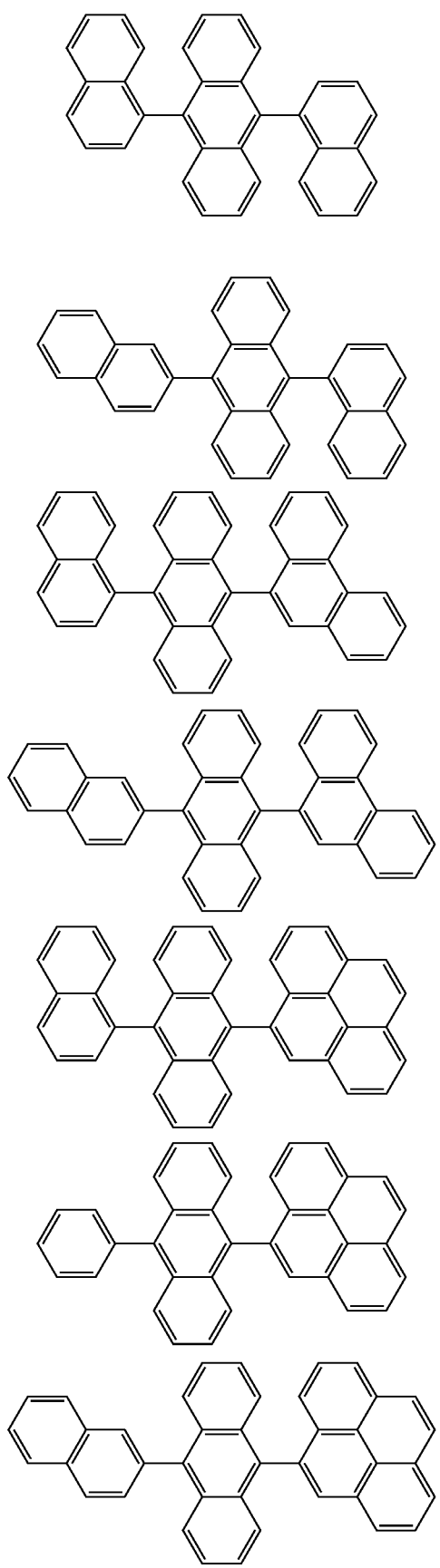
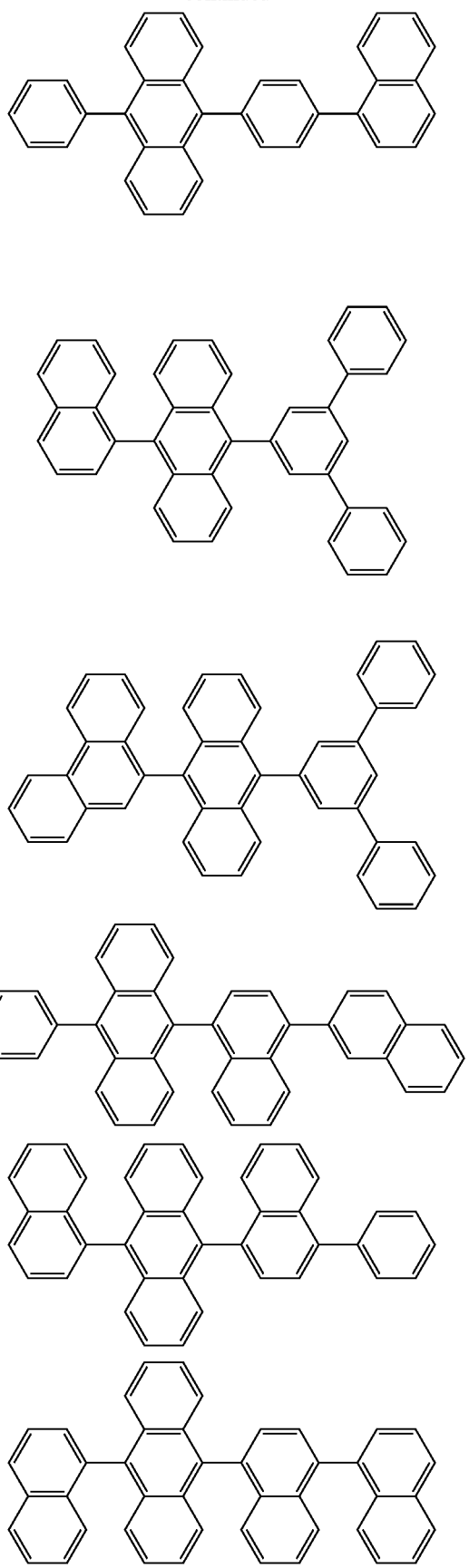

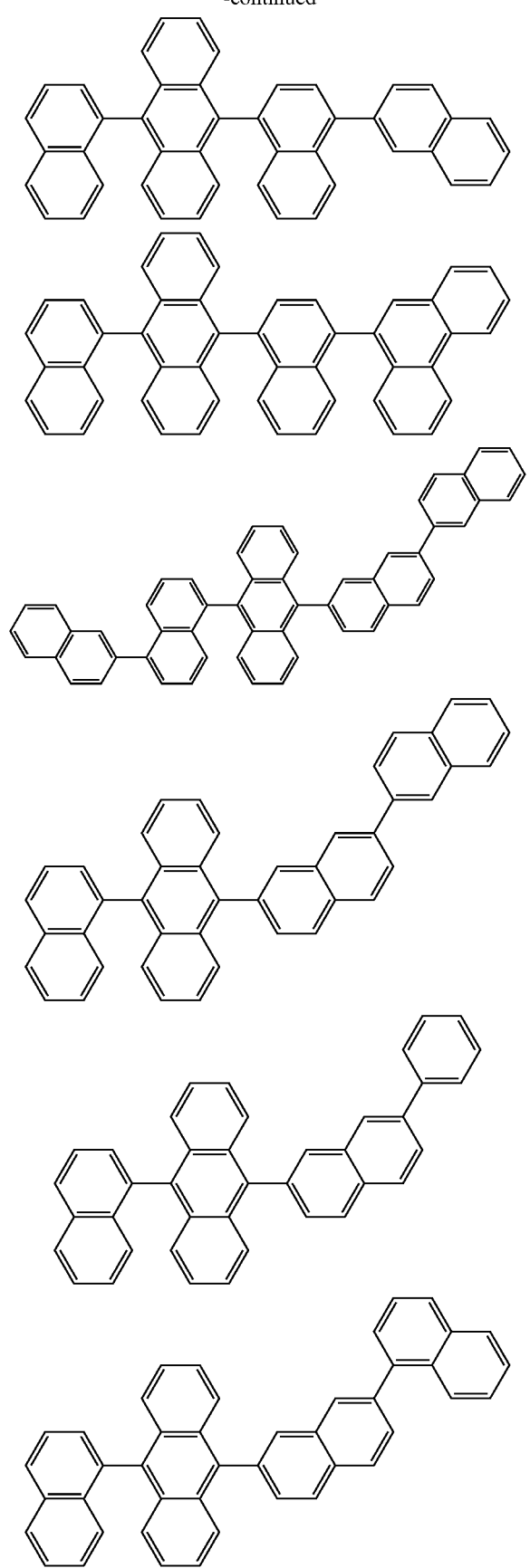
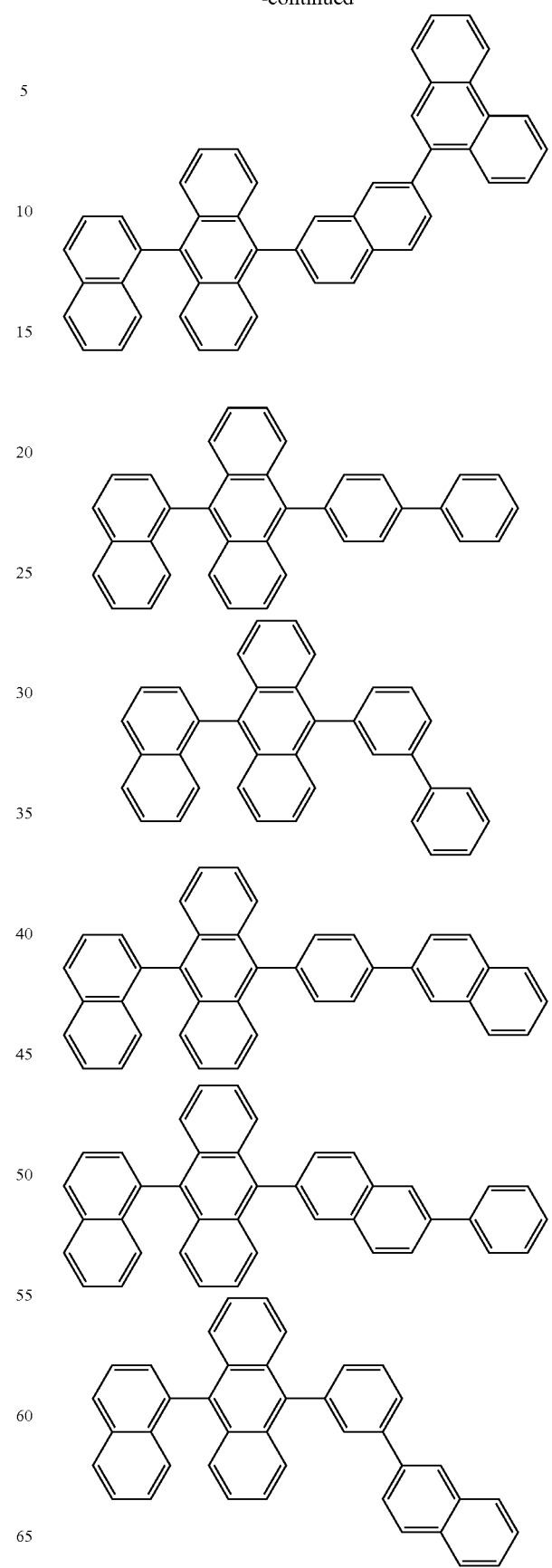

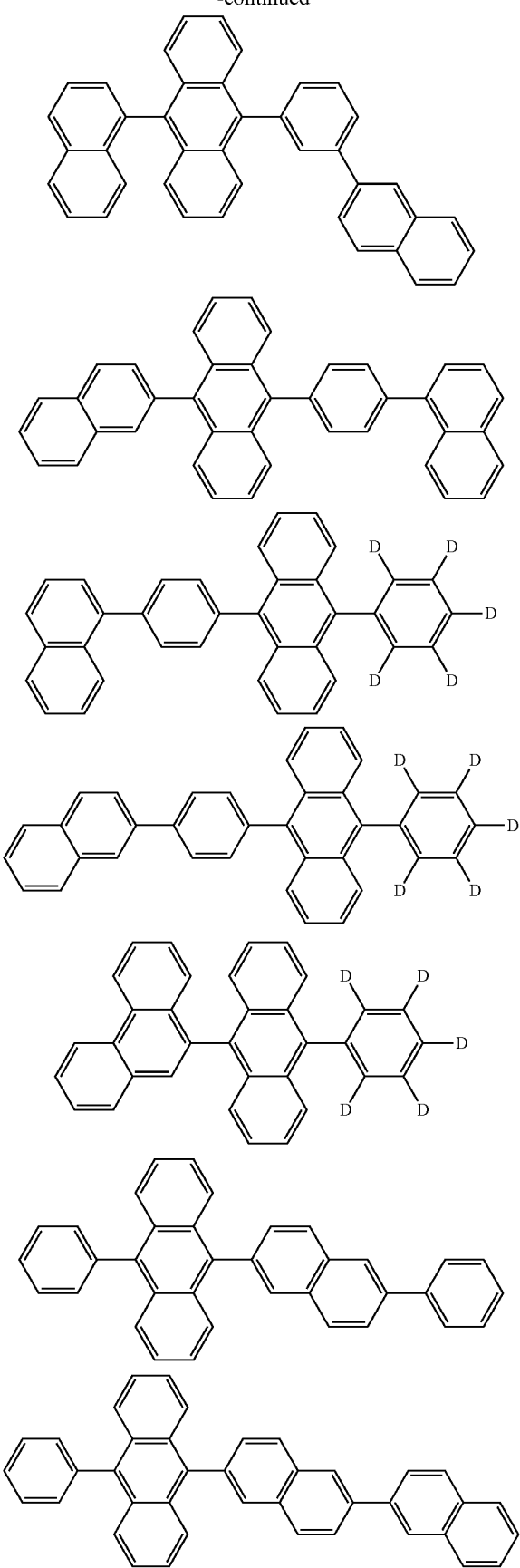
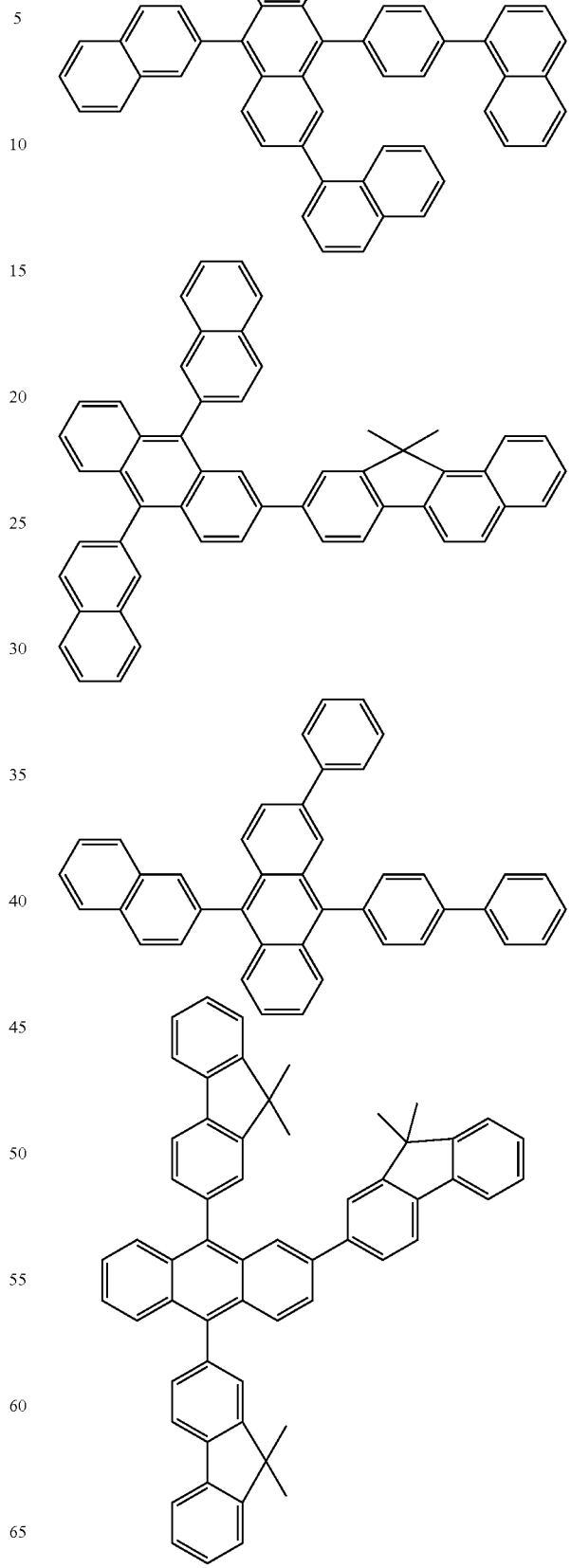

-continued

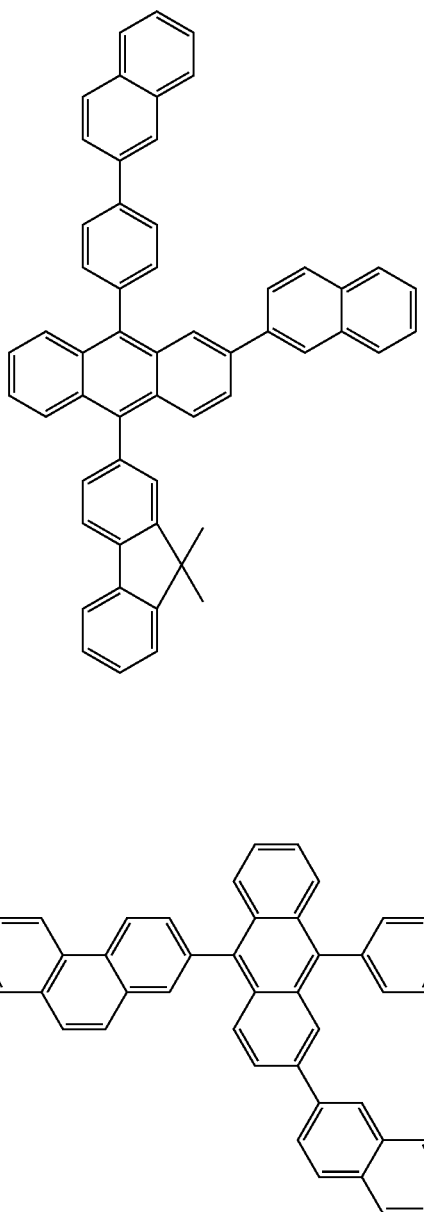

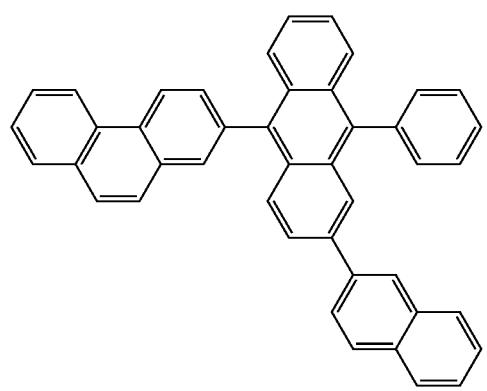 [SMILES: c1ccc(-c2c3ccccc3c(-c3ccc4c(ccc5ccccc54)c3)c3ccc(-c4ccc5ccccc5c4)cc23)cc1]

In another embodiment, as the host, an anthracene-based compound represented by Formula 401 may be used:

Formula 401

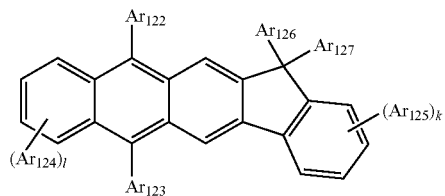

In Formula 401 above, detailed descriptions of $Ar_{122}$ to $Ar_{125}$ are the same as the above description of $Ar_{113}$ with respect to Formula 400.

In Formula 401 above, $Ar_{126}$ and $Ar_{127}$ are each independently a $C_1$-$C_{10}$ alkyl group (for example, a methyl group, an ethyl group, or a propyl group).

In Formula 401, k and l may be each independently an integer of 0 to 4. For example, k and l may be each independently an integer of 0, 1, or 2.

For example, the anthracene-based compound represented by Formula 401 above may be any one of the compounds below, but the anthracene-based compound represented by Formula 401 is not limited thereto:

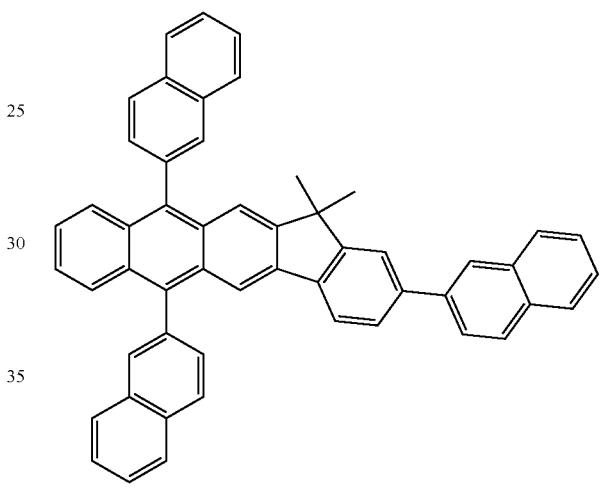

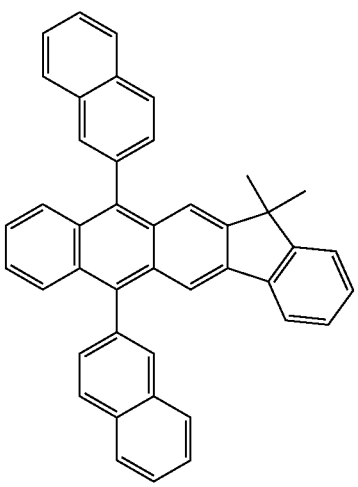

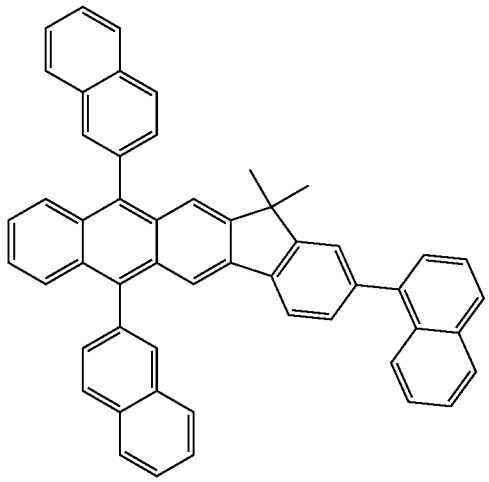

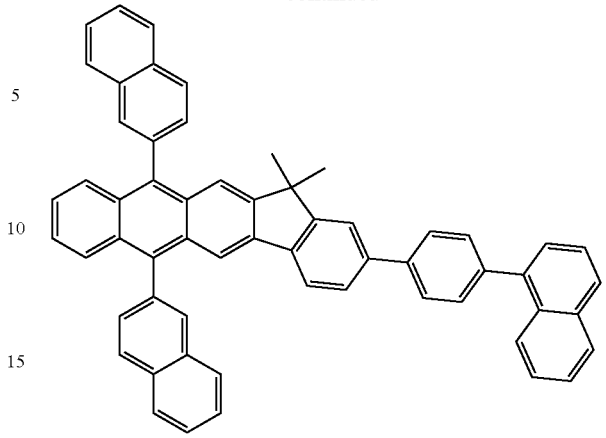

When the organic light-emitting device is a full color organic light-emitting device, the EML may include (e.g., be patterned into) a red EML, a green EML, and a blue EML.

At least one of the red EML, the green EML, or the blue EML may include any one of the dopants shown below, for which ppy=phenylpyridine.

For example, any one of the compounds shown below may be used as the blue dopant, but the blue dopant is not limited thereto.

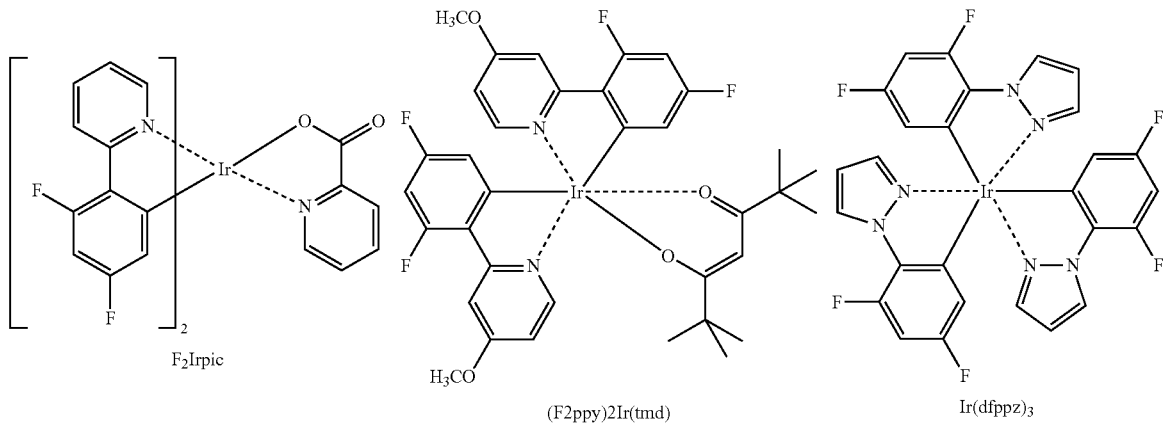

F₂Irpic    (F2ppy)2Ir(tmd)    Ir(dfppz)₃

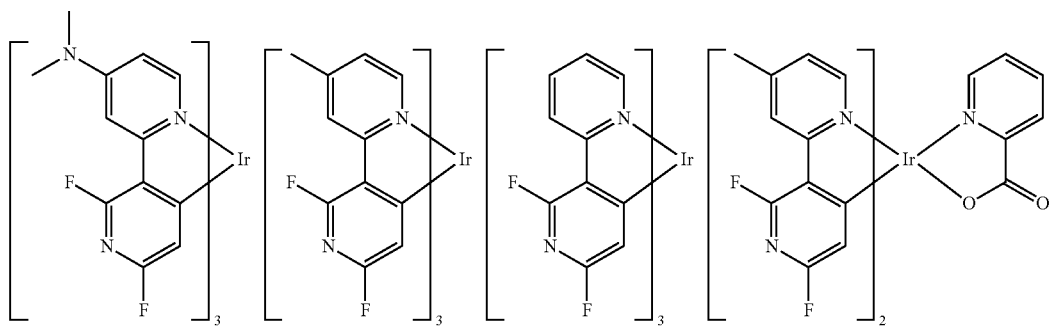

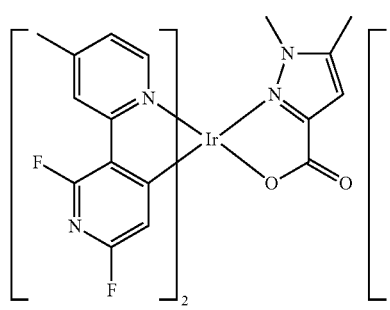
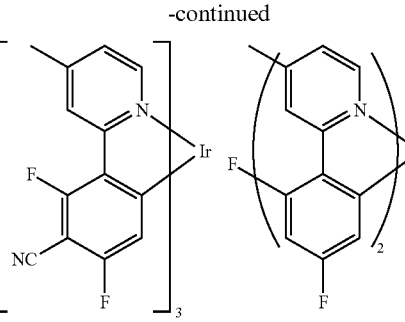
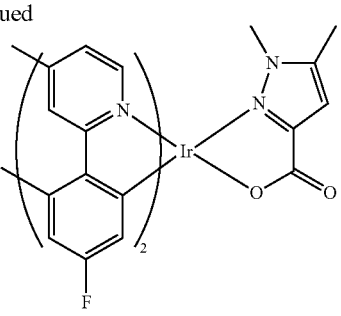
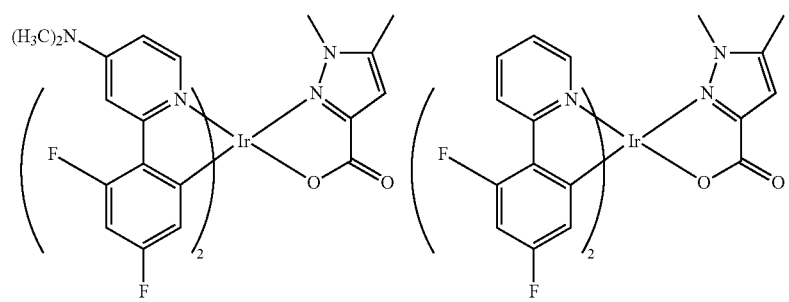
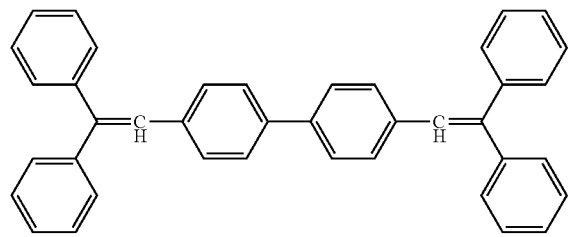
DPVBi
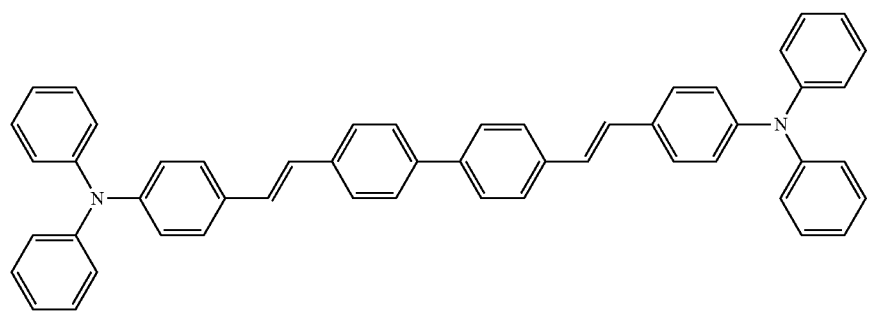
DPAVBi

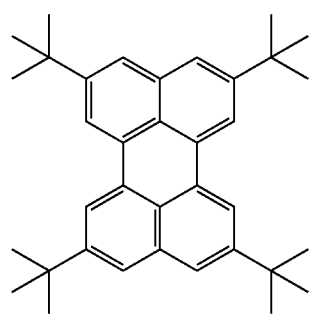
TBPe
For example, any one of the compounds shown below may be used as the red dopant, but the red dopant is not limited thereto.
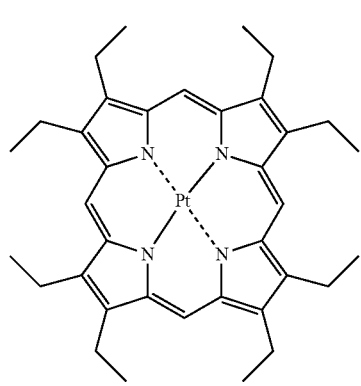
PtOEP
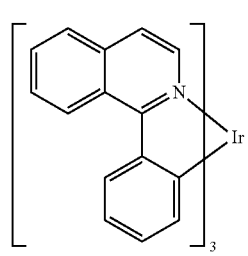
Ir(piq)₃
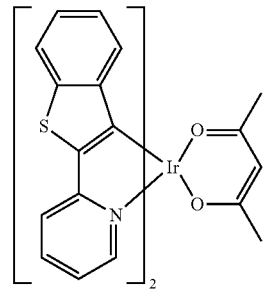
Btp₂Ir(acac)
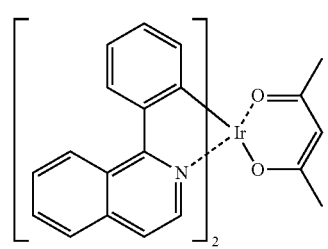
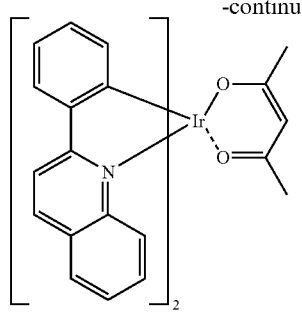
Ir(pq)₂(acac)
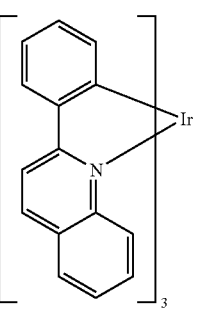
Ir(2-phq)₃
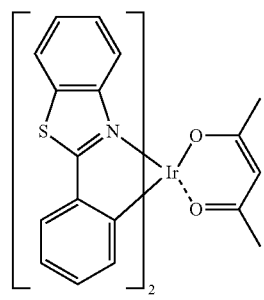
Ir(BT)₂(acac)
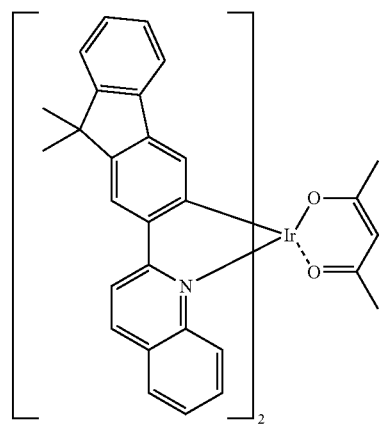
Ir(flq)₂(acac)

-continued
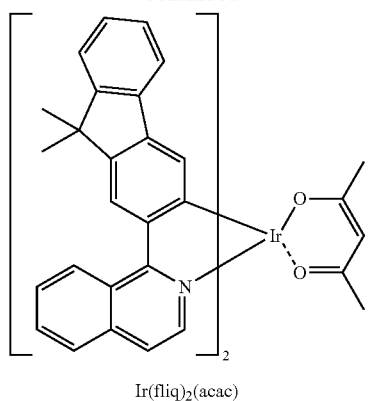
Ir(fliq)₂(acac)
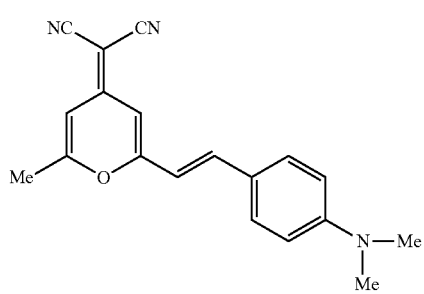
DCM
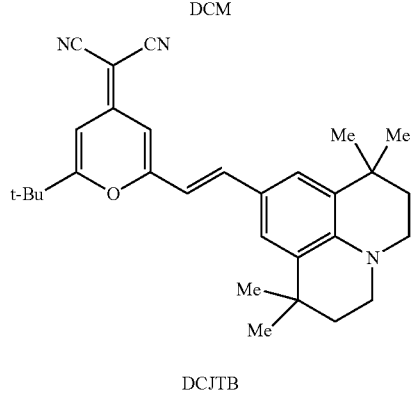
DCJTB
For example, any one of the compounds shown below may be used as the green dopant, but the green dopant is not limited thereto.
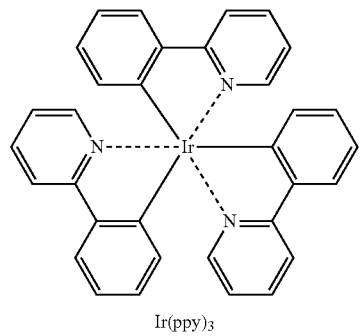
Ir(ppy)₃
-continued
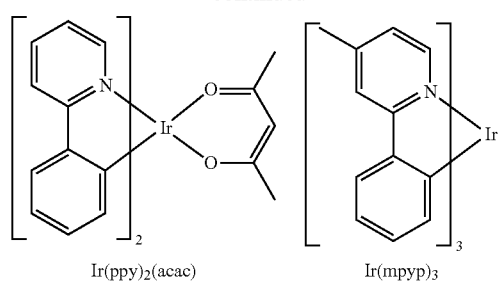
Ir(ppy)₂(acac)       Ir(mpyp)₃
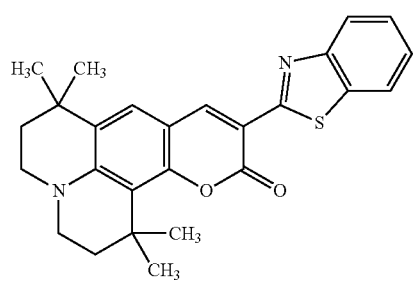
C545T
The dopant may be included in the EML as a complex. For example, the dopant may be any one of D1-D50 as shown below, but the dopant is not limited thereto:
D1
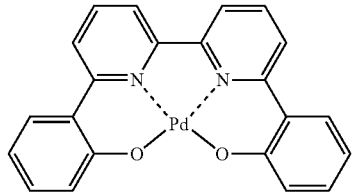
D2
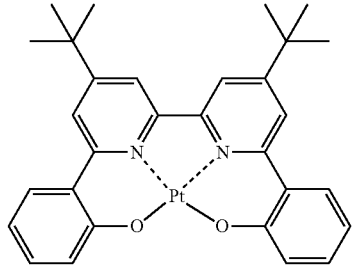
D3
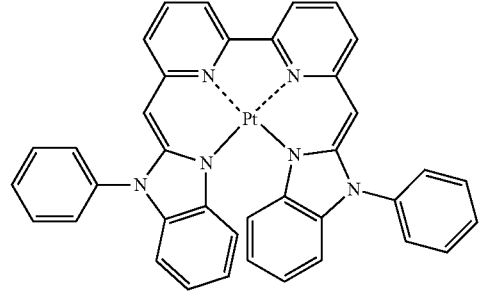

-continued
D4
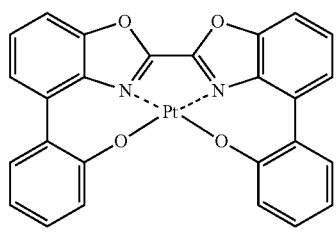
D5
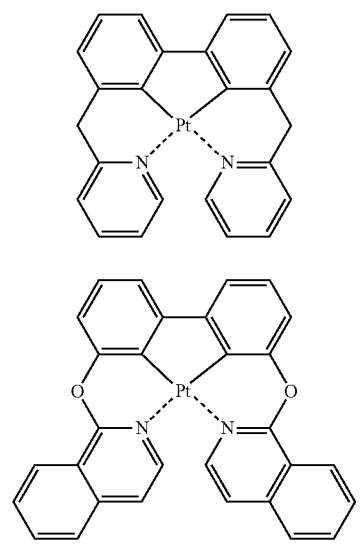
D6
D7
D8
D9
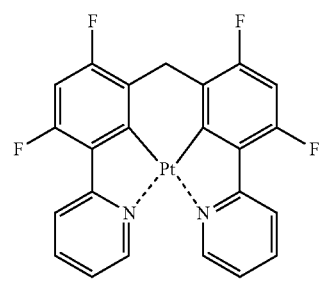
-continued
D10
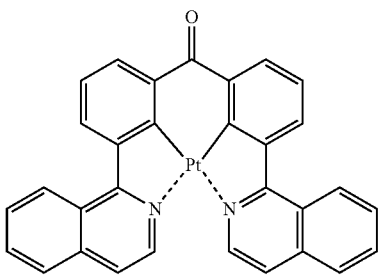
D11
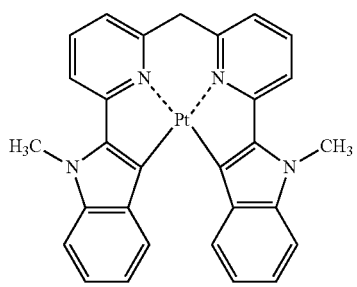
D12
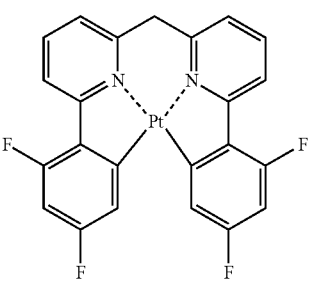
D13
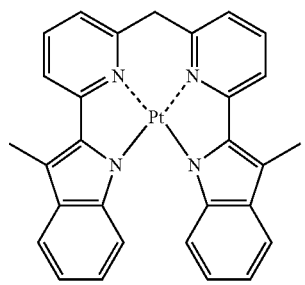
D14
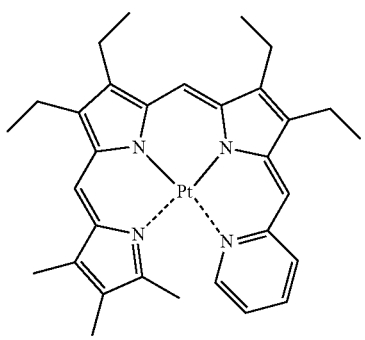

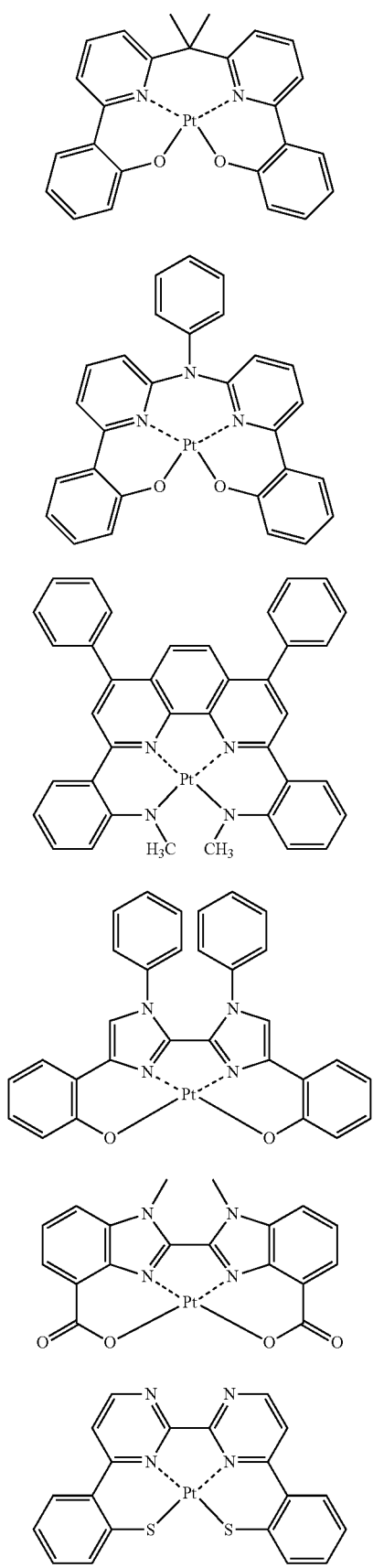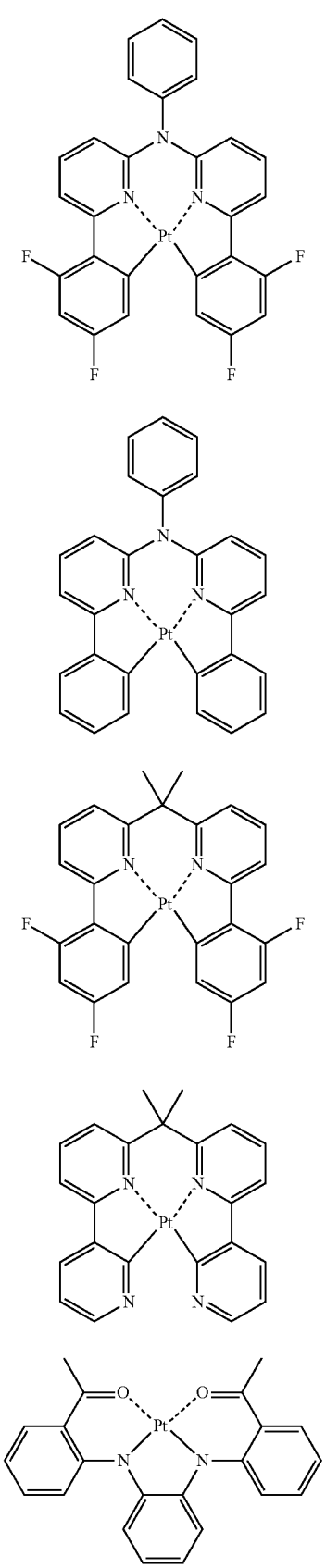

-continued
D26
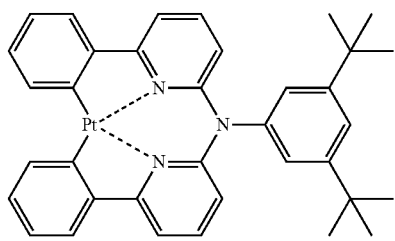
D27
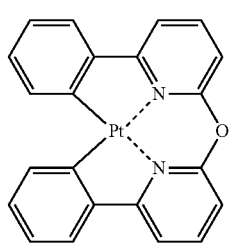
D28
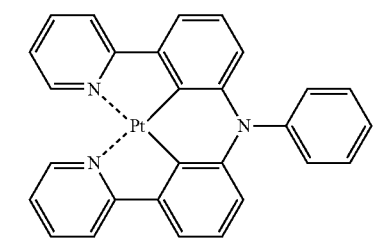
D29
D30
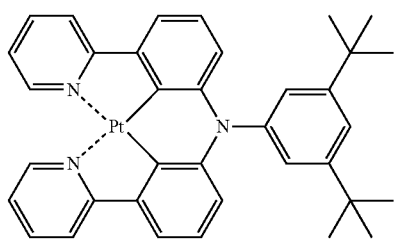
D31
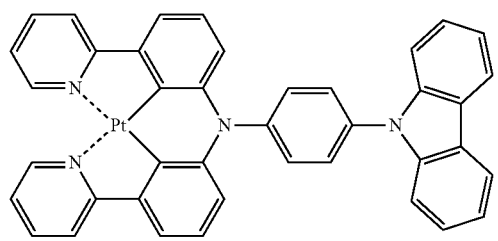
-continued
D32
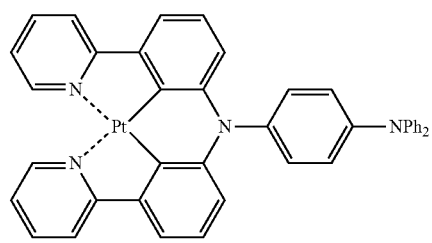
D33
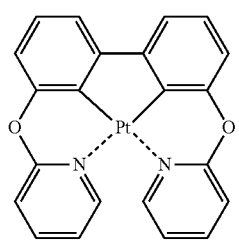
D34
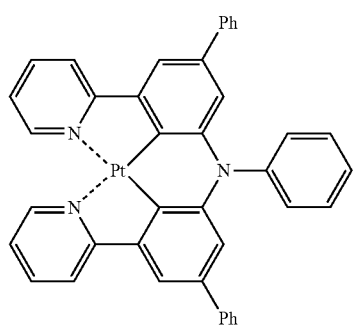
D35
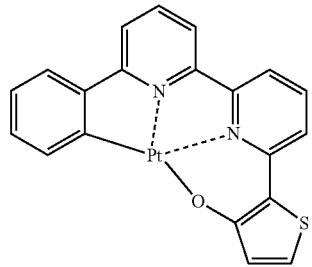
D36
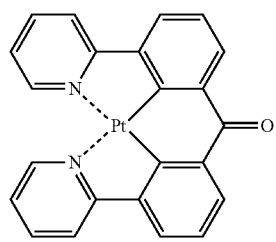

D37 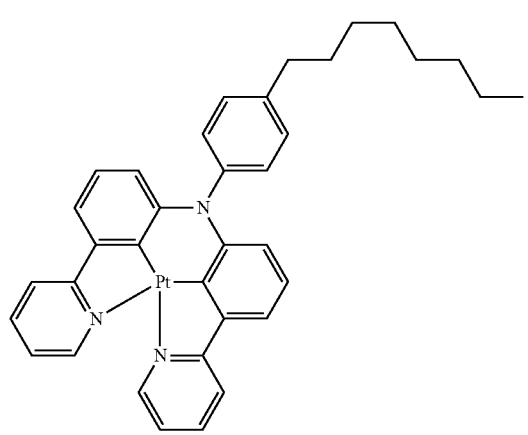
D38 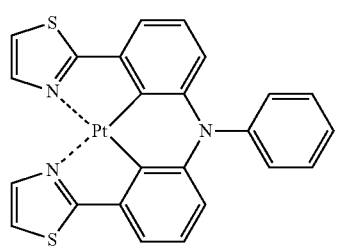
D39 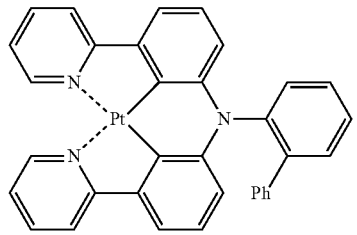
D40 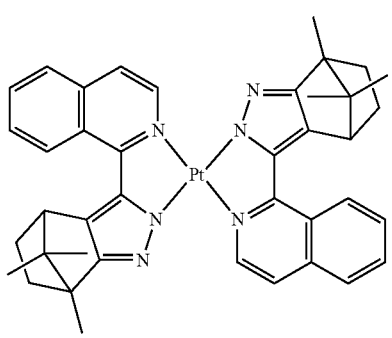
D41 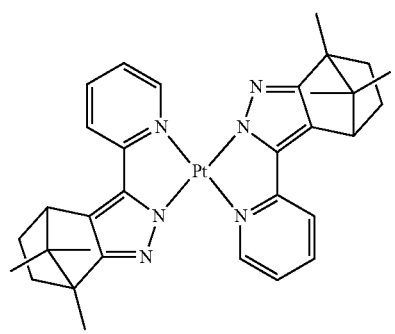
D42 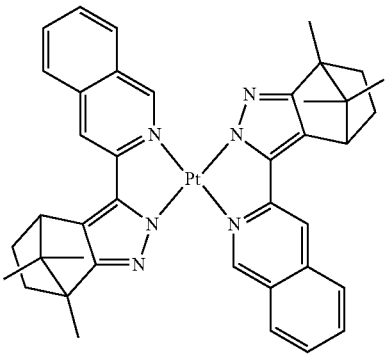
D43 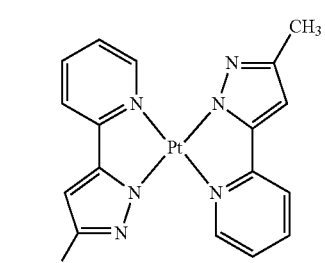
D44 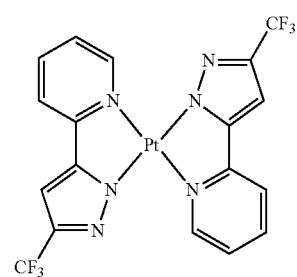
D45 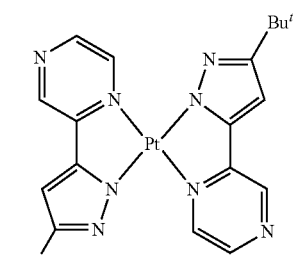
D46 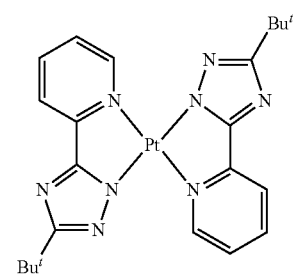

-continued

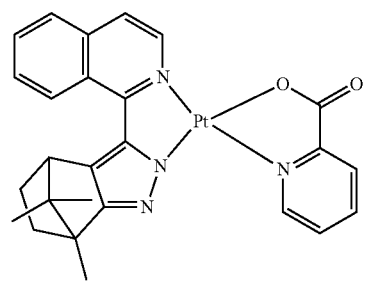
D47

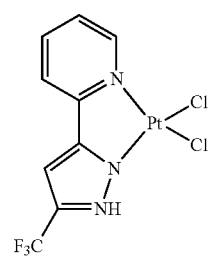
D48

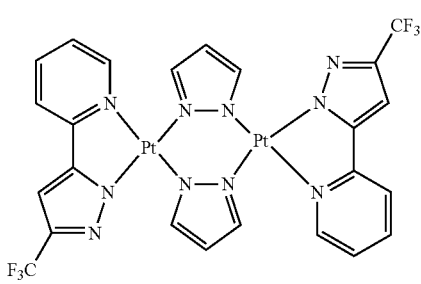
D49

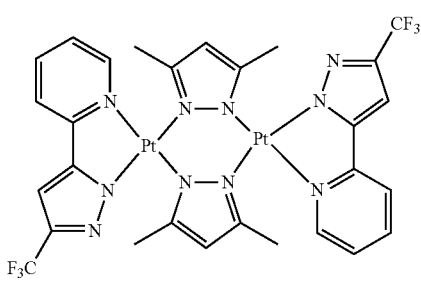
D50

-continued

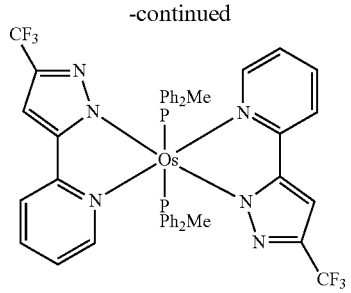
Os(fppz)₂(PPh₂Me)₂

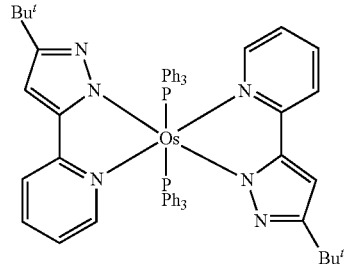
Os(bppz)₂(PPh₃)₂

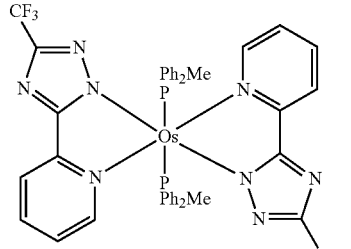
Os(fptz)₂(PPh₂Me)₂

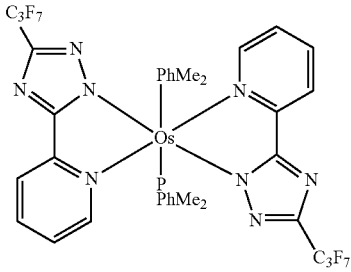
Os(hptz)₂(PPh₂Me₂)₂

The dopant that may be included in the EML may be an Os-complex as shown below, but the dopant is not limited thereto:

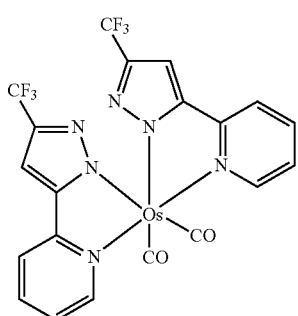
Os(fppz)₂(CO)₂

When the EML includes a host and a dopant, an amount of the dopant may be selected from a range of about 0.01 parts by weight to about 15 parts by weight based on 100 parts by weight of the host, but the amount of the dopant is not limited thereto.

A thickness of the EML may be about 100 Å to about 1000 Å, for example, about 200 Å to about 600 Å. When the thickness of the EML is within any of the foregoing ranges, the EML may have suitable (or satisfactory) light-emitting ability without a substantial increase in driving voltage.

The ETL may be formed on the EML by any of a variety of methods, for example, vacuum deposition, spin coating, or casting. When the ETL is formed by using vacuum deposition or spin coating, the deposition and coating conditions may be similar to those described above with respect to forming the HIL, though the deposition and coating conditions may vary according to a compound that is used to form the ETL.

An electron-transporting material may be any suitable electron-transporting material generally used in the art that may stably transport electrons injected from an electron-injecting electrode (e.g., the cathode). Non-limiting examples of the electron-transporting material include quinoline derivatives, such as tris(8-hydroxyquinolinato)aluminum (Alq3), TAZ, BAlq, beryllium bis(benzoquinolin-10-olate) (Bebq2), 9,10-di(naphthalene-2-yl)anthracene (ADN), BCP, Compound 201, and Compound 202, but the electron-transporting material is not limited thereto.

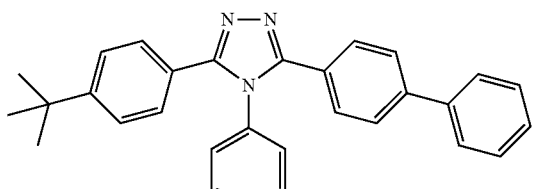

TAZ

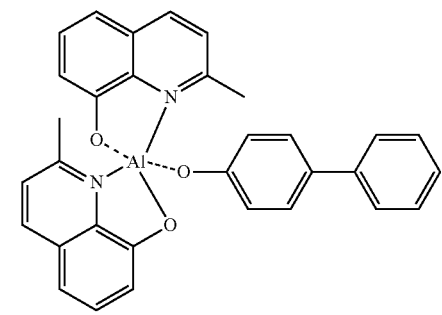

BAlq

Compound 201

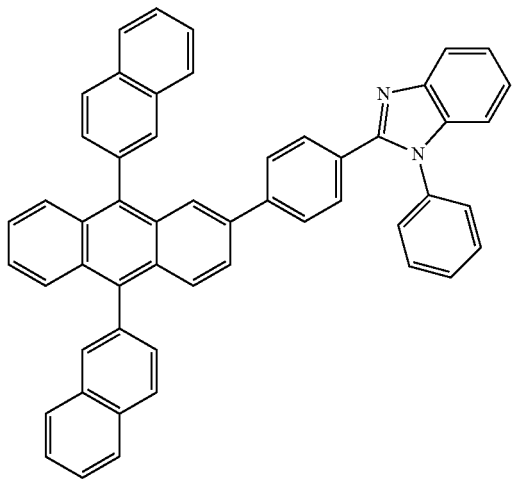

Compound 202

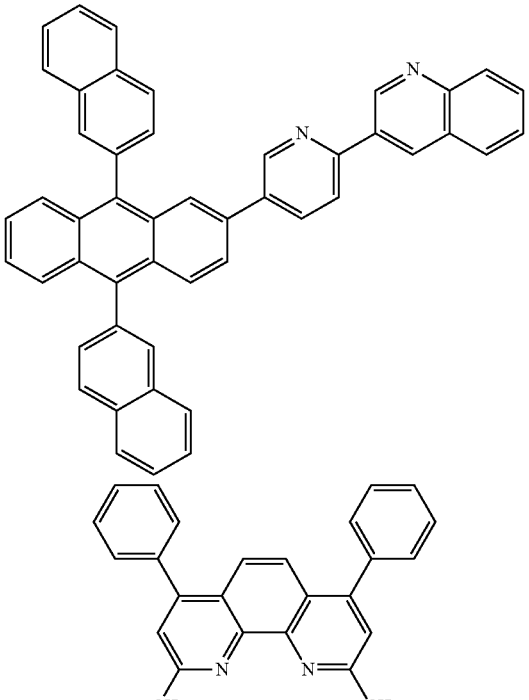

BCP

A thickness of the ETL may be from about 100 Å to about 1,000 Å, and in some embodiments, may be from about 150 Å to about 500 Å. When the thickness of the ETL is within any of the foregoing ranges, the ETL may have suitable (or satisfactory) electron transporting ability without a substantial increase in driving voltage.

In some embodiments, the ETL may further include a metal-containing material in addition to any suitable electron-transporting organic compound generally used in the art.

The metal-containing material may include a Li complex. Non-limiting examples of the Li complex include lithium quinolate (LiQ) and Compound 203 shown below:

Compound 203

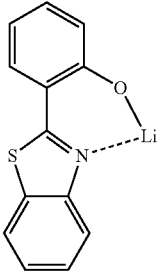

The EIL, which facilitates the injection of electrons from the cathode, may be formed on the ETL. Any suitable electron-injecting material may be used to form the EIL.

A material for forming the EIL can be any suitable EIL material generally used in the art, and non-limiting examples of the EIL material include LiF, NaCl, CsF, $Li_2O$, and BaO.

The deposition conditions for forming the EIL may be similar to those described above with respect to the formation of the HIL, though the deposition conditions may vary according to a compound that is used to form the EIL.

A thickness of the EIL may be from about 1 Å to about 100 Å, and in some embodiments, may be from about 3 Å to about 90 Å. When the thickness of the EIL is within any of the foregoing ranges, the EIL may have suitable (or satisfactory) electron injection ability without a substantial increase in driving voltage.

The second electrode is on the organic layer. The second electrode may be a cathode that is an electron injection electrode, wherein a material included in (or for forming) the second electrode may be a metal, an alloy, an electro-conductive compound, which have a low work function, or a mixture thereof. In this regard, the second electrode may include (or be formed of) lithium (Li), magnesium (Mg), aluminum (Al), aluminum lithium (Al—Li), calcium (Ca), magnesium-indium (Mg—In), magnesium-silver (Mg—Ag), or the like, which may be formed as a thin film type transmission electrode. In some embodiments, to manufacture a top-emission light-emitting device, the transmission electrode may include (or be formed of) indium tin oxide (ITO) or indium zinc oxide (IZO).

Although the organic light-emitting device of the accompanying drawing is described above, the present invention is not limited thereto.

When a phosphorescent dopant is used in the EML, a hole-blocking layer (HBL) may be formed between the H-functional layer and the EML by using vacuum deposition, spin coating, casting, LB deposition, or the like, in order to prevent (or reduce) diffusion of triplet excitons or holes into an ETL. When the HBL is formed by using vacuum deposition or spin coating, the conditions for deposition and coating may be similar to those described above with respect to the formation of the HIL, though the conditions for deposition and coating may vary according to a compound that is used to form the HBL. Any suitable hole-blocking material generally used in the art may be used, and non-limiting examples of the hole-blocking material include oxadiazole derivatives, triazole derivatives, phenanthroline derivatives, or the like. In some embodiments, BCP, which is shown below, may be used as a hole-blocking material.

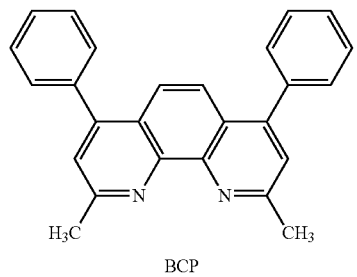

BCP

A thickness of the HBL may be from about 20 Å to about 1000 Å, and in some embodiments, may be from about 30 Å to about 300 Å. When the thickness of the HBL is within any of the foregoing ranges, the HBL may have improved hole blocking ability without a substantial increase in driving voltage.

An organic light-emitting device according to an embodiment of the present invention may be included in various forms of display devices (e.g., flat or curved display devices), such as passive matrix organic light-emitting display devices and active matrix organic light-emitting display devices. When the organic light-emitting device is included in an active matrix organic light-emitting display device, a first electrode provided on a side of a substrate may be electrically connected to a source electrode or a drain electrode of a thin film transistor as a pixel electrode. The organic light-emitting device may be included in a flat display device (e.g., a flexible display device) capable of displaying on both sides thereof.

An organic layer of the organic light-emitting device according to an embodiment of the present invention may be formed by a deposition method by using a compound represented by Formula 1 according to an embodiment of the present invention or by a wet method that involves coating the compound represented by Formula 1 according to an embodiment of the present invention, which is prepared as a solution.

Hereinafter, an organic light-emitting device according to embodiments of the present invention will be described with reference to Synthesis Examples and Examples; however, the present invention is not limited to the Synthesis Examples and Examples.

EXAMPLE

Synthesis Example 1: Synthesis of Compound 1

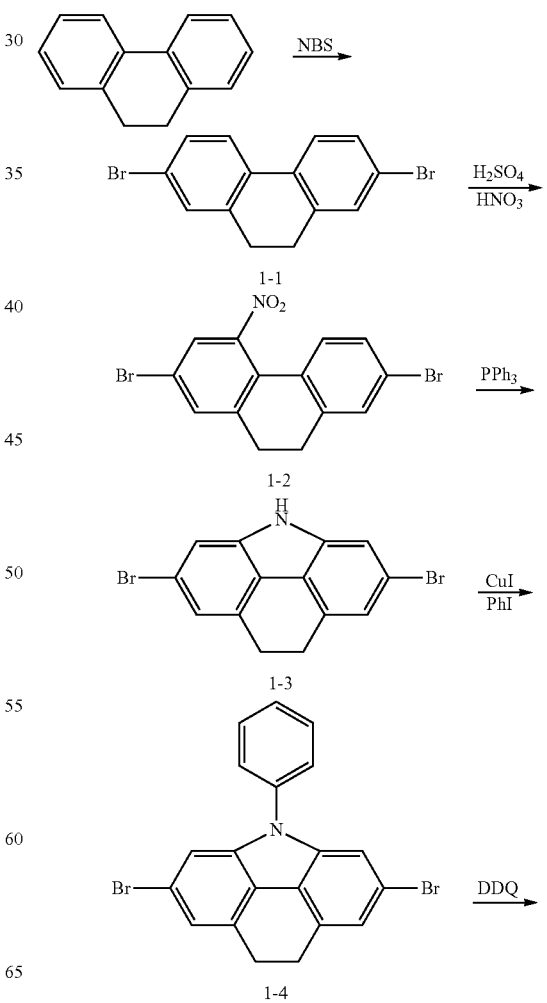

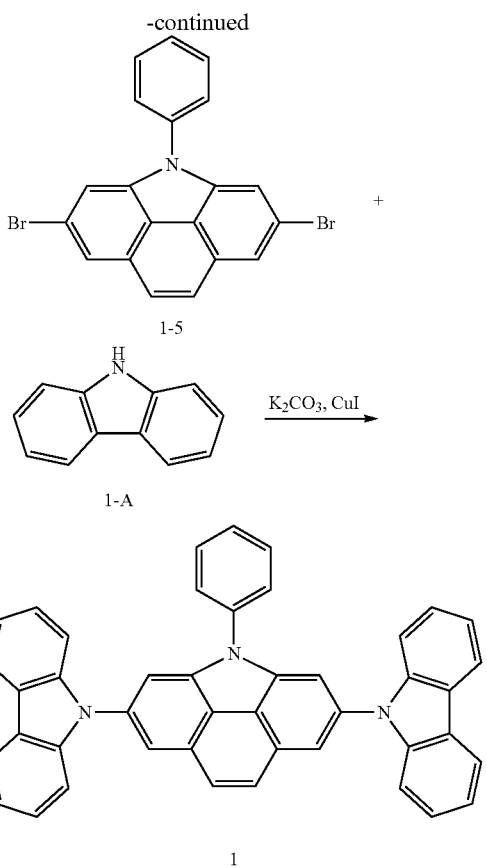

Synthesis of Intermediate 1-1

10.0 g (55.4 mmol) of 9,10-dihydrophenanthrene, 21.8 g (121.0 mmol) of N-bromosuccinimide (NBS), and 0.5 g (2.7 mmol) of p-toluenesulfonic acid (p-TsOH) were added to 30 mL of acetonitrile and then stirred at a temperature of 50° C. for 12 hours to prepare a reaction solution. The reaction solution was cooled to room temperature and then stirred for 30 minutes to precipitate crystals. The crystals were collected through a reduced pressure filter and washed with methanol to obtain 8.4 g (yield 45%) of gray crystals of Intermediate 1-1. The compound obtained therefrom was analyzed using liquid chromatography-mass spectrometry (LC-MS). $C_{14}H_{10}Br_2$ M$^+$ 335.9

Synthesis of Intermediate 1-2

5.0 g (15.0 mmol) of Intermediate 1-1 was completely dissolved in 50 mL of dichloromethane, and 1.7 g (30.0 mmol) of nitric acid was added thereto at room temperature. Then, 1.5 g (15.0 mmol) of sulfuric acid was slowly added thereto in a dropwise manner, and then, the resultant mixture was stirred at a temperature of 30° C. for 6 hours. After the 6 hours (e.g., after completing or substantially completing the reaction), the resultant mixture (the reactants) was cooled to room temperature, 50 mL of methanol was added thereto and then stirred for 2 hours to precipitate crystals. The crystals were collected through a reduced pressure filter and washed with methanol to obtain 5.2 g (yield 90%) of yellow crystals of Intermediate 1-2. The compound obtained therefrom was analyzed using LC-MS. $C_{14}H_9Br_2NO_2$ M$^+$ 380.9

Synthesis of Intermediate 1-3

4.6 g (12.0 mmol) of Intermediate 1-2 was dissolved in 30 mL o-dichlorobenzene and then heated to completely (or substantially completely) dissolve Intermediate 1-2. 4.7 g (18.0 mmol) of triphenylphosphine was added to the resultant mixture, and then, the mixture was stirred at a temperature of 180° C. for 3 hours to prepare a reaction solution. The reaction solution was cooled to room temperature, a solvent was evaporated therefrom and residues obtained therefrom were separated and purified by using silica gel column chromatography. Then, the separated and purified residues were washed with methanol to obtain 2.9 g (yield 70%) of white crystals of Intermediate 1-3. The compound obtained therefrom was analyzed using LC-MS. $C_{14}H_{11}Br_2N$ M$^+$ 350.9

Synthesis of Intermediate 1-4

10 g (10.0 mmol) of Intermediate 1-3 was dissolved in 100 ml of toluene in an oxygen containing atmosphere, and 0.6 g (0.3 mmol) of 2,3-dichloro-5,6-dicyano-1,4-benzoquinone (DDQ) and 0.2 g (0.3 mmol) of NaNO$_2$ were added thereto at room temperature. Then, the resultant mixture was stirred at a temperature of 110° C. for 6 hours to prepare a reaction solution. After the 6 hours (e.g., after completing or substantially completing the reaction), the reaction solution was cooled to room temperature and a solvent was evaporated therefrom to obtain residues. The residues were separated and purified by using silica gel column chromatography to obtain 3.1 g (yield 90%) of Intermediate 1-4. The compound obtained therefrom was analyzed using LC-MS. $C_{14}H_7Br_2N$ M$^+$ 346.8

Synthesis of Intermediate 1-5

3.4 g (10.0 mmol) of Intermediate 1-4, 2.5 g (12.0 mmol) of iodobenzene, 0.2 g (1.0 mmol) of 10-phenanthroline, 0.2 g (2.0 mmol) of CuI, and 4.1 g (30.0 mmol) of K$_2$CO$_3$ were added to, and dissolved in, 30 mL of N,N-dimethylformamide (DMF). Then, the resultant mixture was stirred at a temperature of 80° C. for 24 hours to obtain a reaction solution. The reaction solution was cooled to room temperature and then extracted three times with 30 mL of water and 40 mL of diethylether to collect organic layers. The organic layers were dried with magnesium sulfate and a solvent was evaporated therefrom to obtain residues. The residues were separated and purified by using a silica gel column chromatography to obtain 3.8 g (yield 89%) of Intermediate 1-5. The compound obtained therefrom was analyzed using LC-MS. $C_{20}H_{11}Br_2N$ M$^+$ 422.9

Synthesis of Compound 1

4.25 g (10.0 mmol) of Intermediate 1-5, 3.68 g (22.0 mmol) of Compound 1-A, 0.4 g (2.0 mmol) of 10-phenanthroline, 0.4 g (4.0 mmol) of CuI, and 8.2 g (60.0 mmol) of K$_2$CO$_3$ were dissolved in 50 mL of N,N-dimethylformamide (DMF). Then, the resultant mixture was stirred at a temperature of 80° C. for 24 hours to prepare a reaction solution. The reaction solution was cooled to room temperature and then extracted three times with 50 mL of water and 60 mL of diethylether to collect organic layers. The organic layers were dried with magnesium sulfate and a solvent was evaporated to obtain residues. The residues were separated and purified by using a silica gel column chromatography to obtain 4.90 g (yield 82%) of Compound 1. The compound obtained therefrom was analyzed using LC-MS. $C_{44}H_{27}N_3$ cal. 597.22, found 597.23.

Synthesis Example 2: Synthesis of Compound 17

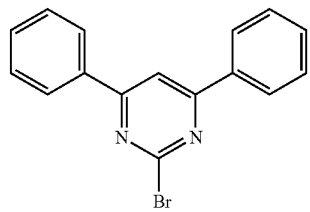

17-A

Compound 17 was synthesized as in the synthesis of Compound 1, except that Compound 17-A was used instead of iodobenzene in the synthesis method of Intermediate 1-5 in Synthesis Example 1. The compound obtained therefrom was analyzed using LC-MS.

$C_{54}H_{33}N_5$ cal. 751.27, found 751.28.

Synthesis Example 3: Synthesis of Compound 20

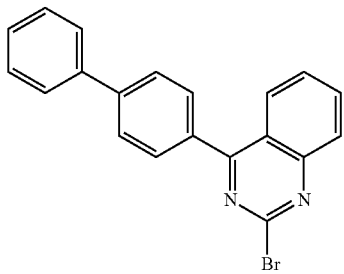

20-A

Compound 20 was synthesized as in the synthesis of Compound 1, except that Compound 20-A was used instead of iodobenzene during the synthesis of Intermediate 1-5 in Synthesis Example 1. The compound obtained therefrom was analyzed using LC-MS.

$C_{58}H_{35}N_5$ cal. 801.29, found 801.30.

Synthesis Example 4: Synthesis of Compound 27

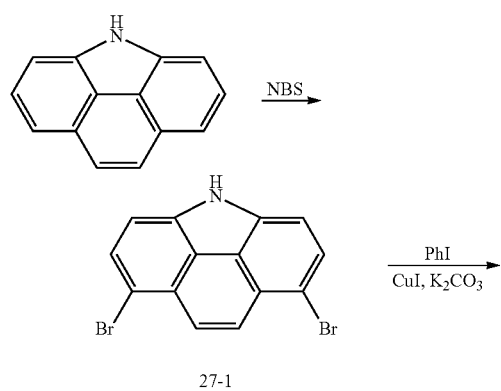

27-1

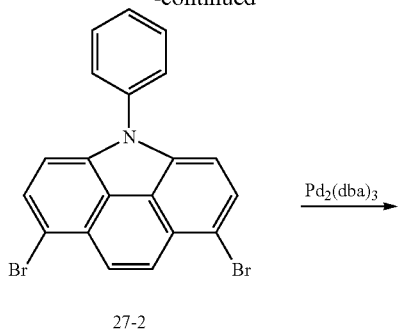

27-2

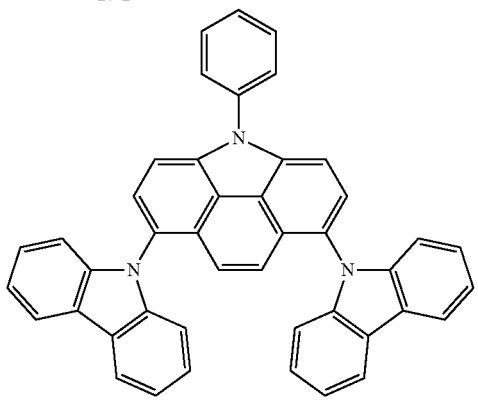

27

Synthesis of Intermediate 27-1

3.56 g (20.0 mmol) of N-bromosuccinimide (NBS) was added to a solution in which 1.91 g (10.0 mmol) of 6H-benzo[def]carbazole was completely dissolved in 60 mL of carbon tetrachloride ($CCl_4$). Then, the resultant mixture was stirred at a temperature of 80° C. for 30 minutes to prepare a reaction solution. The reaction solution was cooled to room temperature and then stirred for 30 minutes to precipitate crystals. The crystals were collected by using a reduced pressure filter and washed with methanol to obtain 1.71 g (yield 49%) of white crystals of Intermediate 27-1. The compound obtained therefrom was analyzed using LC-MS. $C_{14}H_7Br_2N$: M+ 346.9

Synthesis of Intermediate 27-2

10.0 g (28.7 mmol) of Intermediate 27-1, 7.0 g (34.4 mmol) of iodobenzene, 0.5 g (2.87 mmol) of 1,10-phenanthroline, 1.1 g (5.74 mmol) of CuI, and 11.9 g (86.1 mmol) of $K_2CO_3$ were dissolved in 100 mL of dimethylformamide (DMF). Then, the resultant mixture was stirred at a temperature of 80° C. for 24 hours to prepare a reaction solution. The reaction solution was cooled to room temperature and then extracted with 100 mL of water to collect organic layers. The collected organic layers were dried with magnesium sulfate and a solvent was evaporated therefrom to obtain residues. The residues were separated and purified by using silica gel column chromatography to obtain 9.51 g (yield 78%) of Intermediate 27-2. The compound obtained therefrom was analyzed using LC-MS. $C_{20}H_{11}Br_2N$: M+422.9

Synthesis of Compound 27

4.2 g (10.0 mmol) of Intermediate 27-2, 3.68 g (22.0 mmol) of Compound 1-A, 0.73 g (0.8 mmol) of tris(dibenzylideneacetone)dipalladium(0) ($Pd_2(dba)_3$), 0.16 g (0.8 mmol) of $PtBu_3$, and 2.8 g (30.0 mmol) of KOtBu were dissolved in 60 ml of toluene. Then, the resultant mixture was stirred at a temperature of 85° C. for 4 hours to prepare a reaction solution. The reaction solution was cooled to room temperature and then extracted three times with 50 mL of water and 50 mL of diethylether to collect organic layers. The collected organic layers were dried with magnesium sulfate to obtain residues. The residues were separated and purified by using silica gel column chromatography to obtain 4.90 g (yield 82%) of Compound 27. The compound obtained therefrom was analyzed using LC-MS. $C_{44}H_{27}N_3$ cal. 597.22, found 597.23.

Synthesis Example 5: Synthesis of Compound 33

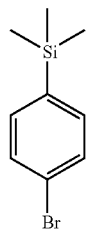

33-A

Compound 33 was synthesized as in the synthesis of Compound 27, except that Compound 33-A was used instead of iodobenzene in the synthesis method of Intermediate 27-2 in Synthesis Example 4. The compound obtained therefrom was analyzed using LC-MS.
$C_{47}H_{35}N_3Si$ cal. 669.26, found 669.27.

Synthesis Example 6: Synthesis of Compound 45

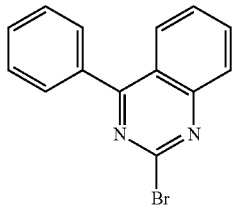

45-A

Compound 45 was synthesized as in the synthesis of Compound 27, except that Compound 45-A was used instead of iodobenzene in the synthesis method of Intermediate 27-2 in Synthesis Example 4. The compound obtained therefrom was analyzed using LC-MS.
$C_{52}H_{31}N_5$ cal. 725.26, found 725.27.

Synthesis Example 7: Synthesis of Compound 48

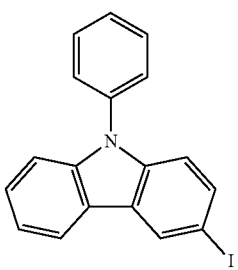

48-A

Compound 48 was synthesized as in the synthesis of Compound 27, except that Compound 48-A was used instead of iodobenzene in the synthesis method of Intermediate 27-2 in Synthesis Example 4. The compound obtained therefrom was analyzed using LC-MS.

$C_{56}H_{34}N_4$ cal. 762.28, found 762.29.

Synthesis Example 8: Synthesis of Compound 54

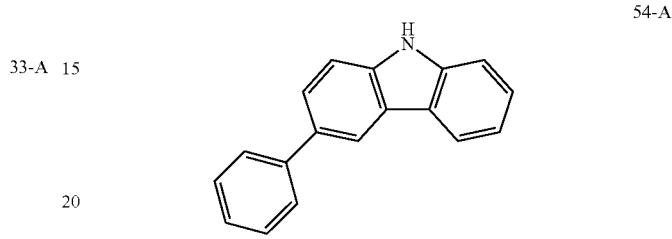

54-A

Compound 54 was synthesized as in the synthesis of Compound 27, except that Compound 54-A was used instead of Compound 1-A in the synthesis method of Compound 27 in Synthesis Example 4. The compound obtained therefrom was analyzed using LC-MS. $C_{56}H_{35}N_3$ cal. 749.28, found 749.29.

The same general synthesis method as in the synthesis pathways described above and suitable intermediate materials were used to synthesize additional compounds. $^1$H NMR and fast atom bombardment mass spectrometry (MS/FAB) of the additional compounds synthesized are shown in Table 1 below.

Synthesis methods of Compounds other than the Compounds shown in Table 1 may be easily inferred by one of ordinary skill in the art based on the synthesis pathways and raw materials described above.

TABLE 1

| Compound | $^1$H NMR (CDCl$_3$, 400 MHz) δ | MS/FAB found | calc. |
|---|---|---|---|
| 1 | 8.15-8.10 (m, 4H), 7.63-7.58 (m, 2H), 7.55-7.51 (m, 2H), 7.43-7.35 (m, 13H), 7.31-7.26 (m, 4H), 7.22-7.20 (m, 2H) | 597.23 | 597.22 |
| 5 | 8.15-8.10 (m, 4H), 7.43-7.36 (m, 12H), 7.31-7.26 (m, 4H), 7.21-7.14 (m, 6H) | 615.22 | 615.21 |
| 9 | 8.15-8.10 (m, 4H), 7.64-7.61 (m, 2H), 7.53-7.47 (m, 4H), 7.43-7.36 (m, 13H), 7.32-7.27 (m, 6H), 7.23-7.21 (m, 2H) | 673.26 | 673.25 |
| 11 | 8.64-8.62 (m, 1H), 8.15-8.10 (m, 4H), 7.91-7.86 (m, 1H), 7.68-7.63 (m, 1H), 7.45-7.34 (m, 14H), 7.31-7.25 (m, 5H), | 598.23 | 598.22 |
| 17 | 8.27-8.22 (m, 4H), 8.12-8.06 (m, 6H), 7.93 (s, 1H), 7.56-7.52 (m, 6H), 7.43-7.36 (m, 8H), 7.33-7.25 (m, 8H) | 751.28 | 751.27 |
| 20 | 8.34-8.30 (m, 2H), 8.12-8.09 (m, 6H), 8.01-7.97 (m, 2H), 7.94-7.85 (m, 4H), 7.64-7.58 (m, 3H), 7.54-7.49 (m, 4H), 7.42-7.37 (m, 8H), 7.35-7.33 (m, 2H), 7.31-7.27 (m, 4H) | 801.30 | 801.29 |
| 22 | 8.37-8.32 (m, 1H), 8.12-8.09 (m, 4H), 7.92-7.90 (m, 1H), 7.51-7.46 (m, 4H), 7.43-7.27 (m, 21H), 7.23-7.20 (m, 3H) | 762.29 | 762.28 |
| 27 | 8.14-8.10 (m, 4H), 7.91 (s, 2H), 7.79 (s, 1H), 7.77 (s, 1H), 7.56-7.49 (m, 4H), 7.44-7.40 (m, 4H), 7.39-7.35 (m, 5H), 7.31-7.27 (m, 4H), 7.10 (s, 1H), 7.08 (s, 1H) | 597.23 | 597.22 |

TABLE 1-continued

| Compound | $^1$H NMR (CDCl$_3$, 400 MHz) δ | MS/FAB found | MS/FAB calc. |
|---|---|---|---|
| 32 | 8.15-8.12 (m, 4H), 7.91 (s, 2H), 7.79-7.73 (m, 4H), 7.48-7.42 (m, 6H), 7.39-7.35 (m, 4H), 7.31-7.27 (m, 4H), 7.02 (s, 1 H), 7.00 (s, 1 H) | 622.23 | 622.22 |
| 33 | 8.12-8.08 (m, 4H), 7.91 (s, 2H), 7.79 (s, 1H), 7.77 (s, 1H), 7.62-7.58 (m, 2H), 7.44-7.35 (m, 10H), 7.31-7.27 (m, 4H), 7.03 (s, 1H), 7.01 (s, 1H), 0.26 (s, 9H) | 669.27 | 669.26 |
| 37 | 8.30-8.26 (m, 1H), 8.12-8.06 (m, 5H), 7.96 (s, 2H), 7.87 (s, 1H), 7.85 (s, 1H), 7.75-7.71 (m, 2H), 7.87 (d, 1H), 7.44-7.35 (m, 10H), 7.31-7.27 (m, 5H) | 648.24 | 648.23 |
| 44 | 8.78-8.75 (m, 4H), 8.12-8.08 (m, 4H), 8.00 (s, 2H), 7.80 (s, 1H), 7.76 (s, 1H), 7.66-7.62 (m, 6H), 7.44-7.35 (m, 10H), 7.31-7.27 (m, 4H) | 752.28 | 752.27 |
| 45 | 8.12-8.08 (m, 4H), 8.00-7.96 (m, 3H), 7.90-7.84 (m, 4H), 7.76-7.72 (m, 2H), 7.68-7.66 (m, 4H), 7.64-7.59 (m, 2H), 7.44 -7.42(m, 4H), 7.39-7.35 (m, 4H), 7.31-7.27 (m, 4H) | 725.27 | 725.26 |
| 49 | 8.12-8.08 (m, 4H), 7.91-7.89 (m, 3H), 7.79 (s, 1H), 7.77-7.74 (m, 3H), 7.64-7.62 (m, 1H), 7.55-7.51 (m, 1H), 7.44-7.35 (m, 9H), 7.33-7.27 (m, 5H), 7.04 (s, 1H), 7.01 (s, 1H) | 687.24 | 687.23 |
| 53 | 8.75-8.73 (m, 2H), 8.38 (t, 1H), 8.12-8.08 (m, 4H), 8.01-7.99 (m, 2H), 7.91 (s, 2H), 7.80-7.76 (m, 4H), 7.66-7.64 (m, 2H), 7.44-7.35 (m, 8H), 7.30-7.27 (m, 6H), 7.08 (s, 1H), 7.06 (s, 1H) | 751.28 | 751.27 |
| 54 | 8.25-8.22 (m, 2H), 8.10-8.08 (m, 2H), 7.91 (s, 2H), 7.79 (s, 1H), 7.77 (s, 1H), 7.73-7.66 (m, 6H), 7.56-7.35 (m, 17H), 7.32-7.28 (m, 2H), 7.10 (s, 1H), 7.08 (s, 1H) | 749.29 | 749.28 |

Example 1

As an anode, 70/1000/70 Å of ITO/Ag/ITO was deposited on a glass substrate, which was cut into a size of 50 mm×50 mm×0.5 mm and then ultrasonically washed by using isopropyl alcohol and distilled water for 5 minutes, followed by cleaning by UV irradiation and exposure to ozone for about 30 minutes. The glass substrate was then loaded into a vacuum deposition device. 4,4',4''-tris(N-(2-naphthyl)-N-phenyl-amino)-triphenylamine (2-TNATA), which is a suitable material for an HIL, was vacuum deposited on the substrate to form an HIL having a thickness of 600 Å, and 4,4'-bis[N-(1-naphthyl)-N-phenyl amino]biphenyl (NPB) was vacuum deposited thereon to form an HTL having a thickness of 1000 Å. On the HTL, Compound 1 according to an embodiment of the present invention as a green phosphorescent host, and Ir(ppy)$_3$ as a dopant were concurrently (simultaneously) vacuum deposited at a weight ratio of 91:9 to form an EML having a thickness of 250 Å. Then, BCP was vacuum deposited on the EML as a hole blocking compound to form an HBL having a thickness of 50 Å. Then, Alq$_3$ was vacuum deposited thereon to form an ETL having a thickness of 350 Å, and LiF, which is a halogenated alkali metal, was vacuum deposited thereon to form an EIL having a thickness of 10 Å. Then, Mg and Ag were vacuum deposited thereon at a weight ratio of 90:10 to form an electrode having a thickness of 120 Å and complete the manufacture of an organic light-emitting device.

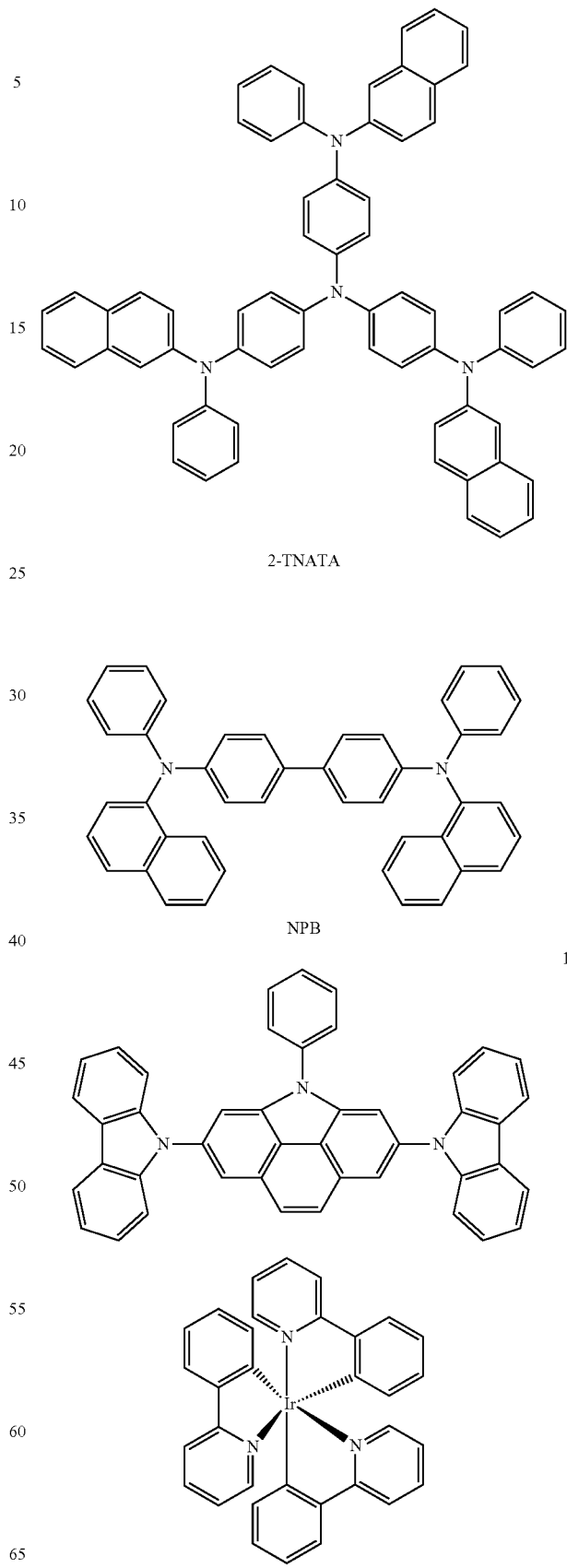

-continued

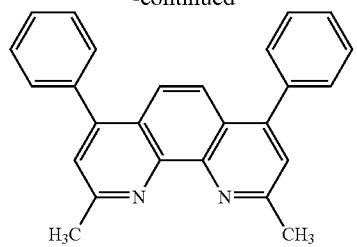
BCP

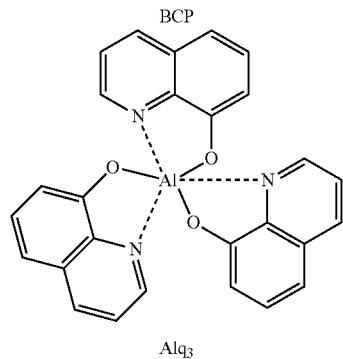
Alq3

Example 2

An organic light emitting device was manufactured as in Example 1, except that Compound 18 was used instead of Compound 1 when forming the EML.

Example 3

An organic light emitting device was manufactured as in Example 1, except that Compound 49 was used instead of Compound 1 when forming the EML.

Example 4

When forming an HTL in Example 1, 4,4'-bis[N-(1-naphthyl)-N-phenylamino]biphenyl (NPB), which is a hole-transporting material, was vacuum deposited to form an HTL having a thickness of 1350 Å. An organic light-emitting device was manufactured as in Example 1, except that Compound 20 according to an embodiment of the present invention as a red phosphorescent host and bis(2-(2'-benzo[4,5-a]thienyl) pyridinato-N, C3') iridium acetylacetonate (BtpIr) as a dopant, were co-deposited on the HTL at a weight ratio of 94:6, instead of Compound 1 and Ir(ppy)$_3$, to form an EML having a thickness of 400 Å.

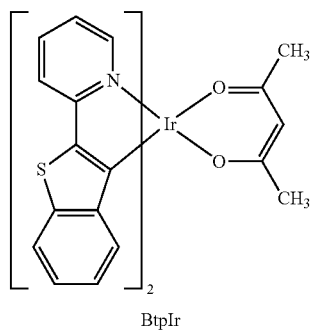
BtpIr

Example 5

An organic light-emitting device was manufactured as in Example 4, except that Compound 44 was used instead of Compound 20, when forming the EML.

Example 6

An organic light-emitting device was manufactured as in Example 4, except that Compound 48 was used instead of Compound 20, when forming the EML.

Comparative Example 1

An organic light-emitting device was manufactured as in Example 1, except that CBP (4,4'-N,N'-dicarbazolbiphenyl), which is a suitable green phosphorescent host, was used instead of Compound 1, when forming the EML.

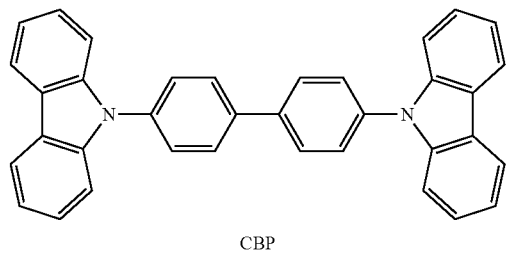 [SMILES: c1ccc2c(c1)c1ccccc1n2-c1ccc(-c2ccc(-n3c4ccccc4c4ccccc43)cc2)cc1 ; "CBP"]
CBP

Comparative Example 2

An organic light-emitting device was manufactured as in Example 4, except that CBP (4,4'-N,N'-dicarbazolbiphenyl), which is a suitable red phosphorescent host, was used instead of Compound 20, when forming the EML.

As a result of using the compound having the structure of Formula 1 according to an embodiment of the present invention as green or red phosphorescent materials of the EML in an organic light-emitting device, the organic light-emitting device showed improved driving voltage and excellent I-V-L characteristics with substantially improved efficiency as compared with using CBP, which is a material used in the art. For example, effects of improvement in lifespan were excellent, thereby substantially improving the lifespan of the organic light-emitting device. As a result, it may be concluded that heterocyclic compounds having carbazole groups as substituents according to embodiments of the present invention are effective green or red phosphorescent host materials. Representative characteristics and lifespan results are summarized in Table 2 below.

TABLE 2

|  | Phosphorescent host material | Driving voltage (V) | Current density (mA/cm$^2$) | Brightness (cd/m$^2$) | Efficiency (cd/A) | Emitted color | Lifespan LT97% (hr) |
| --- | --- | --- | --- | --- | --- | --- | --- |
| Example 1 | Compound 1 | 5.65 | 10 | 4,935 | 49.4 | green | 73 hr |
| Example 2 | Compound 18 | 5.88 | 10 | 5,012 | 50.1 | green | 69 hr |
| Example 3 | Compound 49 | 5.79 | 10 | 4,956 | 49.6 | green | 81 hr |
| Example 4 | Compound 20 | 5.88 | 10 | 2,650 | 26.5 | red | 91 hr |
| Example 5 | Compound 44 | 5.69 | 10 | 2,710 | 27.1 | red | 82 hr |
| Example 6 | Compound 48 | 5.79 | 10 | 2,415 | 24.2 | red | 97 hr |
| Comparative Example 1 | CBP | 6.52 | 10 | 3,210 | 32.1 | green | 32 hr |
| Comparative Example 2 | CBP | 6.80 | 10 | 3,225 | 16.4 | red | 45 hr |

As described above, according to one or more embodiments of the present invention, a compound represented by Formula 1 has excellent emission characteristics and material stability and thus, the compound is useful as a phosphorescent host material. By using an embodiment of the compound, an organic light-emitting device having high efficiency, low driving voltage, high brightness, and long lifespan may be manufactured.

It should be understood that the embodiments described herein should be considered in a descriptive sense only and not for purposes of limitation. Descriptions of features or aspects within each embodiment should typically be considered as available for other similar features or aspects in other embodiments.

While certain embodiments of the present invention have been described with reference to the figures, it will be understood by those of ordinary skill in the art that various changes may be made the described embodiments without departing from the spirit and scope of the present invention as defined by the following claims, and equivalents thereof.

What is claimed is:

1. A compound represented by Formula 1:

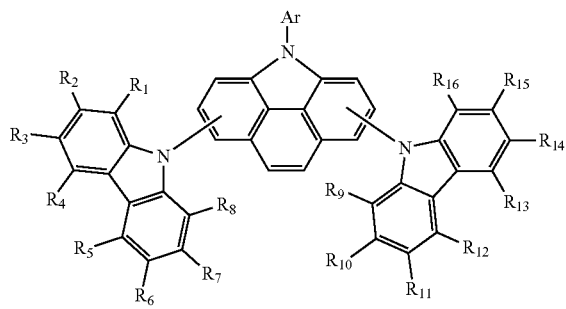

Formula 1 in Formula 1,
R$_1$ to R$_{16}$ are each independently a hydrogen atom; a deuterium atom; a halogen atom; a cyano group; a substituted or unsubstituted C$_1$-C$_{60}$ alkyl group; a substituted or unsubstituted C$_2$-C$_{60}$ alkenyl group; a substituted or unsubstituted C$_2$-C$_{60}$ alkynyl group; a substituted or unsubstituted C$_3$-C$_{60}$ cycloalkyl group; a substituted or unsubstituted C$_3$-C$_{60}$ cycloalkenyl group; a substituted or unsubstituted C$_6$-C$_{60}$ aryl group; a substituted or unsubstituted C$_1$-C$_{60}$ heteroaryl group; an amino group substituted with a C$_6$-C$_{60}$ aryl group or a C$_1$-C$_{60}$ heteroaryl group; or a substituted or unsubstituted C$_6$-C$_{60}$ condensed polycyclic group, and Ar is a substituted or unsubstituted C$_1$-C$_{60}$ alkyl group, a substituted or unsubstituted C$_6$-C$_{60}$ aryl group, a substituted or unsubstituted C$_1$-C$_{60}$ heteroaryl group, or a substituted or unsubstituted C$_6$-C$_{60}$ condensed polycyclic group.

2. The compound of claim 1, wherein the compound is represented by Formula 2:

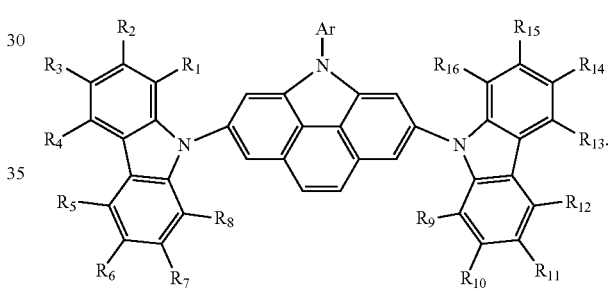

Formula 2

3. The compound of claim 1, wherein the compound is represented by Formula 3:

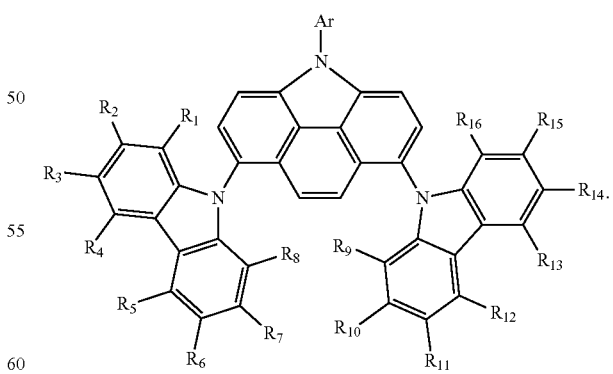

Formula 3

4. The compound of claim 1, wherein in Formula 1, R$_1$, R$_4$, R$_5$, R$_8$, R$_9$, R$_{12}$, R$_{13}$, and R$_{16}$ are each independently a hydrogen atom or a deuterium atom.

5. The compound of claim 1, wherein in Formula 1, Ar is any one of Formulae 2a to 2g below:

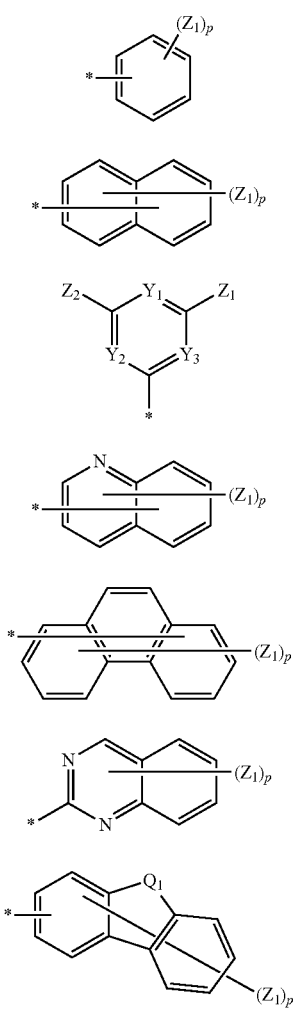

in Formulae 2a to 2g, $Q_1$ is —C($R_{31}$)($R_{32}$)—, —N($R_{33}$)—, —S—, or —O—;

$Z_1$, $Z_2$, $R_{31}$, $R_{32}$ and $R_{33}$ are each independently a hydrogen atom, a deuterium atom, a substituted or unsubstituted $C_1$-$C_{20}$ alkyl group, a substituted or unsubstituted $C_6$-$C_{20}$ aryl group, a substituted or unsubstituted $C_1$-$C_{20}$ heteroaryl group, a substituted or unsubstituted $C_6$-$C_{20}$ polycyclic group, —Si$R_{41}R_{42}R_{43}$, a halogen atom, a cyano group, a nitro group, a hydroxy group, or a carboxy group;

$R_{41}$, $R_{42}$ and $R_{43}$ are each independently a substituted or unsubstituted $C_1$-$C_{20}$ alkyl group or a substituted or unsubstituted $C_6$-$C_{20}$ aryl group;

$Y_1$ to $Y_3$ are each independently CH or N;

in Formula 2a, p is an integer of 1 to 5;

in Formula 2b, p is an integer of 1 to 7;

in Formula 2d, p is an integer of 1 to 6;

in Formula 2e, p is an integer of 1 to 9;

in Formula 2g, p is an integer of 1 to 7;

in Formula 2f, p is an integer of 1 to 5; and

* represents a binding site to N of Formula 1.

6. The compound of claim 1, in Formula 1, $R_2$, $R_3$, $R_6$, $R_7$, $R_{10}$, $R_{11}$, $R_{14}$, and $R_{15}$ are each independently any one of Formulae 3a to 3b:

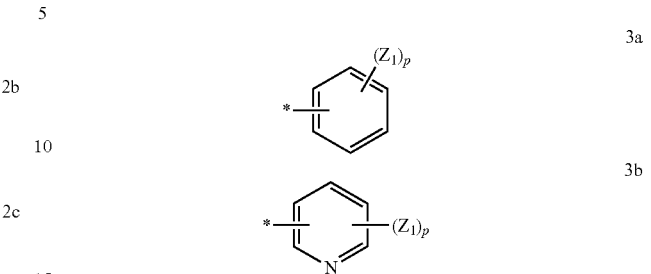

in Formulae 3a to 3b, $Z_1$ is a hydrogen atom, a deuterium atom, a substituted or unsubstituted $C_1$-$C_{20}$ alkyl group, a substituted or unsubstituted $C_6$-$C_{20}$ aryl group, a substituted or unsubstituted $C_1$-$C_{20}$ heteroaryl group, a substituted or unsubstituted $C_6$-$C_{20}$ polycyclic group, a halogen atom, a cyano group, a nitro group, a hydroxy group, or a carboxy group;

in Formula 3a, p is an integer of 1 to 5;

in Formula 3b, p is an integer of 1 to 4; and

* represents a binding site to a carbon of Formula 1.

7. The compound of claim 1, wherein the compound represented by Formula 1 is any one of compounds 1 to 57:

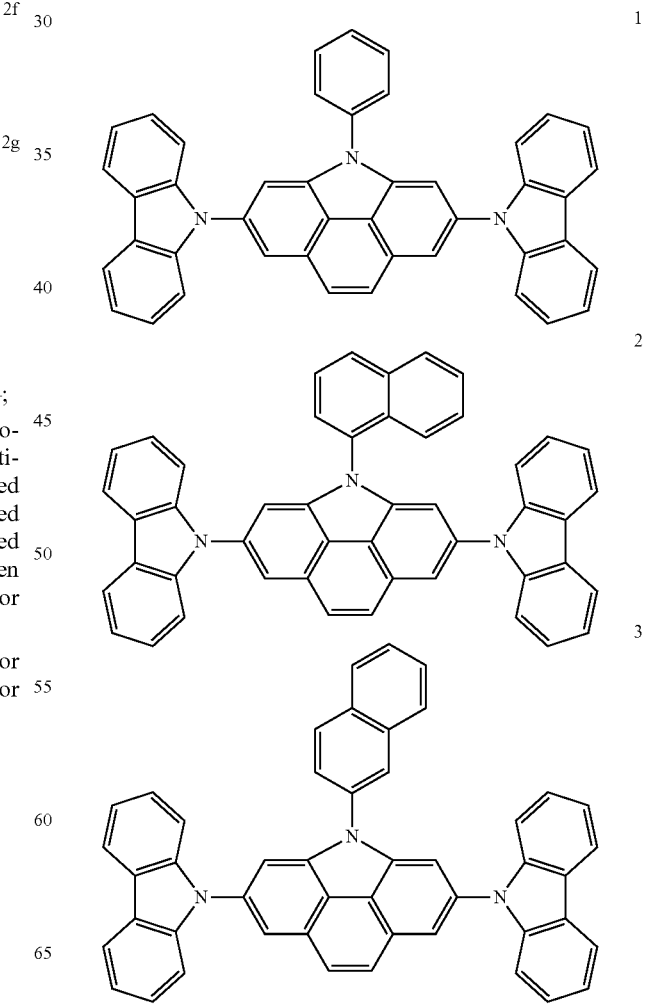

-continued
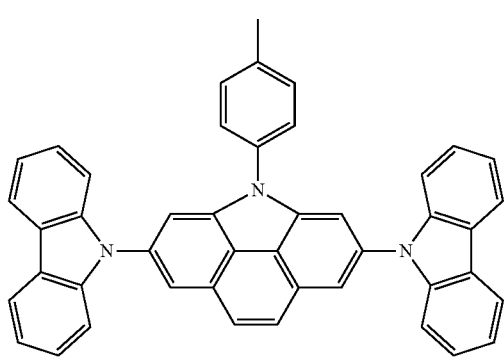
4
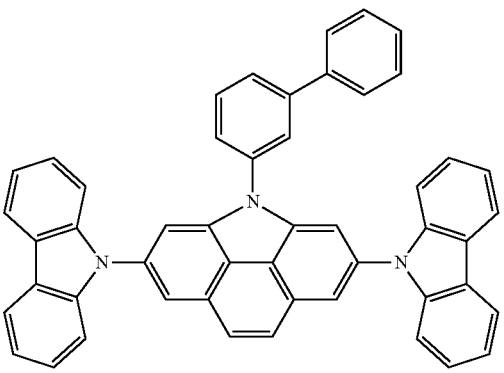
8
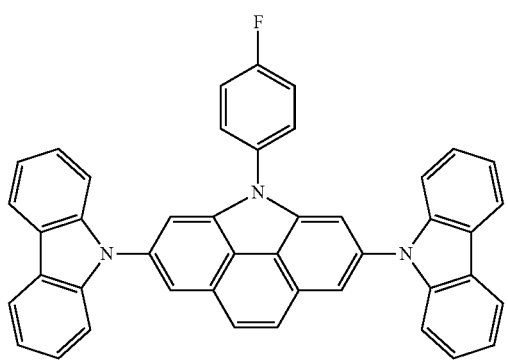
5
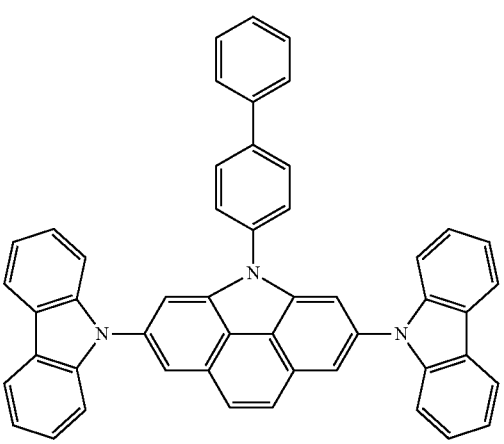
9
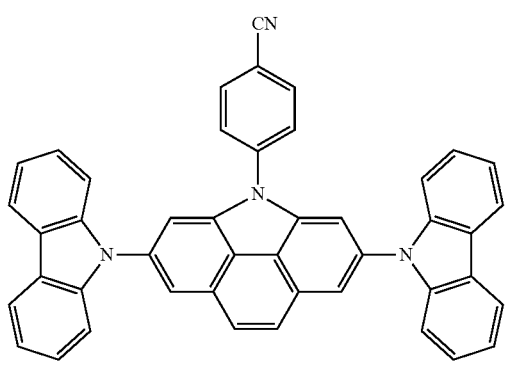
6
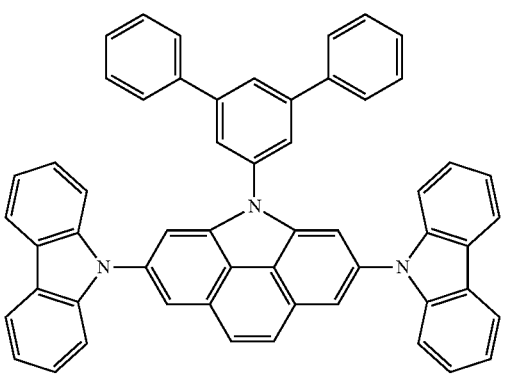
10
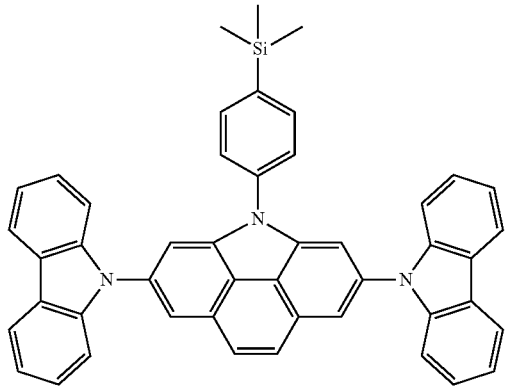
7
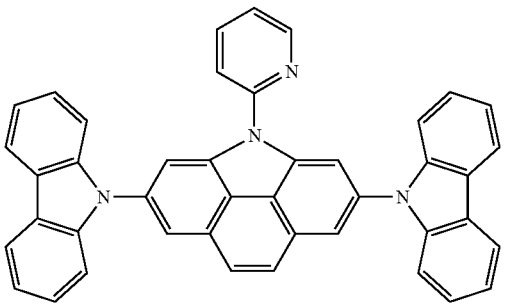
11

12
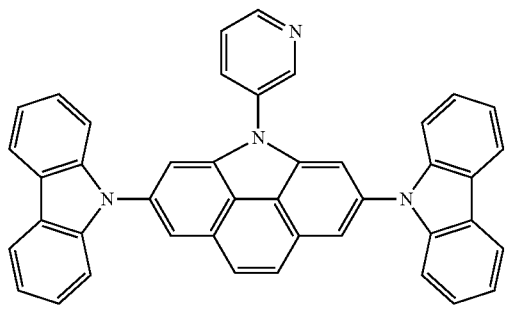
13
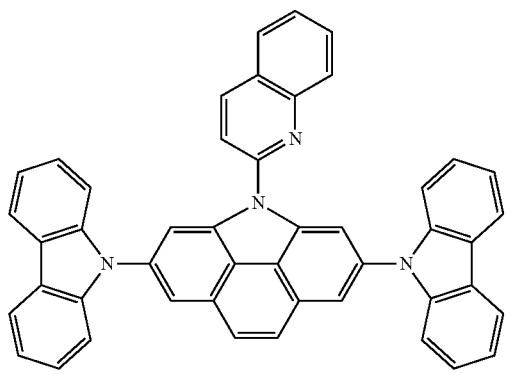
14
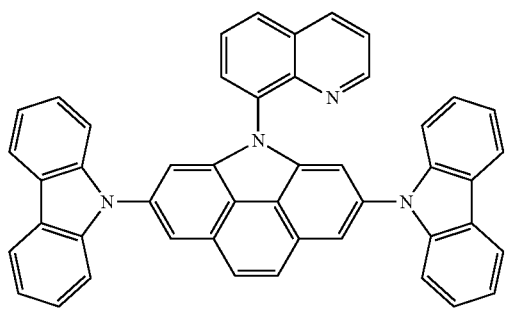
15
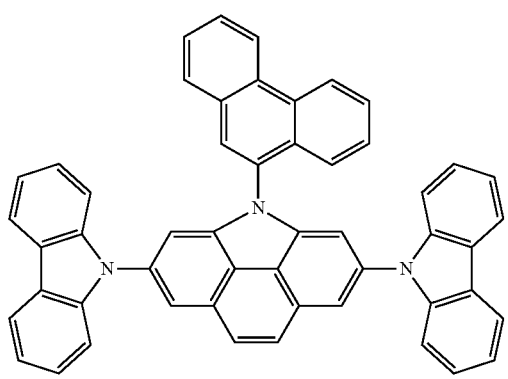
16
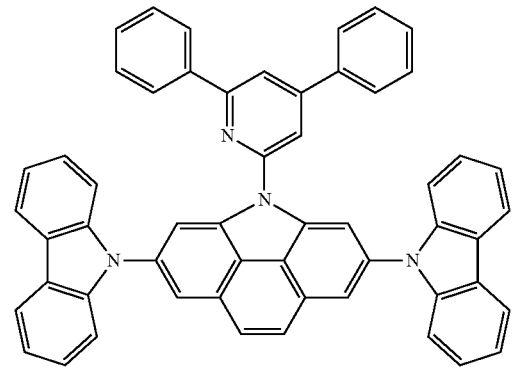
17
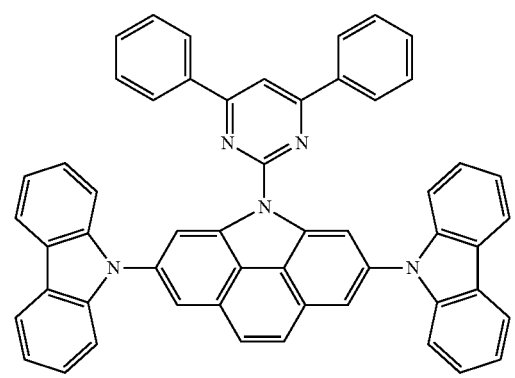
18
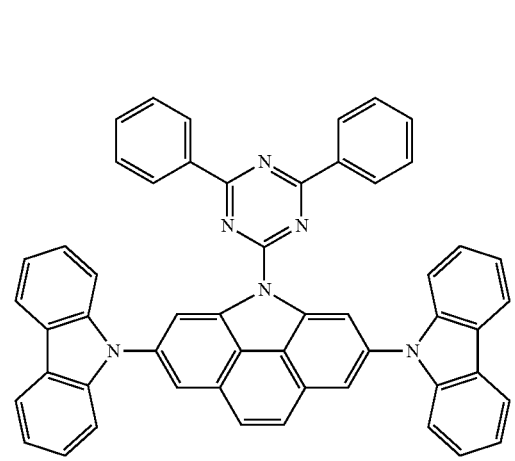
19
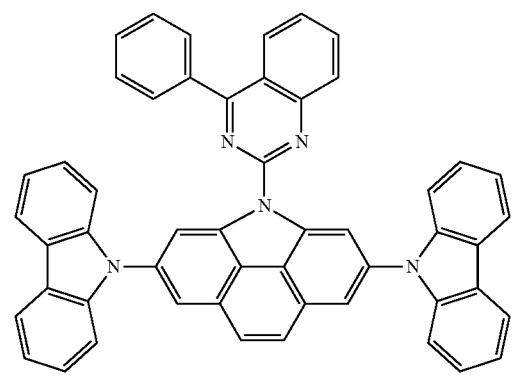

91
-continued
20
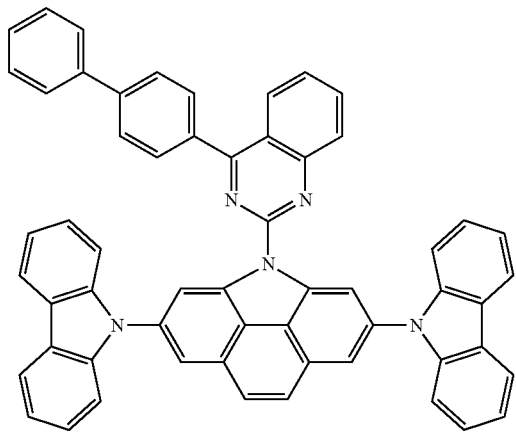
21
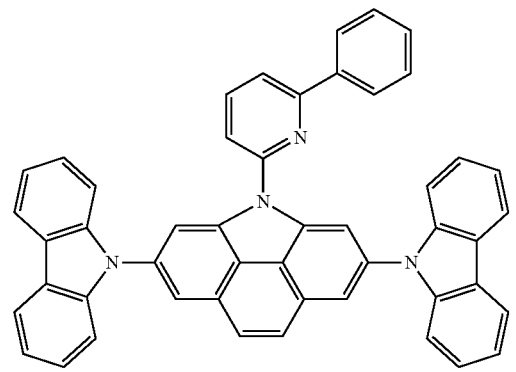
22
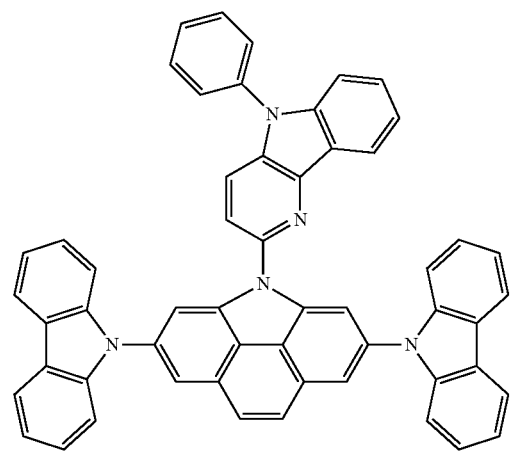
23
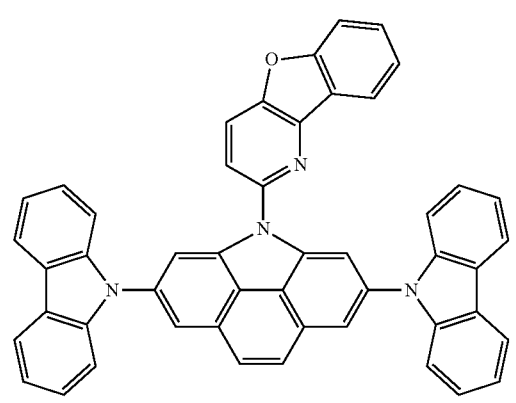
92
-continued
24
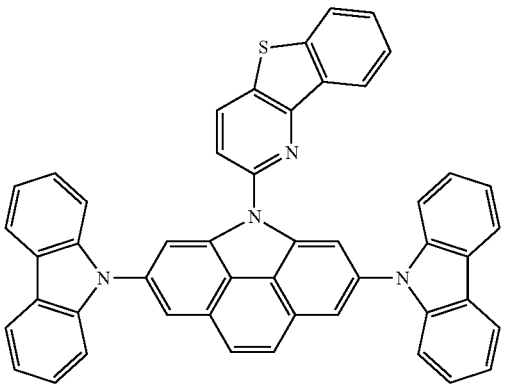
25
26
27
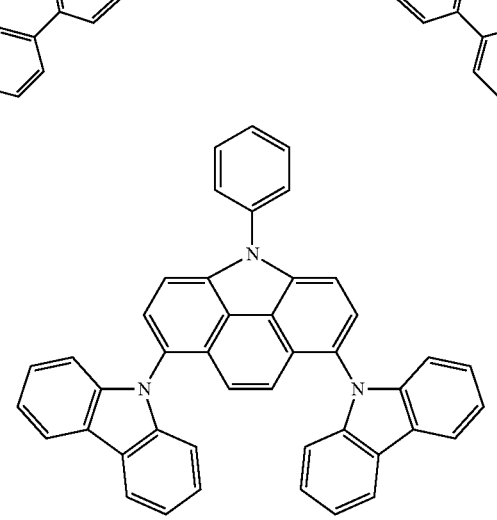

28
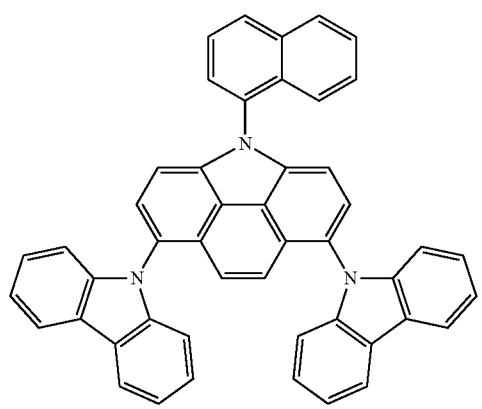
29
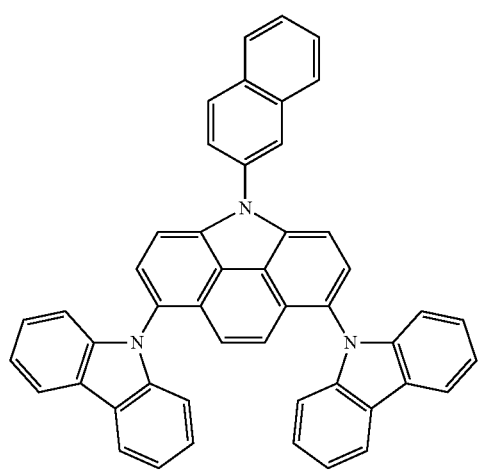
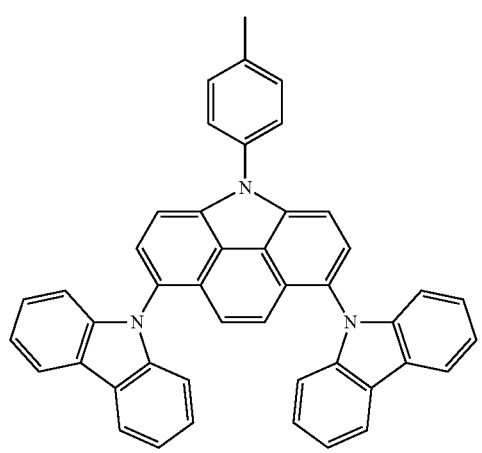
31
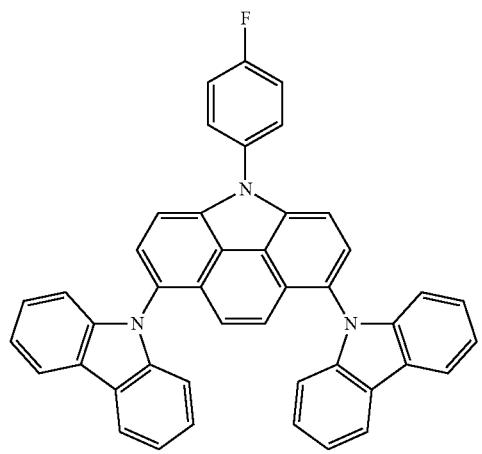
32
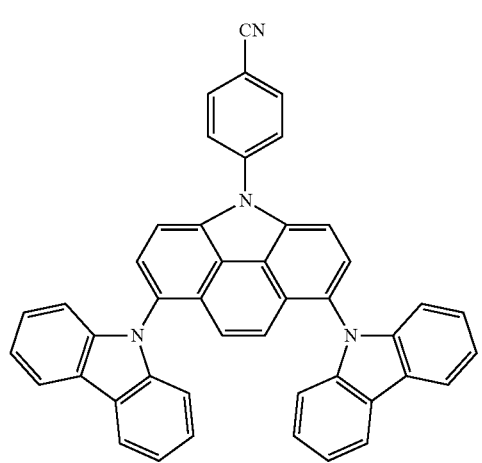
33
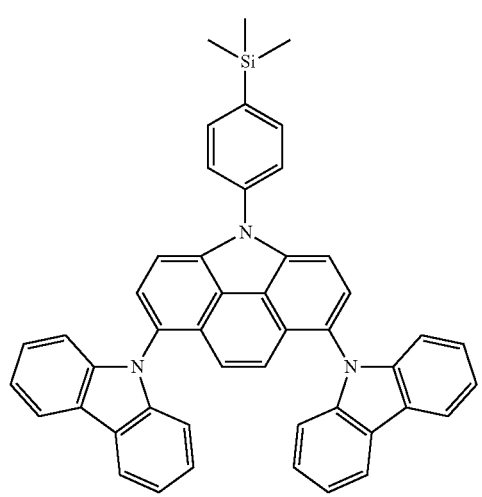

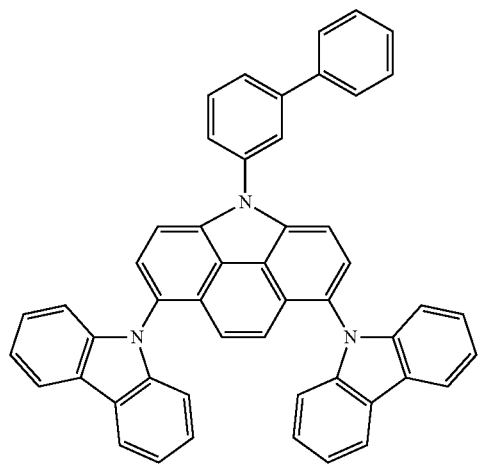
34
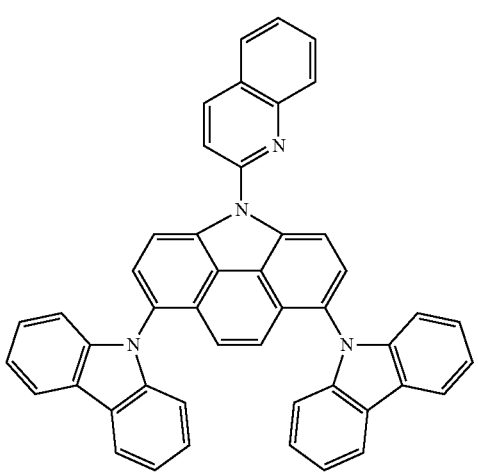
37
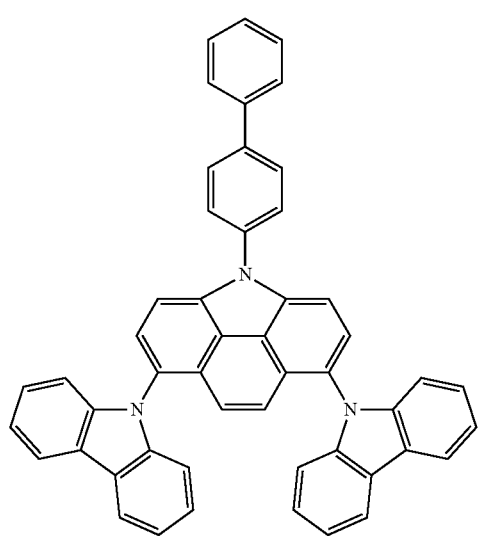
35
38
36
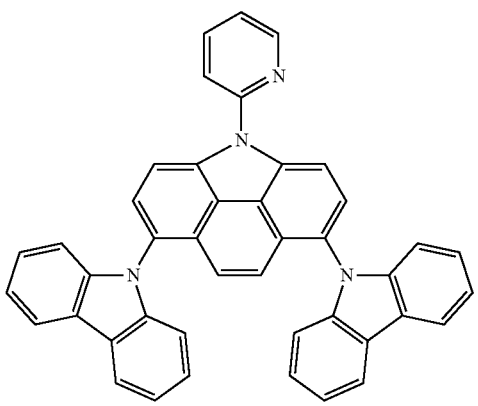
39

40
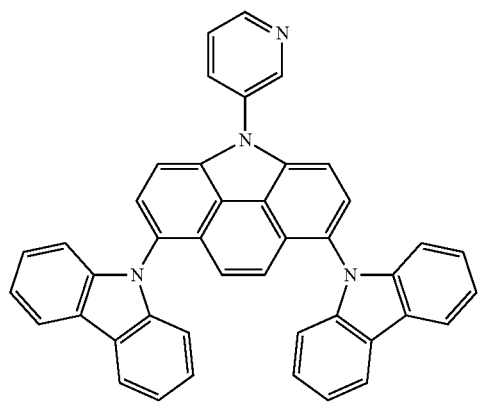
41
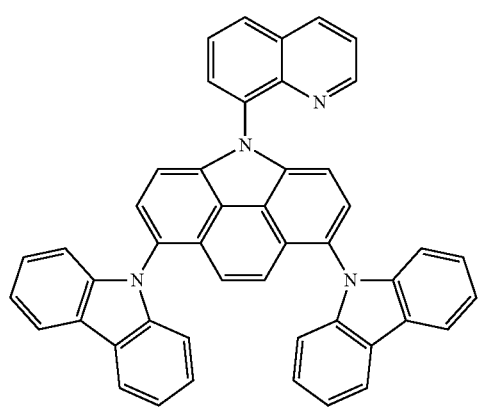
42
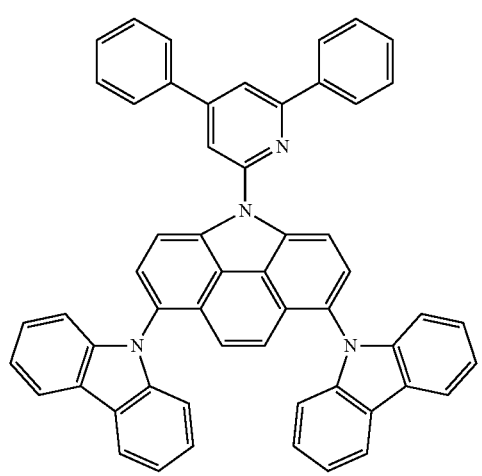
43
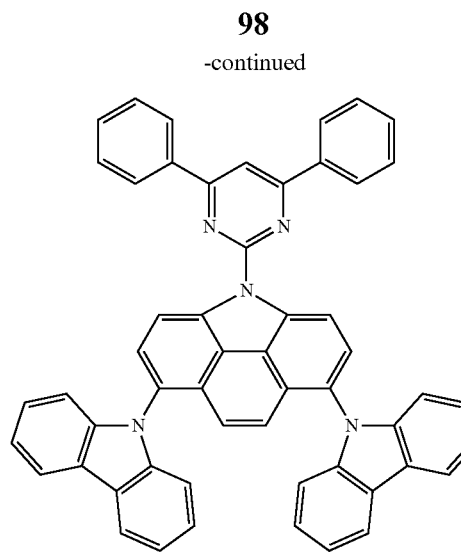
44
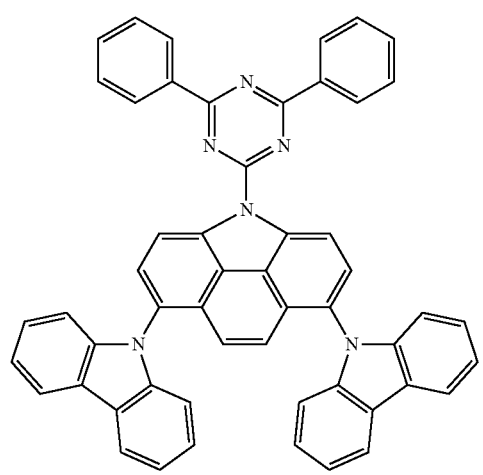
45
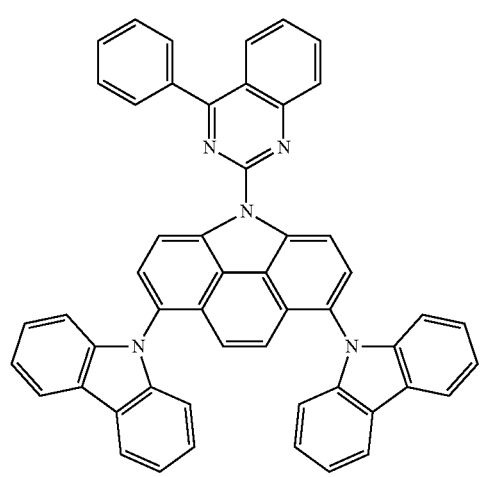

99
-continued
46
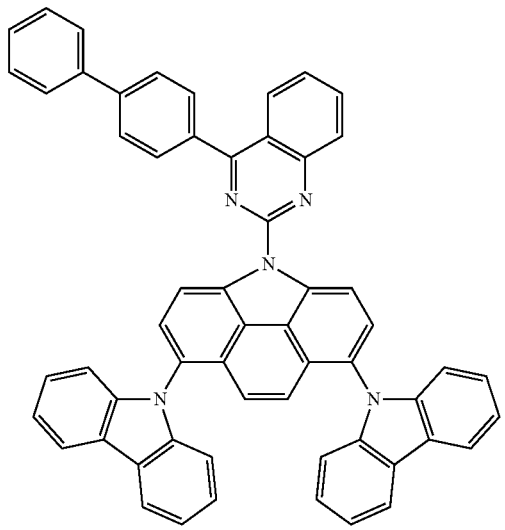
47
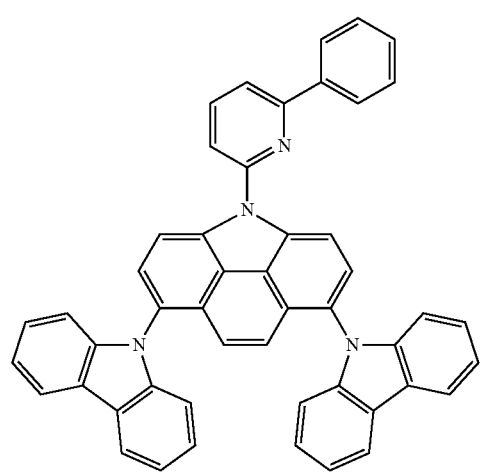
48
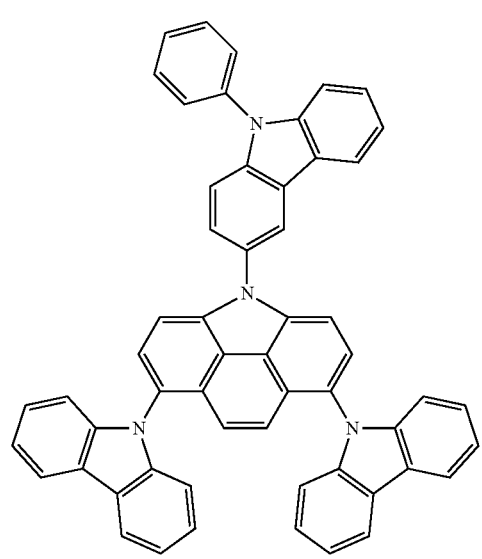
100
-continued
49
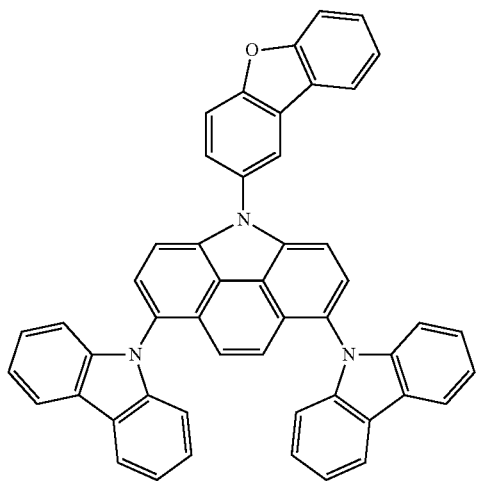
50
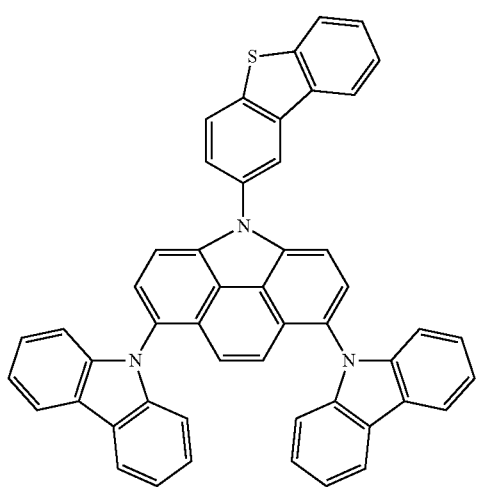
51
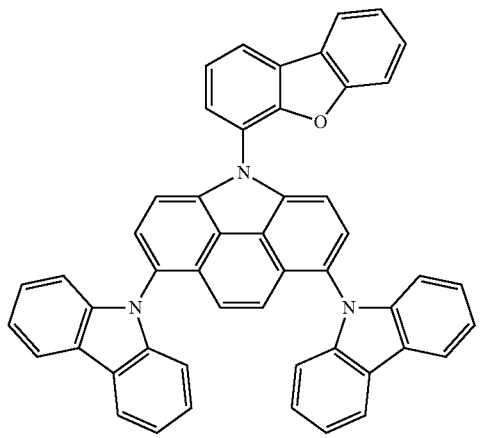

101
-continued

52

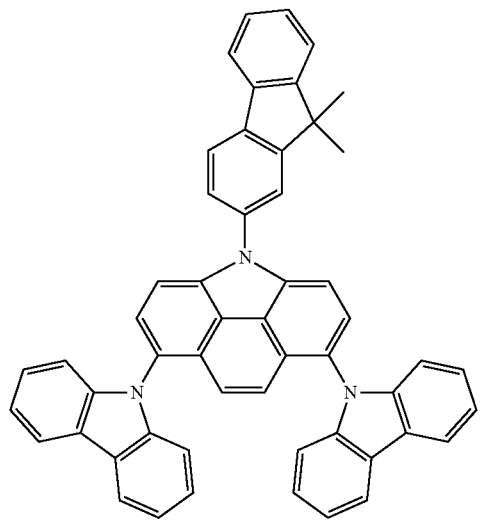

53

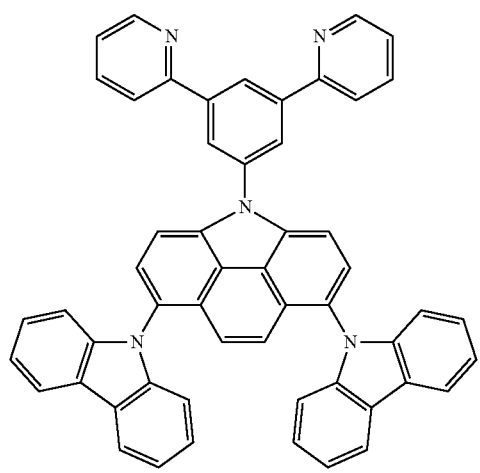

54

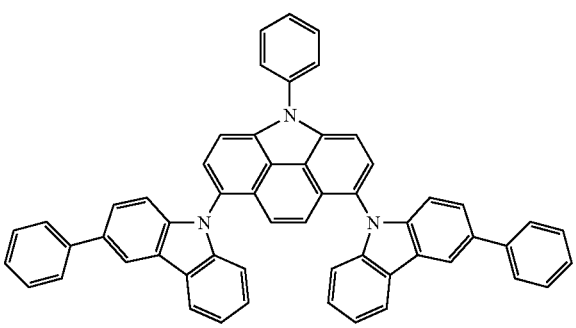

102
-continued

55

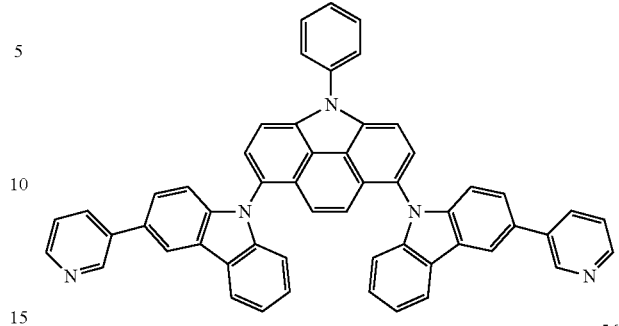

56

57

8. An organic light-emitting device comprising:
   a first electrode;
   a second electrode; and
   an organic layer between the first electrode and the second electrode, wherein the organic layer comprises the compound of claim 1.

9. The organic light-emitting device of claim 8, wherein the organic layer comprises an emission layer and the compound is a host.

10. The organic light-emitting device of claim 8, wherein the organic layer comprises an emission layer and the compound is a phosphorescent host.

11. The organic light-emitting device of claim 8, wherein the organic layer comprises an emission layer, an electron-injecting layer, an electron-transporting layer, a functional layer having both electron injecting and electron transporting capabilities, a hole-injecting layer, a hole-transporting layer, or a functional layer having both hole-injecting and hole-transporting capabilities, and wherein the emission layer comprises an anthracene-based compound, an arylamine-based compound, or a styryl-based compound.

12. The organic light-emitting device of claim 8, wherein the organic layer comprises an emission layer, an electron-injecting layer, an electron-transporting layer, a functional layer having both electron injecting and electron transporting capabilities, a hole-injecting layer, a hole-transporting layer, or a functional layer having both hole-injecting and hole-transporting capabilities, and wherein any one layer of a red layer, a green layer, a blue layer, or a white layer of the emission layer comprises a phosphorescent compound.

13. The organic light-emitting device of claim 12, wherein the hole-injecting layer, the hole-transporting layer, and/or the functional layer having both hole-injecting and hole-transporting capabilities comprises a charge-generating material.

14. The organic light-emitting device of claim 13, wherein the charge-generating material is a p-dopant.

15. The organic light-emitting device of claim 14, wherein the p-dopant is a quinone derivative.

16. The organic light-emitting device of claim 14, wherein the p-dopant is a metal oxide.

17. The organic light-emitting device of claim 14, wherein the p-dopant is a cyano group-containing compound.

18. The organic light-emitting device of claim 8, wherein the organic layer comprises an electron-transporting layer comprising a metal complex.

19. The organic light-emitting device of claim 18, wherein the metal complex comprises a lithium (Li) complex.

20. The organic light-emitting device of claim 18, wherein the metal complex comprises a lithium quinolate (LiQ).

21. The organic light-emitting device of claim 18, wherein the metal complex is Compound 203:

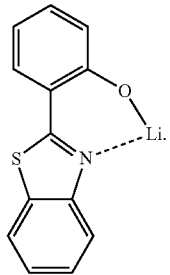

Compound 203

22. The organic light-emitting device of claim 8, wherein the organic layer is prepared by a wet method.

23. A flat display device comprising the organic light-emitting device of claim 8, wherein a first electrode of the organic light-emitting device is electrically connected to a source electrode or a drain electrode of a thin film transistor.

* * * * *